US008569473B2

(12) United States Patent
Frost et al.

(10) Patent No.: US 8,569,473 B2
(45) **Date of Patent: *Oct. 29, 2013**

(54) PESTIVIRUS SPECIES

(75) Inventors: Melinda Jane Frost, Macquarie Links (AU); Peter Daniel Kirkland, Camden (AU); Deborah Susan Finlaison, Picton (AU)

(73) Assignee: Intervet International B.V., Boxmeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/472,818

(22) Filed: May 16, 2012

(65) Prior Publication Data

US 2012/0237519 A1 Sep. 20, 2012

Related U.S. Application Data

(63) Continuation of application No. 12/298,026, filed as application No. PCT/AU2007/000521 on Apr. 20, 2007, now Pat. No. 8,202,977.

(30) Foreign Application Priority Data

Apr. 21, 2006 (AU) ................................ 2006902089

(51) Int. Cl.

| | |
|---|---|
| ***C07H 21/00*** | (2006.01) |
| ***A61K 39/12*** | (2006.01) |
| ***C12Q 1/70*** | (2006.01) |

(52) U.S. Cl.

USPC ........ 536/23.72; 424/218.1; 435/5; 435/69.1; 435/235.1; 435/320.1

(58) Field of Classification Search

None

See application file for complete search history.

(56) References Cited

U.S. PATENT DOCUMENTS

| | | | |
|---|---|---|---|
| 5,474,796 | A | 12/1995 | Brennan |
| 6,180,109 | B1 | 1/2001 | Moormann et al. |
| 2005/0031588 | A1 | 2/2005 | Sommadossi et al. |
| 2005/0287171 | A1 | 12/2005 | Meyers et al. |

FOREIGN PATENT DOCUMENTS

| | | | |
|---|---|---|---|
| CN | 1603418 | A | 4/2005 |
| EP | 0 713 915 | A1 | 5/1996 |
| EP | 1087014 | B1 | 3/2001 |
| WO | WO 99/06569 | A1 | 2/1999 |
| WO | WO 02/00881 | A1 | 1/2002 |
| WO | 02085308 | A2 | 10/2002 |
| WO | 03099861 | A1 | 12/2003 |
| WO | 2004110370 | A2 | 12/2004 |
| WO | WO 2005/111210 | A1 | 11/2005 |

OTHER PUBLICATIONS

Becher et al., "RNA Recombination between Persisting Pestivirus and a Vaccine Strain: Generation of Cytopathogenic Virus and Induction of Lethal Disease", Journal of Virology, 2001, pp. 6256-6264, vol. 75(14).

Kirkland et al., "Identification of novel virus in pigs—Bungowannah virus: A possible new species of pestivirus", Virus Research, 2007, pp. 26-34, vol. 129(1).

McOrist, S. et al. 2004 "An infectious myocarditis syndrome affecting late-term and neonatal piglets" *Australian Veterinary Journal* 82(8): 509-511.

O'Connor, B. 2001"Multiple porcine circovirus 2-associated abortions and reproductive failure in a multisite swine production unit" *The Canadian Veterinary Journal* 42(7): 551-553.

Accession #Q8JPU3 (Polyprotein—Bovine viral diarrhea virus 1 strain ZM-95); Genbank 2006.

Accession #Q8QP47 (Polyprotein—Bovine viral diarrhea virus1) ; Genbank 2006.

Accession #Q9IWA6 (Polyprotein—Bovine viral diarrhea virus 1) ; Genbank 2006.

Accession #Q9PYB2 (Polyprotein—Pestivirus giraffe-1 H138) ; Genbank 2006.

Accession #Q9WP30 (Polyprotein—Bovine viral diarrhea virus 2) ; Genbank 2006.

Accession #Q9YRM6 (Polyprotein—Classical swine fever virus) ; Genbank 2006.

Accession #Q65464 (Polyprotein—Border disease virus strain X818) ; Genbank 2006.

*Primary Examiner* — Stacy B. Chen

(57) ABSTRACT

The application relates to a pestivirus, designated PMC virus, that is associated with porcine myocarditis syndrome, and the gene and protein sequences derived therefrom. The application further relates to detection methods, vaccine therapeutics, and diagnostic methods using the PMC virus or gene/protein sequences derived therefrom.

18 Claims, 18 Drawing Sheets

Figure 1

```
gtataacgac agtagttcaa gtgtcgttat gcatcattgg ccataacaaa ttatctaatt 60
tggaataggg acctgcgacc tgtacgaagg ccgagcgtcg gtagccattc cgactagtag 120
gactagtaca aataggtcaa ctggttgagc aggtgagtgt gctgcagcgg ctaagcggtg 180
agtacaccgt attcgtcaac aggtgctact ggaaaggatc acccactagc gatgcctgtg 240
tggacgagga catgtccaag ccaatgttat cagtagcggg ggtcgttact gagaaagctg 300
cccagaatgg gtagttgcac atacagtctg ataggatgcc ggcggatgcc ctgtattttg 360
accagtataa atattatccg ttgtaaagca tatgaatact tttactttta atacatatgg 420
agggagtgag gaaggaaaca tgttctttag aactgcaccc acgccgccac cagggtgcca 480
agaaccggtt tacacaagca caatgagacc aatttttggc gaaccccatc cacctctaca 540
caaacacagc acgttaaaat tgccacattg gaggggggatc aaaacaatta gagttaagaa 600
gagagaattg ccaaagaagg gcgattgtag caactcaaca acagctccca cttcggggt 660
gtacgttgaa ttaggggctg tgttctataa agattacacg ggcacggtat accatcgtgt 720
accgctagaa ctttgtacaa accaagagag gtgcgaggga tccaagtgtg tagggagaat 780
gacagggtct gatggcaggt tgtacaacgt tttagtatgt ccggacgatt gtatcctctt 840
tgagagacac tgtagaggtc aaacagtcgt cctgaaatgg atttccaacc ccttgacatc 900
accactttgg gtccagagtt gttctgacga caaaggagca aaacccaagg tgaaaccaaa 960
agacgacagg atgaagcaag gaaaaatagt gacaaagcct aaagagactg aagcagatca 1020
aaaaactaga ccaccagatg ccacgatagt ggttgacggg cagaagtatc aggtgaggaa 1080
gaaggggaaa gcgaaaccca agactcaaga cggcttatac cacaacaaga acaaaccaga 1140
agcgtccagg aagaagcttg agaaggcctt gctagcatgg gcaatattag cctgcctatt 1200
ggtggtaccg gtagggtcca ccaacgtgac acaatggaac ttatgggaca ataaaagtac 1260
tacagacata catagcgtca tgttttctag agggattaaa aggagtctgc atggaatttg 1320
gcccacacaa atctgcaaag ggatccctac acatctagca gcagactatg aactgaaaag 1380
gattcacggg atggtggatg caagccccat gaccaacttc acatgttgta ggctacagag 1440
acatgagtgg aacaagcatg ggtggtgcaa ctggtacaat atagagccgt ggatcaatct 1500
catgaataat acccaaggac tattaaacac tggagacaat ttcactgagt gcgcagtcac 1560
atgcaggtat gatgcagact taggggtgaa tatagtgact caagccagga ctactccaac 1620
tatcctgact ggctgtaaga aagggcacaa cttctctttc tcaggggagg tcagggcctc 1680
accctgcaac tttgagttaa ctgctgaaga cttgctcagg atcatggatc acaccaactg 1740
cgagggattt acctacttcg ggaaggaat cgttgacggt tacaccgagg tagtagagaa 1800
ggccaggtca agtggtttca gggctctcac atggttgtcg agtaagattg aaaacaccaa 1860
gaaaaaaata ttcggagctg aagccagtcc ttactgccca gtggctaaga gggtcttcaa 1920
cattatttat accaacaatt gcaccccgct tggactgcca gataagtcaa aaattatagg 1980
accaggaacc tttgacatca gtggcaggga tgaattcata tttccaaaac tcccctacca 2040
cgtagatgac ttcattctac tgagcttaat tgcaatgtct gattttgctc cagagacatc 2100
aagtataatc tacctggctt tgcactacct aatgccaagt aatgacaaca gggacttcgt 2160
gatggacctg gacccaaata aactaaacct tactgcaact aaatccgtgg caagtgtggt 2220
ccctacatcg gtgaatgtgt taggtgaatg ggtgtgcgtc aaaccaagtt ggtggcctta 2280
ttccgccgaa atcactaatc tgataggagg tgtcatcacc gtggcagact tagttatcaa 2340
gaccattgaa gaattgctaa atttgtggac cgaagcaaca gctgtggcat ttctggctgc 2400
tctaataaaa atttttagag gccagccgat ccaagcggta gcatggttaa tcatcatagg 2460
gggagcacaa gcccaaacct gcaaccctga attcatgtac gcattagcga aaaataccag 2520
cataggttca ttaggaccag aatcactgac gacaaggtgg taccaactaa ccagcggttt 2580
caaactcact gacagcacga ttgaagtcac ctgtgtgggt gctaacatga ggattcatgt 2640
agtgtgccca cttgtaagtg acagatattt ggccataaac caccctagag cactgccaac 2700
aacggcgtgg ttcaggaaaa tacacactca gcatgaggta ccaagagaaa gaatcatgag 2760
tgagtcaaaa aggaggtaca cttgtccttg tggttctaaa ccagtggtga ggtcaacaac 2820
acaattcaac ccaatatcta tatctacccc aagctttgaa cttgaatgcc ctaggggttg 2880
gactggggct gtagagtgta cactagtctc cccatcaact ctgacaacag agactatatt 2940
cacatacagg aagcccaaac cattcggact tgaaaactgg tgcaagtata cagtggtgga 3000
gaaagggatc ctgtattctt gtaaatttgg gggcaattca acatgcatca aagggcttat 3060
agttaaaggg caacgggaag acaaagtaag gtactgtgaa tggtgtggtt ataagttcag 3120
ttcaccaaat ggactgcctc agtatccact gggattgtgt gagaaagaac aatcagaagg 3180
actcagggat tatggtgact tcccatgctg caacaacggc acttgtattg acaaagaagg 3240
tagtgtgcaa tgctacatag gggataagaa agttaccgtg aagctgtata atgcctcact 3300
attggccccc atgccctgca aacccatagt gtataactcc caggggcccc cagcgcctaa 3360
gacctgcact tataggtggg cctcaacatt agaaaataaa tattatgaac ccagggacag 3420
ctactaccag caatacatta taaagtcagg gtatcaatat tggtttgatc tcacagcaaa 3480
```

```
ggatcatgtg gcagactgga tcacaaaata ctttccaata ataatagtgg ccttgttagg    3540
gggcagaggc accttgtggg tgttgatagc ttatgagttg ctaactcagt atgaggtagt    3600
aggagacgag aacatagtgg ctcaagctga agccctggta atcggaaaca tcttgatgag    3660
tttagactta gagataatta gctgcttcct tctgttgttg atcgtggtga aaaaacaagc    3720
tgtcaggaga acgttggctt tactgtttca ttggataact atgaacccat tccagtcagt    3780
aatgatcaca gtggtctact tcgtcggttt ggtgagggcc gaagagggaa ctaaagaggg    3840
tagtacaagc gggccaccaa tccatgtagt tgcaatactg ttattcctct tgtaccacac    3900
agtgaagtat aaggacttta acatagcaat gatcttactt ataacattgt ccctgaaaag    3960
ctcatcctac atacatacca gcttgtatga aattccattg cttgtggctg taataagtct    4020
cacatgctcc atatacattt ttgacttgca ggtaaagagc aagctagtgg ccccaactat    4080
aggtataatt ggagttaccc tagcaatgag agttttgtgg ctggtaaggc aaatgactat    4140
accaaccccc tctgtgtcca ttagtctgat agatccaaag atggtcataa tactctactt    4200
gatatcccta actattacag tcaatcacaa cctagaccta gcaagttatt gcttgaaact    4260
gggacctttt atcctatcat tcctaacaat gtgggtggat gttgtcatcc tcctgctcat    4320
gctgccttgg tacgaactag taaaagtcta ctacctaaaa aagaagaaag aggatgtgga    4380
aacatggttc caaaattcag gaatatccac ccaagaaact tccccatacg gatttgattt    4440
ttctagcccc ggggagggag tgcacacact accaatgcaa aataaaacca aattttgtag    4500
gactgcttac atgactgtac taagggcttt ggtgataaca gccatcagca gtgtctggaa    4560
accaataatt ttagcagaac tcctaataga ggcagtgtat tggacacaca ttaaaatagc    4620
caaagaattg gcggggtcaa gcaggttcgt tgctaggttc attgcatcta ttatagagtt    4680
gaattgggcc atggacgaaa aagaagcatc tcggtacaaa agattttacc tattatcatc    4740
caaaataaca gatctaatgg ttaagcacaa aatccaaaat gagacagtaa aatcctggtt    4800
tgaagaaact gaaatatttg gaatacaaaa agtggcaatg gtgataaggg ctcattctct    4860
gagtttggag ccaaatgcca tcctttgctc cgtttgtgaa gaaaaacaaa atcaaaaagc    4920
caaaaggccc tgccctaagt gtggtagtag aggcactcaa ataaagtgtg ggctgacact    4980
ggccgagttt gaggaagaac attacaaaaa aatatacatc ctcgaaggcc aagatgaaac    5040
tcccatgagg aaagaagaaa gacagcaagt aacttatgtc tctaggggtg ctctgttcct    5100
taggaatctt cctatcttag cttcaaaaaa caaataccta cttgtaggca atctgggtat    5160
ggaattgcaa gatttggaaa gtatgggatg gatcattcga gggccagccg tctgcaagaa    5220
gataatacac catgagaaat gcaggccttc aataccagac aaactcatgg cattcttcgg    5280
gattatgcct aggggagtta caccaagagc ccctacacgg ttccctgtgt ccttgctgaa    5340
gataagacgg ggttttgaga ccggctgggc ctacacacac cctggagggg taagtagtgt    5400
gatgcatgtc accgctgggt cggatatata tgtcaatgac tcaataggga ggacaaaaat    5460
ccagtgccaa gacaaaaaca ctacaacaga tgagtgtgaa tatggtgtga aaacagactc    5520
agggtgctct gatggagctc ggtgctatgt catcaaccct gaagcaacca acatagcagg    5580
gaccaagggg gccatggtac acctgaggaa agctggagga gagttcaact gcgtgactgc    5640
ccagggtacc cccgccttct ataatctaaa gaacttaaaa ggatggtcag gcctgcctat    5700
ctttgaagct gccacaggaa gagtggtagg aagggtaaaa gcaggaaaaa acactgacaa    5760
tgctccaaca accattatgt cagggacgca agtggcaaaa ccatcagagt gtgacctaga    5820
atcagtggtg aggaaactag agacaatgaa cagaggggaa ttcaaacaag tgactctggc    5880
tacaggcgca ggaaagacaa ccatgctacc aaagctgtta atagaatcca taggcaggca    5940
taagagagtg ttagtactga tcccgttgag agctgcagcg gagggggtgt accagtacat    6000
gagaaccaaa cacccaagca tatctttcaa cttgaggata ggggatctga aagaaggtga    6060
catggcaact gggatcacct atgcctctta tgggtacttc tgccaaatgg acatgcctag    6120
actggagaat gcaatgaagg aataccacta tattttcttg gatgaatatc actgtgccac    6180
accagaacag ttggcagtga tgtcaaaaat acataggttc ggtgaatcag ttagggtaat    6240
agccatgacc gccacgccat ccgggactgt gagcacaaca gggcagaaat tcacaattga    6300
ggaggtggta gtacctgaag tgatgaaggg ggaggacctt gctgatgatt acatcgaaat    6360
agcagggttg aaggtgccaa agaaagagtt agagggtaac gtactgactt ttgtgcctac    6420
aaggaagatg gcatcggaaa cagcaaaaaa attaaccaca cagggataca atgctggata    6480
ctacttcagt ggagaagatc catcatccct gcggacaact acttctaagt caccatatat    6540
agtagttgca accaatgcca ttgaatccgg ggtaacctta ccggaccttg atacagtaat    6600
agatacaggc atgaagtgtg aaaagagact aagaatcgaa aacaaagctc cctacatcgt    6660
aacaggactg aaaagaatgg ctataacaac gggggagcaa gctcaaagaa aaggtagggt    6720
aggcagggtt aaacctggga ggtacttgag aggacctgaa aacactgcag gtgaaaagga    6780
ctatcactat gaccttttac aggcacagag gtacggcatc caagactcaa taaacatcac    6840
caagtctttc agggagatga actatgattg ggcattatat gaggaagacc cgttaaagat    6900
tgcccaatta gagttgctaa acacactcct gatctcaagg gatctgccag tagtaacaaa    6960
aaatctgatg gcccgcacaa cacatcccga acctatacaa ttggcttaca atagtttaga    7020
aacccctgta ccggtggcat tcccaaaagt gaaaaatgga gaagtcactg acgcacatga    7080
aacttacgag ttgatgacct gtaggaagct tgagaaagac ccccctatat acctgtatgc    7140
aacagaagaa gaagatctcg tagtggacat actgggattg aaatggccag acgccacaga    7200
gagggctgtc ttggaagtgc aagacgccct gggccagatc acaggtttat ctgcagggga    7260
```

Figure 1 (continued)

```
gacagcttta ctcatagccc tattagggtg ggtgggctac gaagccttgg tgaagaggca   7320
cgtgcctatg gtgacagaca tatacaccct agaagatgaa aaattggaag acactacaca   7380
cctacaattt gccccagatg atctgaacaa ttcagatacc attgagctcc aagacttatc   7440
gaatcaccaa atccaacaaa ttctagaagg tgggaaggaa tatgtcggcc aagcctacca   7500
attcctcagg ttgcaagctg agagggctgc caactcagac aaaggcaaga aagcaatggc   7560
agcggcccca ttactagccc acaagttcct ggaatacttg caagagcatg caggtgacat   7620
aaagaagtat ggtctatggg gggtccacac agcattgtat aacagcataa aagaaagact   7680
gggtcacgaa actgcattcg catctctggt tataaaatgg attgcctttt cctcagatgg   7740
agtcccgggg atgattaagc aagcagcagt agacttggtg gtatactata taatcaacag   7800
gcctgagtat caaggggata aggagacaca gaatgcaggt agacaatttg ttggctccct   7860
ttttgtttca tgtctagcag agtacacatt caaaaacttc aataaatcag cattagaagg   7920
attgatcgag cctgccttaa gctatctacc ctacgcttca agcgcactaa agttattcct   7980
accgactaga cttgaaagtg tagtgatact gtccactact atatacagaa catacttatc   8040
aatcaggaaa ggatctagtc agggtttagc cgggctggca gttagctcag cgatggagat   8100
catgaaccag aacccaatca gcgtggctat tgcactggca ctaggagtcg gagcaatagc   8160
ggcacataat gccattgaga gcagtgaggc aaaaaggact ctcctgatga aggtctttgt   8220
taagaacttt ttggaccaag cagccactga tgagcttgtg aaagagaacc ctgagaagat   8280
cataatggca gtgtttgagg gcattcaaac agctggaaat ccattgagac ttgtatacca   8340
tctatatgca atgttctaca aagggtggac tgccgcggaa atagctgaaa aaaccgctgg   8400
taggaacatt tttgtgttaa caatatttga aggattggaa atgttaggcc tggatgccga   8460
ctcaaaatgg agaaatctga gctctaatta tcttattgat gcagtgaaga aaatcattga   8520
aaaaatgact aaaacagcaa caagcttcac ctacagcttt ttgaaatctt tgcttcctgc   8580
cccctctcg tgtactaaat cagaaagaga tccaagaata gggtggcccc aaaaagacta   8640
cgactacctc gaggtccgat gcgcttgtgg gtataacagg agagctataa aaagagactc   8700
aggacctgtg ttatgggaga ccttagagga gacgggtcca gagtactgcc acaacagagg   8760
tgaaaggggg ctcagcaatg tgaagactac tagatgcttt gtccaaggag aggaaatccc   8820
tccaattgca ctgaggaaag gagtaggtga gatgttggtc aagggtgttt cattcagaat   8880
agattttgat aaagacaaga tactttcaac agacaagtgg aaggtaccac atagggcagt   8940
tacatcaatc tttgaggatt ggcagggtat tggttacaga gaggcttacc tagggaccaa   9000
accagactat gggggtctgg tgcccagatc ttgtgtaact gtaacaaaac aagggttaac   9060
attcttgaaa actgccagag gcatggcttt cacgactgac ctgaccatcc agaacatcaa   9120
aatgctgata gctacatgct tcaagaacaa ggtgaaggaa ggggagatac cagctacgat   9180
tgaaggggaa acatggatca acataccact agtgaatgag gacaccggga ccattaaacc   9240
aagcttcggg gaaagagtga ttcccgaacc atatgaggag gacccacttg aaggcccaag   9300
tgtaatcgtt gaaacaggag gcatagccat caaccaaata ggggtcaatc cacaatccag   9360
tacatgtgga acagttttta cagcagtgaa ggatctgtgc caaacagtta gtaataaagc   9420
caagaatatc aaaattgggt tttcggaagg ccaataccca ggtccagggg ttgcaaagaa   9480
gacactgaac cagctcatac aagatgaaga cccaaaacca ttcatatttg tttgtggctc   9540
tgacaagtca atgtctaatc gggcaaaaac tgcgaggaac atcaagagaa tcaccaccac   9600
aacacctgag aaattcagag acttggcaaa aaacaagaaa ttgataattg tgctgttagg   9660
tgatagatac catgaagata tagaaaagta tgcagacttc aagggcacct tcttgaccag   9720
acaaaccttg gaagcactag caagtgccaa agctgtagag aaggacatga ccaagaaaga   9780
agcagcaaga gtattggcaa tggaagaaaa ggatgaacta gaactcccag ggtggctgca   9840
tacagatgca cccaaattcc tagacattac taaggacaac atcacacatc acctaatagg   9900
ggacatgcag agtctgagag aaagagcagg ggagatagga gcaaaggcca ccactcaaat   9960
cactaagaaa gggagtgtat acacaatcaa tctgagtacg tggtgggagt cagagaggtt  10020
ggcatctttg gaacctttgt tccgggaact actatctaaa tgcaggccag tggacaggga  10080
gacatataag aattgtcatt ttgcaacagc agcccaactt gccggaggaa actgggtacc  10140
ggtagcacca gttgtacatc ttggggaaat tccggtaaag aagaaaaaga ctctccccta  10200
cgaggcatac aagctcctaa aagagatggt tgactcggag aaggaattcc ataaaccagt  10260
gagcagggaa aaacaccaat ggatactgaa caaagtgaaa actggtggtg acctcggctt  10320
aaaaaatcta gtatgtccag gtagggttgg agaaccaatc ctaagagaga agaagaaatt  10380
caacatttac aacaagagga ttaccagtac tatgttatca gtagggataa ggccagaaaa  10440
attgccagtg gtaagagccc agaccagtac caaagaattt catgaagcaa taaggacaa   10500
aatagacaaa aaagcaaaca cacagacccc aggcctacac aaagaattgt tggagatatt  10560
caactcaata tgtgccatcc ccgaacttag aaatacctac aaagaggttg attgggacgt  10620
tctaacctca ggcataaata ggaaaggtgc agccgggtac ttcgaaaaaa tgaacatagg  10680
ggagatcata gatagtgaca aaaaatcagt ggaacaactc ataaagagaa tgaaatcagg  10740
gctagaattc aactactatg agactgcaat accaaaaaat gagaagaggg cagtggtaga  10800
tgattggatg gaaggtgact atgtagaaga aaaaagacca agagtcatac agtatcctga  10860
ggcaaagatg agattagcta taaccaaagt aatgtataac tgggtcaagc agaagcctat  10920
agtaatccct ggatacgaag gtaagactcc tttgtttcat gttttcgaca aggtccacaa  10980
agaatggaaa aatttcaaca gtccagttgc agtcagtttt gacactaaag cctgggacac  11040
```

Figure 1 (continued)

```
acaagtaaca cccaaagacc ttctcctcat atcagaaatc caaaagtatt attacaagaa   11100
agaataccat agattcatag ataatttgac cgagaaaatg gtggaggtac cagtggtttg   11160
tgaagacgga aacgtctaca taagagaagg tcagagggga agtggtcaac cagacactag   11220
cgcaggtaat agtatgttga atgtactgac tatgatatat gccttctgca aagctaactc   11280
catcccttac tcagccttcc acagggtagc aaagatacat gtgtgtggag atgatggttt   11340
cttgataact gagaaaagtt ttggtgaggc ctttgcgatc aaggggcctc aaattttgat   11400
ggaagcagga aaaccacaaa aacttatagg tgaatttgga ctgaaattgg catataaatt   11460
tgatgacatt gaattttgct cgcatacacc aataaaggtc aggtgggctg acaacaacac   11520
atcatacatg cccggaagag acacagctac cattctagct aaaatggcaa cccgccttga   11580
ctctagtggg gagaggggga ccgagggata cgagctggcc gtggccttca gtttcttact   11640
aatgtattct tggaaccccc tggtaagaag aatatgcctg cttgtcatgt ctacaattga   11700
cacaaaagaa gctagccaaa ataacactat atatacattt agggggggatc ccataggtgc   11760
ctacacagag gtaattgggt ataggctgga ccaactaaaa cagacagagt tctctaaatt   11820
ggctcagctg aatttgtcaa tggcaatact tcaaatatac aataaaaaca caaccaagag   11880
actcatcgaa gattgtgtga aacttggcaa ccaaaataag caaatattgg tgaatgcaga   11940
ccgtttgatc agcaagaaaa cgggctacac atatgagcca acagctggcc acactaagat   12000
aggcaagcac tatgaagaaa tcaacctgct gaaagataca ccacaaaaaa ctgtctacca   12060
aggaactgaa aggtata                                                  12077
```

```
GGSEEGNMFF RTAPTPPPGC QEPVYTSTMR PIFGEPHPPL HKHSTLKLPH WRGIKTIRVK   60
KRELPKKGDC SNSTTAPTSG VYVELGAVFY KDYTGTVYHR VPLELCTNQE RCEGSKCVGR  120
MTGSDGRLYN VLVCPDDCIL FERHCRGQTV VLKWISNPLT SPLWVQSCSD DKGAKPKVKP  180
KDDRMKQGKI VTKPKETEAD QKTRPPDATI VVDGQKYQVR KKGKAKPKTQ DGLYHNKNKP  240
EASRKKLEKA LLAWAILACL LVVPVGSTNV TQWNLWDNKS TTDIHSVMFS RGIKRSLHGI  300
WPTQICKGIP THLAADYELK RIHGMVDASP MTNFTCCRLQ RHEWNKHGWC NWYNIEPWIN  360
LMNNTQGLLN TGDNFTECAV TCRYDADLGV NIVTQARTTP TILTGCKKGH NFSFSGEVRA  420
SPCNFELTAE DLLRIMDHTN CEGFTYFGEG IVDGYTEVVE KARSSGFRAL TWLSSKIENT  480
KKKIFGAEAS PYCPVAKRVF NIIYTNNCTP LGLPDKSKII GPGTFDISGR DEFIFPKLPY  540
HVDDFILLSL IAMSDFAPET SSIIYLALHY LMPSNDNRDF VMDLDPNKLN LTATKSVASV  600
VPTSVNVLGE WVCVKPSWWP YSAEITNLIG GVITVADLVI KTIEELLNLW TEATAVAFLA  660
ALIKIFRGQP IQAVAWLIII GGAQAQTCNP EFMYALAKNT SIGSLGPESL TTRWYQLTSG  720
FKLTDSTIEV TCVGANMRIH VVCPLVSDRY LAINHPRALP TTAWFRKIHT QHEVPRERIM  780
SESKRRYTCP CGSKPVVRST TQFNPISIST PSFELECPRG WTGAVECTLV SPSTLTTETI  840
FTYRKPKPFG LENWCKYTVV EKGILYSCKF GGNSTCIKGL IVKGQREDKV RYCEWCGYKF  900
SSPNGLPQYP LGLCEKEQSE GLRDYGDFPC CNNGTCIDKE GSVQCYIGDK KVTVKLYNAS  960
LLAPMPCKPI VYNSQGPPAP KTCTYRWAST LENKYYEPRD SYYQQYIIKS GYQYWFDLTA 1020
KDHVADWITK YFPIIIVALL GGRGTLWVLI AYELLTQYEV VGDENIVAQA EALVIGNILM 1080
SLDLEIISCF LLLLIVVKKQ AVRRTLALLF HWITMNPFQS VMITVVYFVG LVRAEEGTKE 1140
GSTSGPPIHV VAILLFLLYH TVKYKDFNIA MILLITLSLK SSSYIHTSLY EIPLLVAVIS 1200
LTCSIYIFDL QVKSKLVAPT IGIIGVTLAM RVLWLVRQMT IPTPSVSISL IDPKMVIILY 1260
LISLTITVNH NLDLASYCLK LGPFILSFLT MWVDVVILLL MLPWYELVKV YYLKKKKEDV 1320
ETWFQNSGIS TQETSPYGFD FSSPGEGVHT LPMQNKTKFC RTAYMTVLRA LVITAISSVW 1380
KPIILAELLI EAVYWTHIKI AKELAGSSRF VARFIASIIE LNWAMDEKEA SRYKRFYLLS 1440
SKITDLMVKH KIQNETVKSW FEETEIFGIQ KVAMVIRAHS LSLEPNAILC SVCEEKQNQK 1500
AKRPCPKCGS RGTQIKCGLT LAEFEEEHYK KIYILEGQDE TPMRKEERQQ VTYVSRGALF 1560
LRNLPILASK NKYLLVGNLG MELQDLESMG WIIRGPAVCK KIIHHEKCRP SIPDKLMAFF 1620
GIMPRGVTPR APTRFPVSLL KIRRGFETGW AYTHPGGVSS VMHVTAGSDI YVNDSIGRTK 1680
IQCQDKNTTT DECEYGVKTD SGCSDGARCY VINPEATNIA GTKGAMVHLR KAGGEFNCVT 1740
AQGTPAFYNL KNLKGWSGLP IFEAATGRVV GRVKAGKNTD NAPTTIMSGT QVAKPSECDL 1800
ESVVRKLETM NRGEFKQVTL ATGAGKTTML PKLLIESIGR HKRVLVLIPL RAAAEGVYQY 1860
MRTKHPSISF NLRIGDLKEG DMATGITYAS YGYFCQMDMP RLENAMKEYH YIFLDEYHCA 1920
TPEQLAVMSK IHRFGESVRV IAMTATPSGT VSTTGQKFTI EEVVVPEVMK GEDLADDYIE 1980
IAGLKVPKKE LEGNVLTFVP TRKMASETAK KLTTQGYNAG YYFSGEDPSS LRTTTSKSPY 2040
IVVATNAIES GVTLPDLDTV IDTGMKCEKR LRIENKAPYI VTGLKRMAIT TGEQAQRKGR 2100
VGRVKPGRYL RGPENTAGEK DYHYDLLQAQ RYGIQDSINI TKSFREMNYD WALYEEDPLK 2160
IAQLELLNTL LISRDLPVVT KNLMARTTHP EPIQLAYNSL ETPVPVAFPK VKNGEVTDAH 2220
ETYELMTCRK LEKDPPIYLY ATEEEDLVVD ILGLKWPDAT ERAVLEVQDA LGQITGLSAG 2280
ETALLIALLG WVGYEALVKR HVPMVTDIYT LEDEKLEDTT HLQFAPDDLN NSDTIELQDL 2340
SNHQIQQILE GGKEYVGQAY QFLRLQAERA ANSDKGKKAM AAAPLLAHKF LEYLQEHAGD 2400
IKKYGLWGVH TALYNSIKER LGHETAFASL VIKWIAFSSD GVPGMIKQAA VDLVVYYIIN 2460
RPEYQGDKET QNAGRQFVGS LFVSCLAEYT FKNFNKSALE GLIEPALSYL PYASSALKLF 2520
LPTRLESVVI LSTTIYRTYL SIRKGSSQGL AGLAVSSAME IMNQNPISVA IALALGVGAI 2580
AAHNAIESSE AKRTLLMKVF VKNFLDQAAT DELVKENPEK IIMAVFEGIQ TAGNPLRLVY 2640
HLYAMFYKGW TAAEIAEKTA GRNIFVLTIF EGLEMLGLDA DSKWRNLSSN YLIDAVKKII 2700
EKMTKTATSF TYSFLKSLLP APFSCTKSER DPRIGWPQKD YDYLEVRCAC GYNRRAIKRD 2760
SGPVLWETLE ETGPEYCHNR GERGLSNVKT TRCFVQGEEI PPIALRKGVG EMLVKGVSFR 2820
IDFDKDKILS TDKWKVPHRA VTSIFEDWQG IGYREAYLGT KPDYGGLVPR SCVTVTKQGL 2880
TFLKTARGMA FTTDLTIQNI KMLIATCFKN KVKEGEIPAT IEGETWINIP LVNEDTGTIK 2940
PSFGERVIPE PYEEDPLEGP SVIVETGGIA INQIGVNPQS STCGTVFTAV KDLCQTVSNK 3000
AKNIKIGFSE GQYPGPGVAK KTLNQLIQDE DPKPFIFVCG SDKSMSNRAK TARNIKRITT 3060
TTPEKFRDLA KNKKLIIVLL GDRYHEDIEK YADFKGTFLT RQTLEALASA KAVEKDMTKK 3120
EAARVLAMEE KDELELPGWL HTDAPKFLDI TKDNITHHLI GDMQSLRERA GEIGAKATTQ 3180
ITKKGSVYTI NLSTWWESER LASLEPLFRE LLSKCRPVDR ETYKNCHFAT AAQLAGGNWV 3240
PVAPVVHLGE IPVKKKKTLP YEAYKLLKEM VDSEKEFHKP VSREKHQWIL NKVKTGGDLG 3300
LKNLVCPGRV GEPILREKKK FNIYNKRITS TMLSVGIRPE KLPVVRAQTS TKEFHEAIRD 3360
KIDKKANTQT PGLHKELLEI FNSICAIPEL RNTYKEVDWD VLTSGINRKG AAGYFEKMNI 3420
GEIIDSDKKS VEQLIKRMKS GLEFNYYETA IPKNEKRAVV DDWMEGDYVE EKRPRVIQYP 3480
```

```
EAKMRLAITK VMYNWVKQKP IVIPGYEGKT PLFHVFDKVH KEWKNFNSPV AVSFDTKAWD   3540
TQVTPKDLLL ISEIQKYYYK KEYHRFIDNL TEKMVEVPVV CEDGNVYIRE GQRGSGQPDT   3600
SAGNSMLNVL TMIYAFCKAN SIPYSAFHRV AKIHVCGDDG FLITEKSFGE AFAIKGPQIL   3660
MEAGKPQKLI GEFGLKLAYK FDDIEFCSHT PIKVRWADNN TSYMPGRDTA TILAKMATRL   3720
DSSGERGTEG YELAVAFSFL LMYSWNPLVR RICLLVMSTI DTKEASQNNT IYTFRGDPIG   3780
AYTEVIGYRL DQLKQTEFSK LAQLNLSMAI LQIYNKNTTK RLIEDCVKLG NQNKQILVNA   3840
DRLISKKTGY TYEPTAGHTK IGKHYEEINL LKDTPQKTVY QGTERY                 3886
```

Figure 2 (continued)

Figure 6B
41 42 43 44 45 46 47 48 49 50 51 52 53 54 55 56 57 58 59 60 61 62 63 64 65 66 67 68 69 70 71 72 73 74 75 76 77 78 79 80
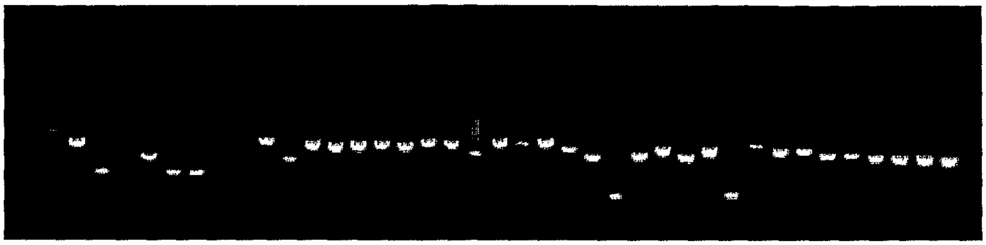
81 82 83 84 85 86 87

Figure 8A
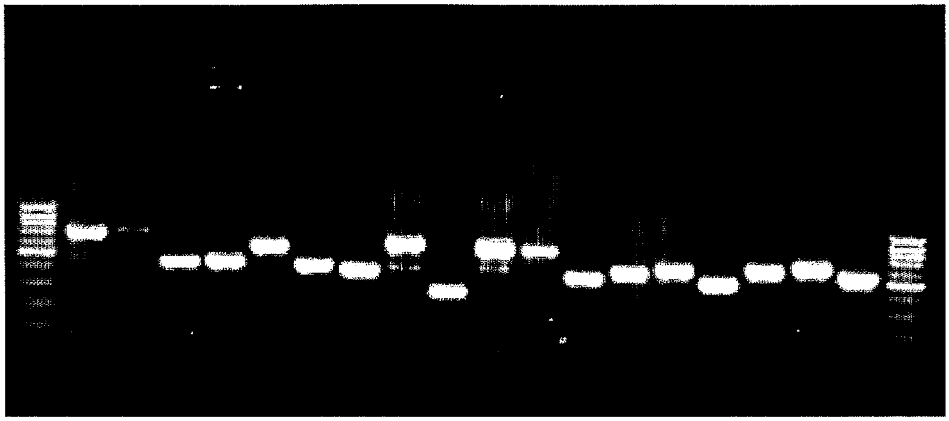
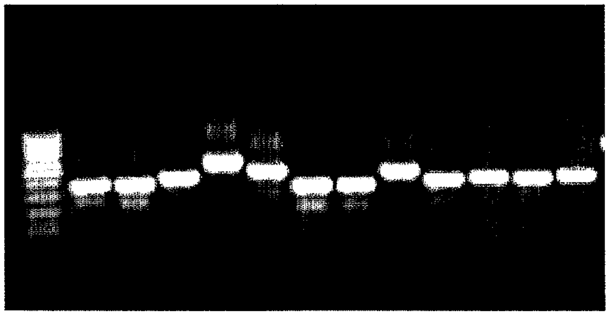

34 35 36 37 38 39 40 41 42 43 44 45 46 47 48 49 50 51 52 53

PESTIVIRUS SPECIES

FIELD OF THE INVENTION

The present invention relates to a novel pestivirus, and gene sequences derived from the same. The invention further relates to detection methods, vaccines, therapeutics, and diagnostic methods using the sequences of the present invention.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 13279926.TXT, the date of creation of the ASCII text file is May 16, 2012, and the size of the ASCII text file is 110 KB.

BACKGROUND ART

Pestiviruses cause highly contagious and often fatal diseases of pigs, cattle and sheep, which are characterised by damage to the respiratory and gastrointestinal tracts and immune system and can run an acute or chronic course. Infection of the reproductive system may cause embryonic and foetal death, congenital defects and the birth of persistently infected animals. Outbreaks of the diseases associated with pestivirus infections occur in many countries and can cause large economic losses.

The Pestivirus genus of the Flaviviridae comprises three structurally, antigenically and genetically closely related member species: Classical swine fever (CSF) or hog cholera (Francki et al. 1991. Flaviviridae, In the Fifth report of the International Committee on Taxonomy of Viruses, Archiv. Virol. Suppl. 2, Springer Verlag, Vienna p. 223-233); Bovine viral diarrhoea virus (BVDV) which mainly affects cattle, and Border disease virus (BDV) which mainly affects sheep (Moennig and Plagemann (1992) Adv. Virus Res. 41: 53-98; Moormann et al., (1990) Virology 177: 184-198; Becher et al. (1994) Virology 198: 542-551). Recent studies indicate that there may be several less well recognised viruses that warrant separate taxonomic classification, perhaps as separate species (Avalos-Ramirez et al (2001) Virology 286: 456-465)

The genomes of pestiviruses consist of a positive strand RNA molecule of about 12.5 kb (Renard et al. (1985) DNA 4: 429-438; Moormann and Hulst (1988) Virus Res. 11: 281-291; Becher et al. (1994) Virology 198: 542-551). However, the positive strand RNA genomes of several cytopathogenic BVDV strains may be considerably larger (Meyers et al. (1991) Virology 180: 602-616; Meyers et al. (1992) Virology 191: 368-386; Qi et al. (1992) Virology 189: 285-292).

An inherent property of viruses with a positive strand RNA genome is that their genomic RNA is infectious, i.e. after transfection of this RNA in cells that support viral replication, infectious virus is produced. As expected, the genomic (viral) RNA of pestiviruses is also infectious (Moennig and Plagemann, (1992) Adv. Virus Res. 41: 53-98).

In 2003 an outbreak of stillbirths and pre-weaning deaths of piglets occurred on two farms in New South Wales, Australia (McOrist et al, (2004) Aust Vet J. 82: 509-511). Key features of the clinical presentation and pathology findings suggested that this disease outbreak was novel and probably due to a virus. Extensive testing for known viruses and some bacteria failed to identify an aetiological agent. To avoid confusion with other important diseases in pigs, the term "porcine myocarditis syndrome" (abbreviated as "PMC") was ascribed to the disease, and the term "PMC virus" given to presumptive agent. Subsequently, the causative agent was identified as a novel pestivirus. The name Bungowannah is proposed for this new virus.

The present invention addresses a need in the art for methods of detecting and/or treating infections caused by the novel PMC virus.

SUMMARY OF THE INVENTION

The invention provides an isolated RNA nucleotide sequence corresponding to the PMC virus nucleotide sequence depicted in SEQ ID NO:1, or sequences substantially homologous to SEQ ID NO:1, or fragments thereof.

The invention also provides the isolated DNA nucleotide sequence of the PMC virus of SEQ ID NO:1, or sequences substantially homologous to SEQ ID NO:1, or fragments thereof.

The invention further provides polypeptides encoded by the above RNA and DNA nucleotide sequences and fragments thereof, and/or an isolated PMC virus amino acid sequence as shown in SEQ ID NO: 2 and fragments thereof.

In another aspect, the invention provides methods for detecting the presence of a PMC virus amino acid sequence in a sample, comprising the steps of:

a) contacting a sample suspected of containing a PMC virus amino acid sequence with an antibody that specifically binds to the PMC virus amino acid sequence under conditions which allow for the formation of reaction complexes comprising the antibody and the PMC virus amino acid sequence; and
b) detecting the formation of reaction complexes comprising the antibody and PMC virus amino acid sequence in the sample, wherein detection of the formation of reaction complexes indicates the presence of PMC virus amino acid sequence in the sample.

The invention also provides methods for detecting the presence of a PMC virus antibody in a sample, comprising the steps of:

a) contacting a sample suspected of containing a PMC virus antibody with an amino acid sequence under conditions which allow for the formation of reaction complexes comprising the PMC virus antibody and the amino acid sequence; and
b) detecting the formation of reaction complexes comprising the antibody and amino acid sequence in the sample, wherein detection of the formation of reaction complexes indicates the presence of PMC virus antibody in the sample.

Additionally, the invention provides an in vitro method for evaluating the level of PMC virus antibodies in a biological sample comprising the steps of:

a) detecting the formation of reaction complexes in a biological sample according to the method noted above; and
b) evaluating the amount of reaction complexes formed, which amount of reaction complexes corresponds to the level of PMC virus antibodies in the biological sample.

The invention also provides an in vitro method for evaluating the level of PMC virus polypeptides in a biological sample comprising the steps of:

a) detecting the formation of reaction complexes in a biological sample according to the method noted above; and
b) evaluating the amount of reaction complexes formed, which amount of reaction complexes corresponds to the level of PMC virus polypeptide in the biological sample.

The present invention further provides methods for detecting the presence or absence of PMC virus in a biological sample, which comprise the steps of:

a) bringing the biological sample into contact with a polynucleotide probe or primer comprising a PMC virus polynucleotide of the invention under suitable hybridising conditions; and
b) detecting any duplex formed between the probe or primer and nucleic acid in the sample.

The present invention also relates to a method for the detection of PMC virus nucleic acids present in a biological sample, comprising:

a) amplifying the nucleic acid with at least one primer as defined above,
b) detecting the amplified nucleic acids.

The present invention also relates to a method for the detection of PMC virus nucleic acids present in a biological sample, comprising:

a) hybridizing the nucleic acids of the biological sample at appropriate conditions with one or more probes as defined above,
b) washing under appropriate conditions, and
c) detecting the hybrids formed.

In a further aspect, the present invention provides a method for the generation of antibodies comprising the steps of:

a) providing a PMC virus polypeptide sequence to a subject; and
b) collecting the antibodies generated in the subject against the polypeptide.

In another aspect of the invention, there is provided a vaccine composition comprising a PMC virus polypeptide or fragment thereof. The invention also provides a vaccine composition comprising a PMC virus nucleotide or fragment thereof that encodes for a PMC virus polypeptide.

Pharmaceutical compositions comprising a PMC virus polypeptide that enhances the immunocompetence of the host individual and elicits specific immunity against the PMC virus are further provided by the invention.

The present invention also provides therapeutic compositions comprising polynucleotide sequences and/or antibodies prepared against the polypeptides of the invention. The present invention further provides therapeutic compositions comprising PMC virus nucleic acid sequences as well as antisense and ribozyme polynucleotide sequences hybridisable to a polynucleotide sequence encoding a PMC virus amino acid sequence according to the invention.

The present invention provides for the use of PMC virus amino acid sequences and/or antibodies according to the invention, for manufacture of a medicament for modulation of a disease associated with PMC virus. The present invention additionally provides for the use of polynucleotide sequences of the invention, as well as antisense and ribozyme polynucleotide sequences hybridisable to a polynucleotide sequence encoding a PMC virus amino acid sequence according to the invention, for manufacture of a medicament for modulation of a disease associated with PMC virus.

The present invention further provides a method of inducing a protective immune response in an animal or human against PMC virus comprising the steps of:

a) administering to said animal or human an effective amount of a composition of the invention.

The present invention also provides methods for enhancing an animal's immunocompetence and the activity of its immune effector cells against a PMC virus comprising the step of:

a) administering a composition comprising a therapeutically effective amount of a PMC virus peptide or polypeptide.

In addition, the present invention provides a live vector comprising the PMC virus and a heterologous polynucleotide.

In another aspect of the invention, there is provided a method of screening for drugs comprising the steps of:

a) contacting an agent with a PMC virus amino acid sequence or fragment thereof and
b) assaying for the presence of a complex between the agent and the PMC virus amino acid sequence or fragment.

The present invention also provides a method of screening for ligands of the proteins of the PMC virus comprising the steps of:

a) contacting a ligand with a PMC virus amino acid sequence or fragment thereof and
b) assaying for the presence of a complex between the PMC virus amino acid sequence or fragment and a ligand.

In a further aspect of the invention, a test kit may be prepared for the demonstration of the presence of PMC virus comprising:

(a) a predetermined amount of at least one labelled immunochemically reactive component obtained by the direct or indirect attachment of the present PMC virus amino acid sequence or a specific binding partner thereto, to a detectable label;
(b) other reagents; and
(c) directions for use of said kit.

Additionally, the invention provides a test kit for the demonstration of the presence of PMC virus comprising:

(a) a predetermined amount of at least one labelled antibody to the PMC virus;
(b) other reagents; and
(c) directions for use of said kit.

The invention also provides a test kit for the demonstration of the presence of PMC virus comprising:

(a) a predetermined amount of at least one labelled polypeptide derived from the PMC virus;
(b) other reagents; and
(c) directions for use of said kit.

Additionally the present invention provides a test kit prepared for the demonstration of the presence of PMC virus comprising:

(a) a predetermined amount of at least one labelled nucleic acid sequence derived from the PMC virus;
(b) other reagents; and
(c) directions for use of said kit.

The present invention also provides a recombinant expression vector comprising a PMC virus nucleic acid sequence or a part thereof as defined above, operably linked to prokaryotic, eukaryotic or viral transcription and translation control elements.

The invention further relates to the hosts (prokaryotic or eukaryotic cells) which are transformed by the above mentioned vectors and recombinants and which are capable of expressing said RNA and/or DNA fragments.

The present invention also relates to a method for the production of a recombinant PMC virus polypeptide, comprising the steps of:

a) transforming an appropriate cellular host with a recombinant vector, in which a PMC virus polynucleotide sequence or a part thereof has been inserted under the control of appropriate regulatory elements,
b) culturing said transformed cellular host under conditions enabling the expression of said insert, and,
c) harvesting said polypeptide.

According to another embodiment the present invention provides methods for preparing a PMC virus amino acid sequence, comprising the steps of:

(a) culturing a cell containing a vector as described above under conditions that provide for expression of the PMC virus amino acid sequence; and (b) recovering the expressed PMC virus sequence.

BRIEF DESCRIPTION OF THE DRAWINGS

FIG. 1 shows the DNA sequence (SEQ ID NO: 1) of the PMC virus of the present invention;

FIG. 2 shows the protein sequence (SEQ ID NO: 2) of the PMC virus of the present invention;

DETAILED DESCRIPTION OF THE INVENTION

New Pestivirus

Figure 3:
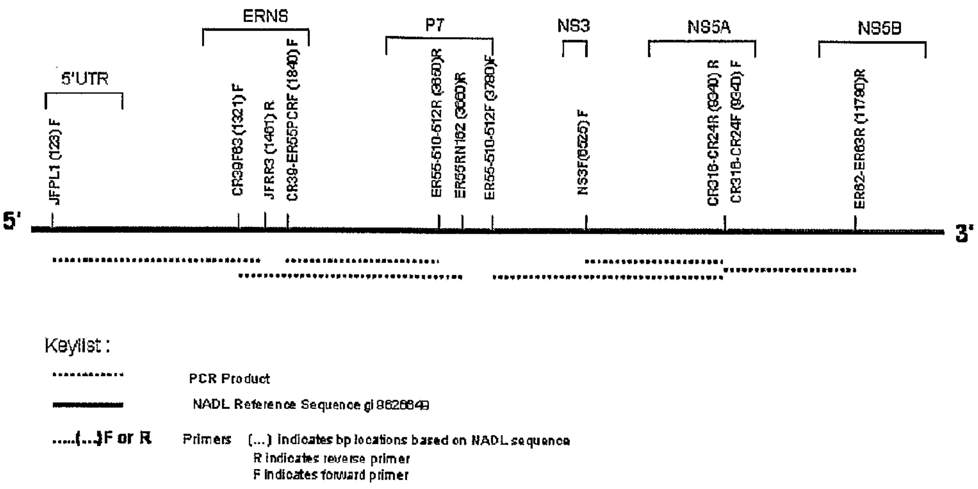
FIG. 3 shows a map of the location of primers used to sequence the whole virus, the dotted lines underneath are the length of the PCR products produced and sequenced.
Figure 4:
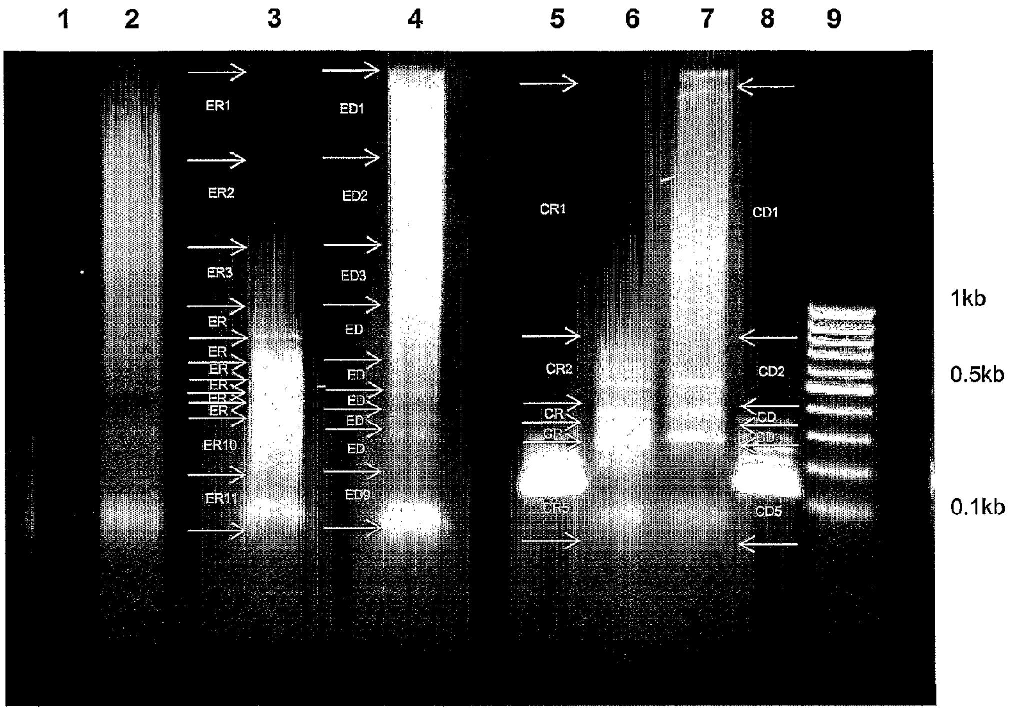
FIG. 4 shows an ethidium bromide stained 0.8% gel of SISPA applied to DNA and RNA of adaptor PCR (run on Corbett and Eppendorf cycler machines). Arrows indicate where gel was cut to collect bands for purification and cloning (e.g. ER1=Eppendorf PCR machine, RNA preparation, gel position 1). Lane 1 Eppendorf machine RNA SISPA 10 ul of PCR product; Lane 2 Eppendorf machine DNA SISPA 10 ul of PCR product; Lane 3 Eppendorf machine RNA SISPA 40 ul of PCR product; Lane 4 Eppendorf machine DNA SISPA 40 ul of PCR product; Lane 5 Eppendorf machine Blank 40 ul of PCR control; Lane 6 Corbett machine RNA SISPA 40 ul of PCR product; Lane 7 Corbett machine DNA SISPA 40 ul of PCR product; Lane 8 Corbett machine blank 40 ul of PCR product; Lane 9 100 bp marker.
Figure 5A:
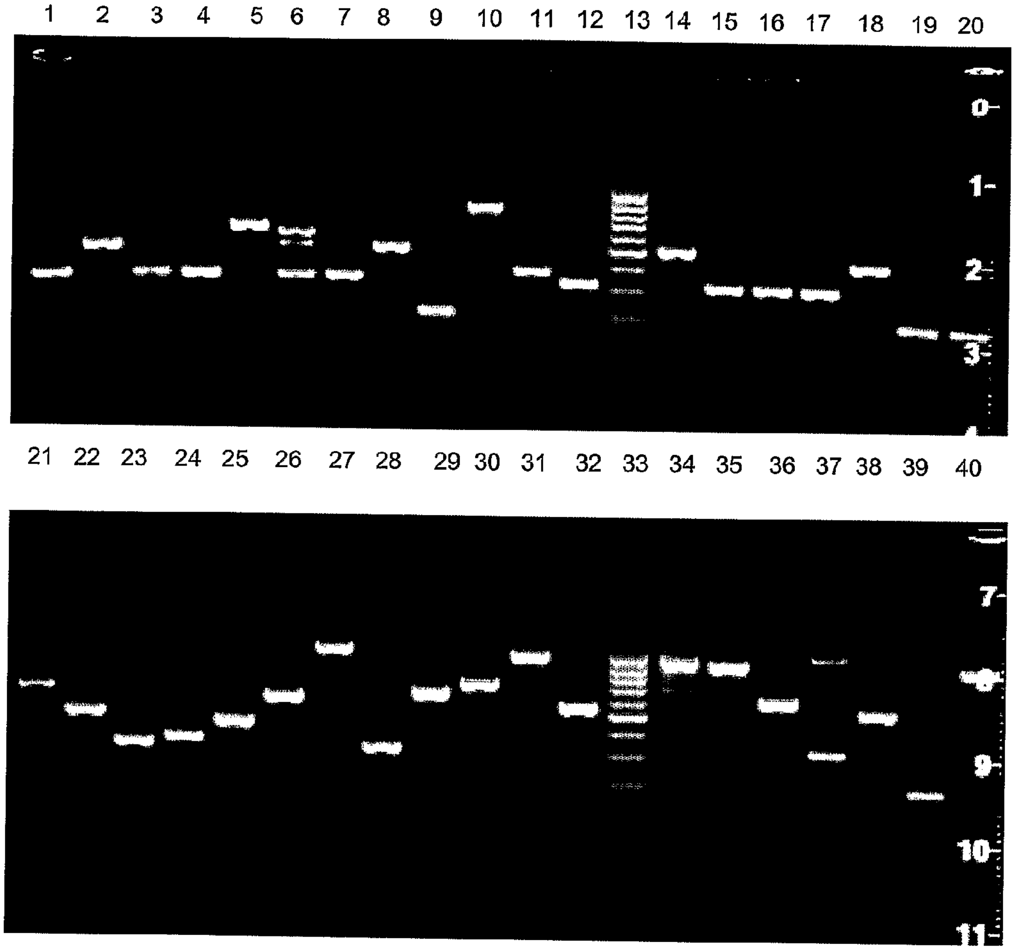
FIG. 5 (A and B) show ethidium bromide stained 1% gels of SISPA applied to DNA and RNA simultaneously to screen colonies for inserts (e.g. ER31=Eppendorf PCR machine, RNA sample position 3 colony 1). Lane 1 ER31; Lane 2 ER32; Lane 3 ER33; Lane 4 ER34; Lane 5 ER35; Lane 6 ER36; Lane 7 ER37; Lane 8 ER38; Lane 9 ER39; Lane 10 ER310; Lane 11 ER311; Lane 12 ER312; Lane 13 Marker 100 bp; Lane 14 ER41; Lane 15 ER42; Lane 16 ER43; Lane 17 ER44; Lane 18 ER45; Lane 19 ER46; Lane 20 ER47; Lane 21 ER48; Lane 22 ER49; Lane 23 ER410; Lane 24 ER411; Lane 25 ER412; Lane 26 ER51; Lane 27 ER52; Lane 28 ER53; Lane 29 ER54; Lane 30 ER55; Lane 31 ER56; Lane 32 ER57; Lane 33 Marker 100 bp; Lane 34 ER58; Lane 35 ER59; Lane 36 ER5 10; Lane 37 ER511; Lane 38 ER512; Lane 39 ER61; Lane 40 ER62; Lane 41 ER63; Lane 42 ER64; Lane 43 ER65; Lane 44 ER66; Lane 45 ER67; Lane 46 ER68; Lane 47 ER69; Lane 48 ER610; Lane 49 ER611; Lane 50 ER612; Lane 51 ER71; Lane 52 ER72; Lane 53 Marker 100 bp; Lane 54 ER73; Lane 55 ER7 4; Lane 56 ER75; Lane 57 ER76; Lane 58 ER77; Lane 59 ER78; Lane 60 ER7 10; Lane 61 ER711; Lane 62 ER712; Lane 63 ER81; Lane 64 ER82; Lane 65 ER8 3; Lane 66 ER84; Lane 67 ER85; Lane 68 ER86; Lane 69 ER87; Lane 70 ER8 8; Lane 71 ER89; Lane 72 ER810; Lane 73 Marker 100 bp; Lane 74 ER8 11; Lane 75 ER812; Lane 76 ER91; Lane 77 ER92; Lane 78 ER93; Lane 79 ER94; Lane 80 ER95; Lane 81 Marker 100 bp; Lane 82 ER96; Lane 83 ER97; Lane 84 ER98; Lane 85 ER99; Lane 86 ER910; Lane 87 ER911; Lane 88; Lane 89 ER10 2; Lane 90 ER10 3; Lane 91 ER10 4; Lane 92 ER10 5; Lane 93 ER10 6; Lane 94 ER10 7; Lane 95 ER10 8; Lane 96 ER10 9; Lane 97 ER10 10; Lane 98 ER10 11; Lane 99 ER10 12.
Figure 5B:
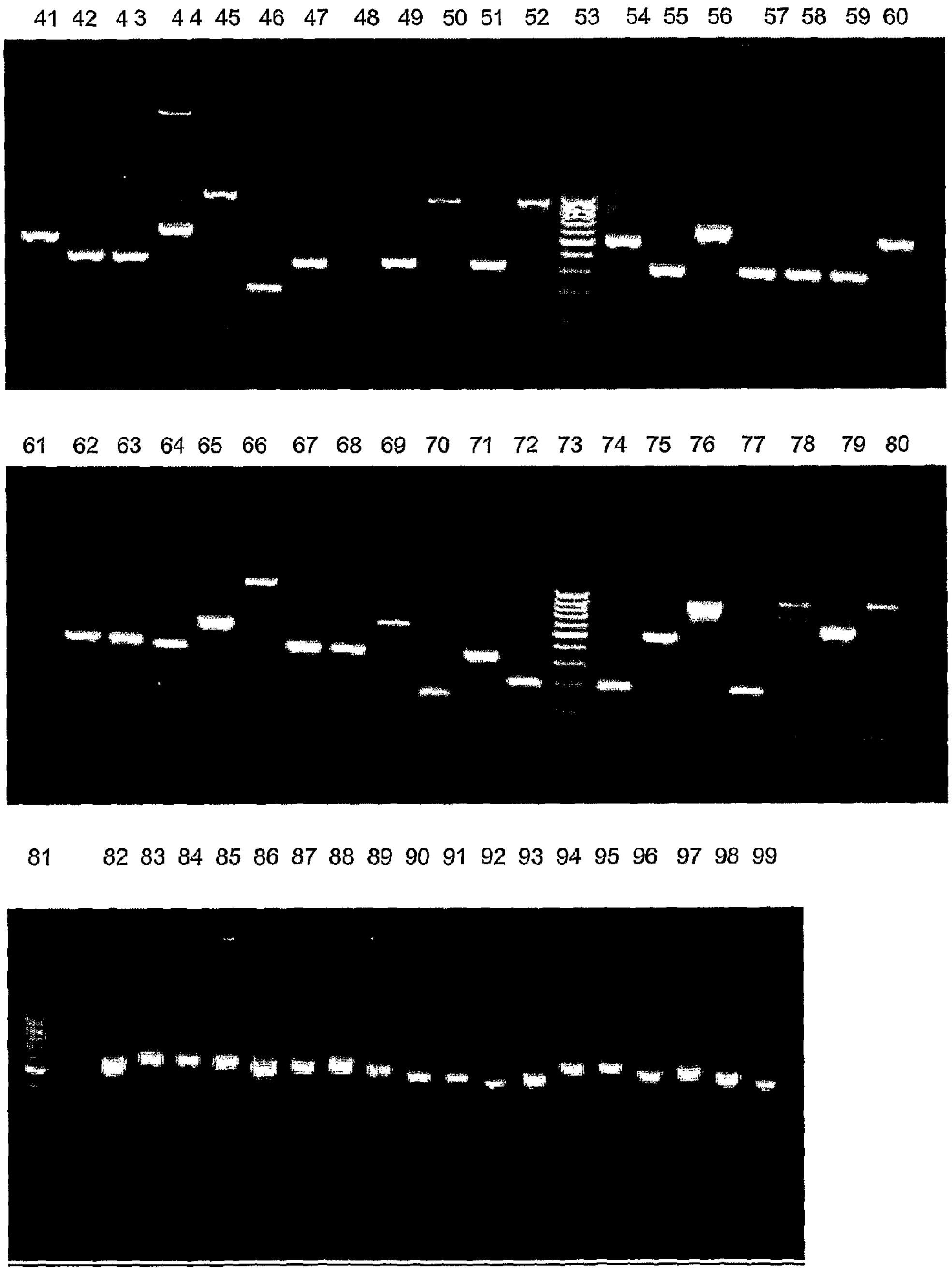
Figure 6A:
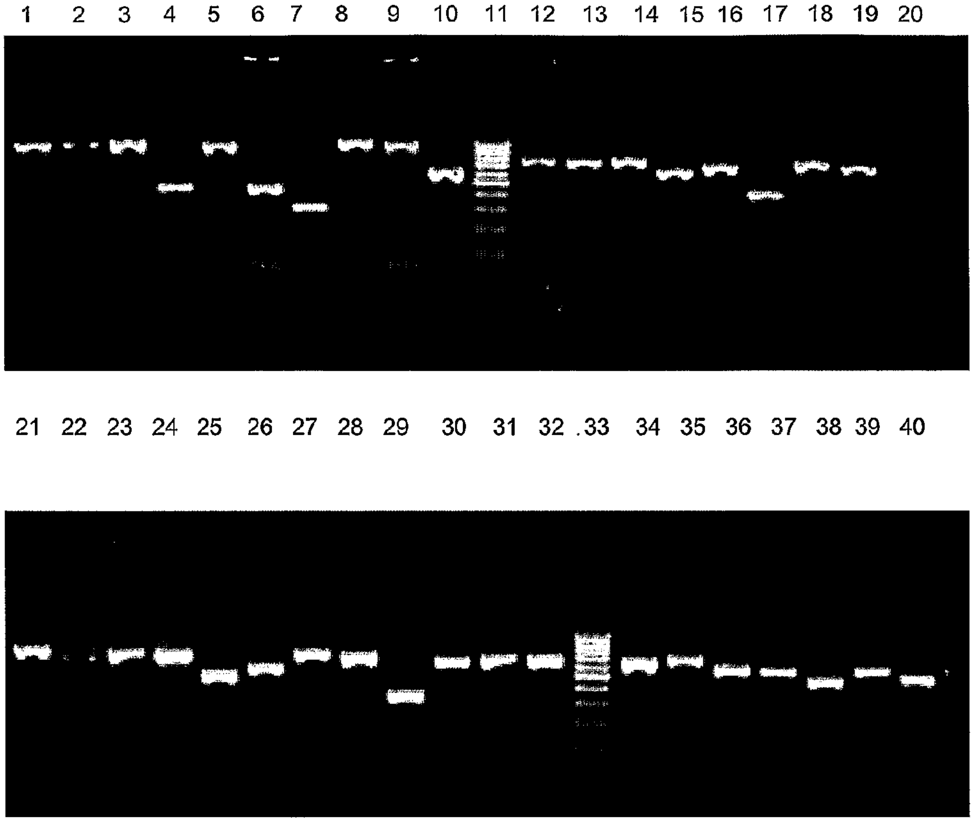
FIG. 6 (A and B) show ethidium bromide stained 1% gels of PCR carried out to screen of colonies for DNA (Eppendorf cycler). Lane 1 ED2 1=Eppendorf machine, DNA gel cut out 2, colony 1; Lane 2 ED2 2; Lane 3 ED2 3; Lane 4 ED2 4; Lane 5 ED2 5; Lane 6 ED2 6; Lane 7 ED2 7; Lane 8 ED2 8; Lane 9 ED2 9; Lane 10 ED2 10; Lane 11 ED2 11; Lane 12 ED2 12; Lane 13 Marker 100 bp; Lane 14 ED3 1; Lane 15 ED3 2; Lane 16 ED3 3; Lane 17 ED3 4; Lane 18 ED3 5; Lane 19 ED3 6; Lane 20 ED3 7; Lane 21 ED3 8; Lane 22 ED3 9; Lane 23 ED3 10; Lane 24 ED3 11; Lane 25 ED3 12; Lane 26 ED4 1; Lane 27 ED4 2; Lane 28 ED4 3; Lane 29 ED4 4; Lane 30 ED4 5; Lane 31 ED4 6; Lane 32 ED4 7; Lane 33 Marker 100 bp; Lane 34 ED4 8; Lane 35 ED4 9; Lane 36 ED4 10; Lane 37 ED4 11; Lane 38 ED4 12; Lane 39 ED5 1; Lane 40 ED5 2; Lane 41 ED5 3; Lane 42 ED5 4; Lane 43 ED5 5; Lane 44 ED5 6; Lane 45 ED5 7; Lane 46 ED5 8; Lane 47 ED5 9; Lane 48 ED5 10; Lane 49 ED5 11; Lane 50 ED5 12; Lane 51 ED6 1; Lane 52 ED6 2; Lane 53 ED6 3; Lane 54 ED6 4; Lane 55 ED6 5; Lane 56 ED6 6; Lane 57 ED6 7; Lane 58 ED6 8; Lane 59 ED6 9; Lane 60 Marker 100 bp; Lane 61 ED6 10; Lane 62 ED6 11; Lane 63 ED6 12; Lane 64 ED7 1; Lane 65 ED7 2; Lane 66 ED7 3; Lane 67 ED7 4; Lane 68 ED7 5; Lane 69 ED7 6; Lane 70 ED7 7; Lane 71 ED7 8; Lane 72 ED7 9; Lane 73 ED7 10; Lane 74 ED7 11; Lane 75 ED7 12; Lane 76 ED8 1; Lane 77 ED8 2; Lane 78 ED8 3; Lane 79 ED8 4; Lane 80 ED8 5; Lane 81 ED8 6; Lane 82 ED8 7; Lane 83 ED8 8; Lane 84 ED8 9; Lane 85 ED8 10; Lane 86 ED8 11; Lane 87 ED8 12.
Figure 7A:
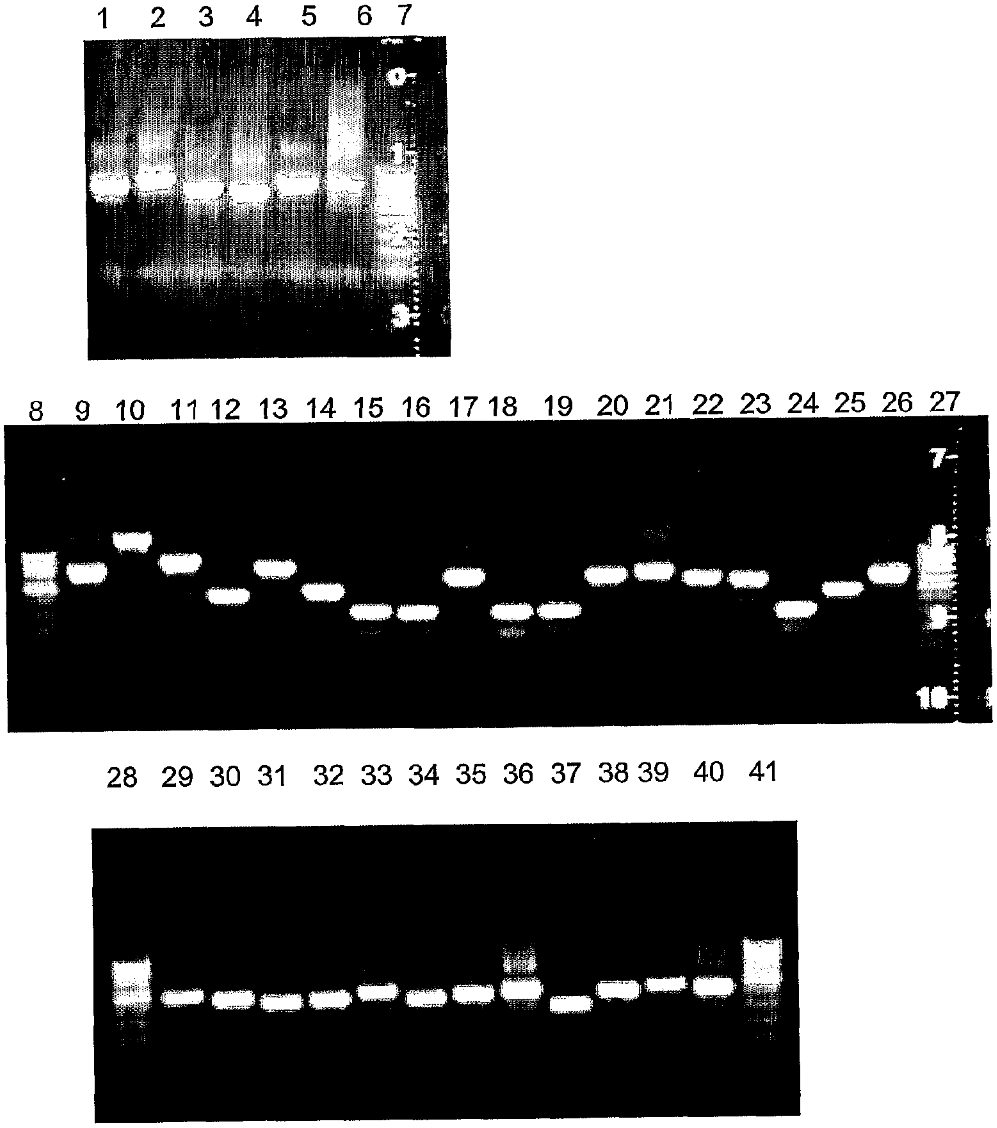
FIG. 7 (A and B) show ethidium bromide stained 1% gels of PCR carried out to screen of colonies for RNA inserts (Corbett cycler). Lane 1 CR2 1=Corbett machine, RNA gel position 2, colony 1; Lane 2 CR2 2; Lane 3 CR2 3; Lane 4 CR2 4; Lane 5 CR2 5; Lane 6 CR2 6; Lane 7 Marker 100 bp; Lane 8 Marker 100 bp; Lane 9 CR2 7; Lane 10 CR2 8; Lane 11 CR2 9; Lane 12 CR2 10; Lane 13 CR2 11; Lane 14 CR2 12; Lane 15 CR3 1; Lane 16 CR3 2; Lane 17 CR3 3; Lane 18 CR3 4; Lane 19 CR3 5; Lane 20 CR3 6; Lane 21 CR3 7; Lane 22 CR3 8; Lane 23 CR3 9; Lane 24 CR3 10; Lane 25 CR3 11; Lane 26 CR3 12; Lane 27 Marker 100 bp; Lane 28 Marker 100 bp; Lane 29 CR4 1; Lane 30 CR4 2; Lane 31 CR4 3; Lane 32 CR4 4; Lane 33 CR4 5; Lane 34 CR4 6; Lane 35 CR4 7; Lane 36 CR4 8; Lane 37; CR4 9; Lane 38 CR4 10; Lane 39 CR4 11; Lane 40 CR4 12; Lane 41 marker 100 bp; Lane 42 marker 100 bp; Lane 43 CR5 1; Lane 44 CR5 2; Lane 45 CR5 3; Lane 46 CR5 4; Lane 47 CR5 5; Lane 48 CR5 6; Lane 49 CR5 7; Lane 50 CR5 8; Lane 51 CR5 9; Lane 52 CR5 10; Lane 53 CR5 11; Lane 54 PCR Blank control; Lane 55 marker 100 bp.
Figure 7B:
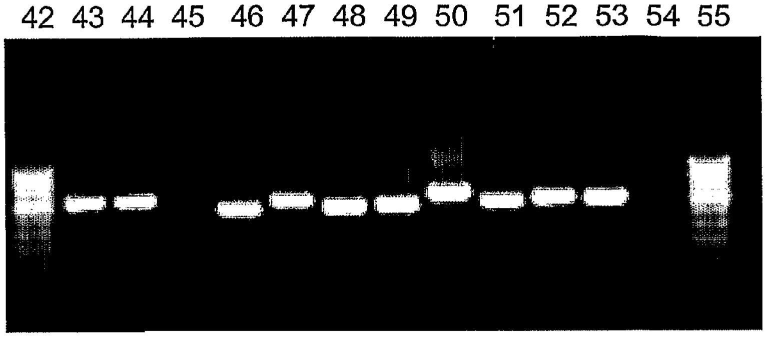
Figure 8B:
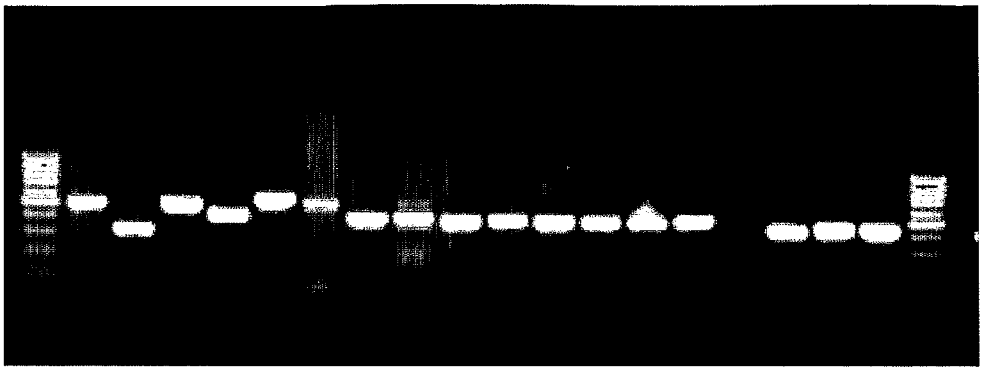
FIG. 8 (A and B) show ethidium bromide stained 1% gels of PCR carried out to screen colonies for DNA (Corbett cycler). Lane 1 marker 100 bp; Lane 2 CD3 1=Corbett machine, DNA gel cut out 3, colony 1; Lane 3 CD3 2; Lane 4 CD3 3; Lane 5 CD3 4; Lane 6 CD3 5; Lane 7 CD3 6; Lane 8 CD3 7; Lane 9 CD3 8; Lane 10 CD3 9; Lane 11 CD3 10; Lane 12 CD3 11; Lane 13 CD3 12; Lane 14 CD4 1; Lane 15 CD4 2; Lane 16 CD4 3; Lane 17 CD4 4; Lane 18 CD4 5; Lane 19 CD4 6; Lane 20 marker 100 bp; Lane 21 marker 100 bp; Lane 22 CD4 7; Lane 23 CD4 8; Lane 24 CD4 9; Lane 25 CD4 10; Lane 26 CD4 11; Lane 27 CD4 12; Lane 28 CD5 1; Lane 29 CD5 2; Lane 30 CD5 3; Lane 31 CD5 4; Lane 32 CD5 5; Lane 33 CD5 6; Lane 34 CD5 7; Lane 35 CD5 8; Lane 36 CD5 9; Lane 37 CD5 10; Lane 38 CD5 11; Lane 39 CD5 12; Lane 40 marker 100 bp; Lane 41 marker 100 bp; Lane 42 CD6 1; Lane 43 CD6 2; Lane 44 CD6 3; Lane 45 CD6 4; Lane 46 CD6 5; Lane 47 CD6 6; Lane 48 CD6 7; Lane 49 CD6 8; Lane 50 CD6 9; Lane 51 CD6 10; Lane 52 CD6 11; Lane 53 CD6 12.
Figure 9:
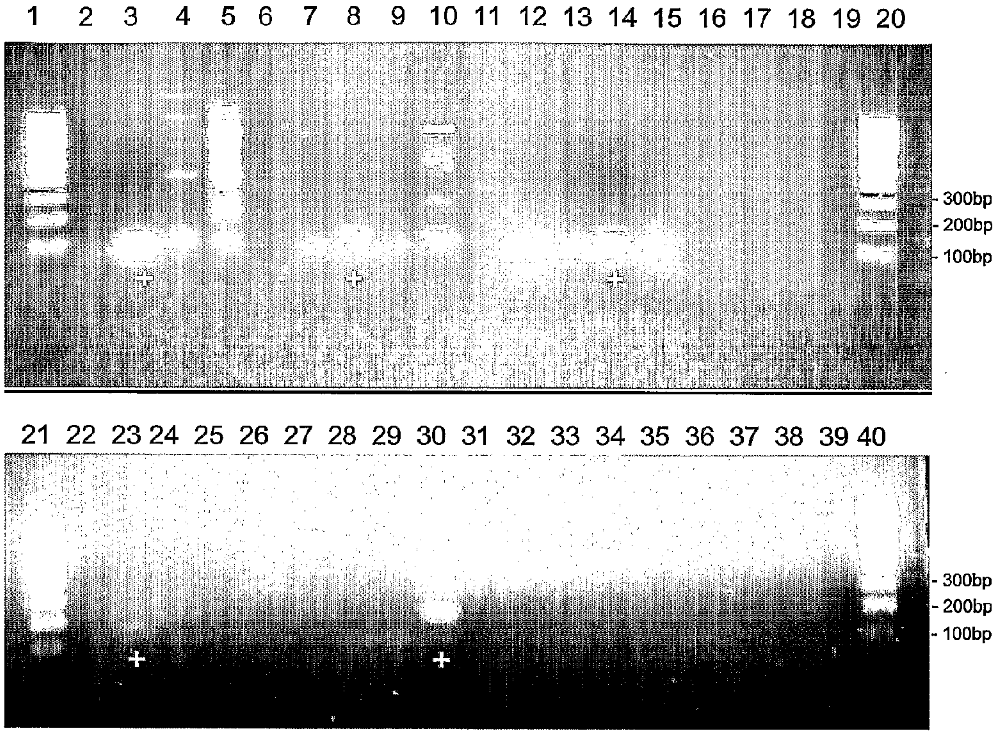
FIG. 9 shows an ethidium bromide stained 1.5% gel of PCR carried out to confirm authenticity of viral sequence for virus confirmation by nRT-PCR. PCR results confirmed the presence of Pestivirus in clinical specimens (lanes 3, 8 and 23) while EMCV was not present (lane 28) (lanes marked + are PCR positive). Lane 1 Marker 100 bp; Lane 2 Blank CR39 primers; Lane 3 SISPA sera CR39 primers; Lane 4 NADL +ve control CR39 primers; Lane 5 EMCV −ve control CR39 primers; Lane 6; Lane 7 Blank ER510 primers; Lane 8 SISPA sera ER510 primers; Lane 9 NADL +ve control ER510 primers; Lane 10 EMCV −ve control ER510 primers; Lane 11; Lane 12 Blank ER55 primers; Lane 13 SISPA sera ER55 primers; Lane 14 NADL +ve control ER55 primers; Lane 15 EMCV −ve control ER55 primers; Lane 16; Lane 17; Lane 18; Lane 19; Lane 20 Marker 100 bp; Lane 21 Marker 100 bp; Lane 22 Blank ER62 primers; Lane 23 SISPA sera ER62 primers; Lane 24 NADL +ve control ER62 primers; Lane 25 EMCV −ve control ER62 primers; Lane 26; Lane 27 Blank ER41 primers; Lane 28 SISPA sera ER41 primers; Lane 29 NADL +ve control ER41 primers; Lane 30 EMCV −ve control ER41 primers; Lane 31; Lane 32; Lane 33; Lane 34; Lane 35; Lane 36; Lane 37; Lane 38; Lane 39; Lane 40 marker 100 bp.
Figure 10:
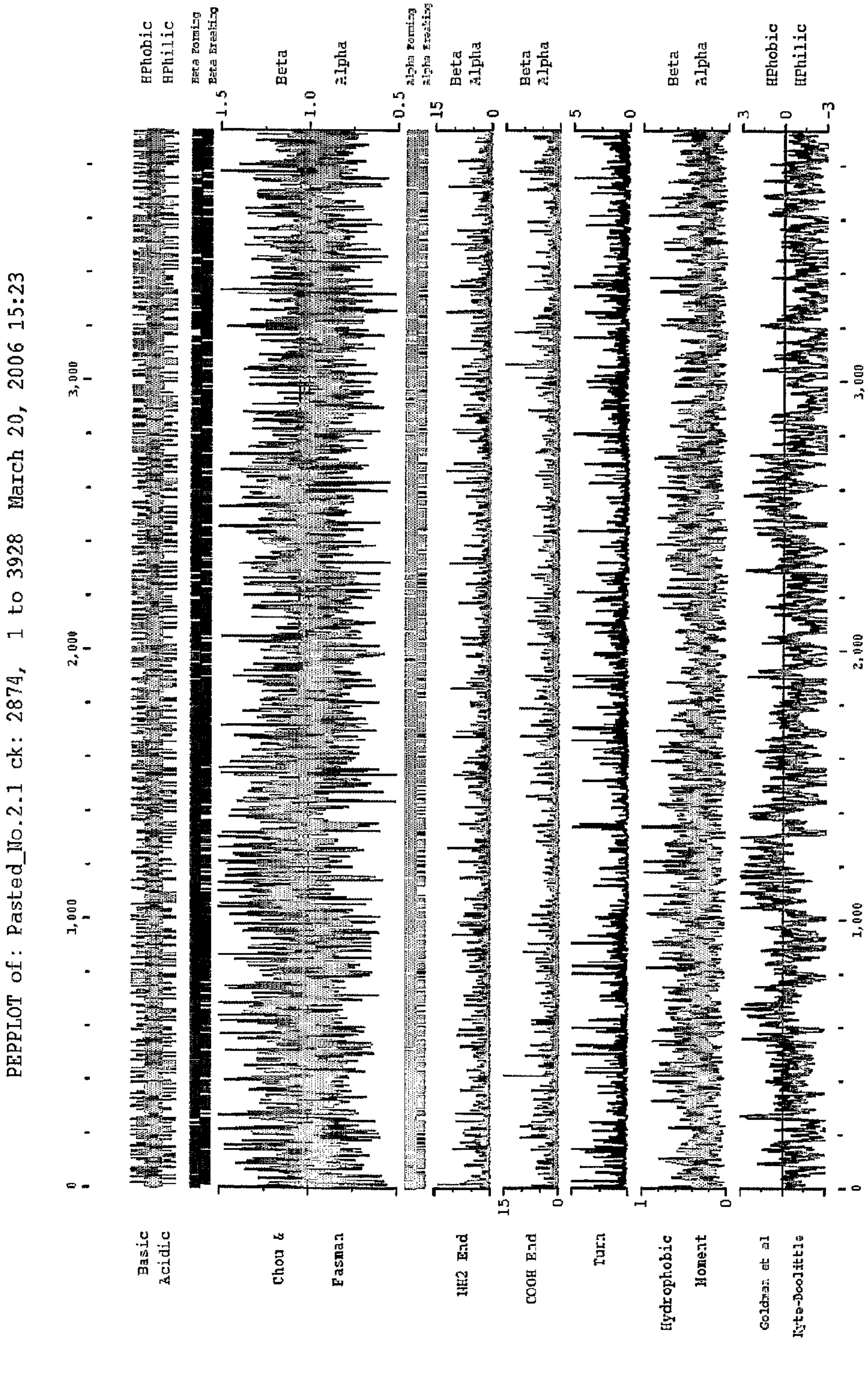
FIG. 10 shows a hydrophobicity plot of the PMC virus protein sequence.

In accordance with this invention, a new pestivirus has been discovered that differs genetically from known pestiviruses. The new virus is characterised by the RNA sequence corresponding to that shown in SEQ ID NO: 1. The sequence has been deposited as Genbank reference EF100713.

The new virus is hereinafter generally referred to as PMC virus and the condition caused by infection with the PMC virus is PMC.

The PMC virus genome comprises a single open reading frame (ORF), encoding a number of genes. The genes encoded by the ORF of PMC correspond to those of other pestiviruses, being the Npro, capsid, E0, E1, E2, P7, NS2, NS3, NS4A, NS4B, NS5A and NS5B genes.

The PMC virus is approximately 40% similar to other pestiviruses on a nucleic acid sequence level. At the protein level, PMC virus has 46-71% identity and 63-83% similarity with other pestiviruses. A comparative analysis of both the nucleic acid and deduced amino acid sequences would suggest that PMC virus is sufficiently unique to warrant consideration for classification as a new species within the pestivirus genus.

Open Reading Frames, Encoded Genes, Features of RNA Genomes

The nucleotide sequence of SEQ ID NO:1 encodes a single ORF encoding a number of different genes. The genes encoded by SEQ ID NO:1 correspond to the Npro, capsid, E0, E1, E2, P7, NS2, NS3, NS4A, NS4B, NS5A and NS5B genes of other pestiviruses.

The approximate location of the genes of PMC, based on sequence comparison with gi12657941, is indicated in Table 1.

TABLE 1

Location of proteins within PMC nucleic acid open-reading frame.

| PROTEIN | APPROXIMATE DNA POSITION |
|---|---|
| NPro | 419-922 |
| Capsid | 923-1219 |
| E0 | 1220-1885 |
| E1 | 1886-2473 |
| E2 | 2474-3604 |
| P7 | 3605-3820 |
| NS2 | 3821-5224 |
| NS3 | 5225-7252 |
| NS4A | 7253-7441 |
| NS4B | 7442-8482 |
| NS5A | 8483-9997 |
| NS5B | 9998-12077 |

TABLE 2

Location of proteins within PMC protein open-reading frame.

| PROTEIN | APPROXIMATE AMINO ACID POSITION |
|---|---|
| NPro | 1-167 |
| Capsid | 168-267 |
| E0 | 268-489 |
| E1 | 490-685 |
| E2 | 686-1062 |
| P7 | 1063-1134 |
| NS2 | 1135-1602 |
| NS3 | 1603-2278 |
| NS4A | 2279-2341 |
| NS4B | 2342-2688 |
| NS5A | 2689-3193 |
| NS5B | 3194-3886 |

Nucleic Acid Sequences

RNA

The invention provides an isolated RNA nucleotide sequence corresponding to the PMC virus nucleotide sequence depicted in SEQ ID NO:1, or sequences substantially homologous to SEQ ID NO:1, or fragments thereof. The invention further provides an RNA sequence comprising the complement of the PMC virus RNA genome, or fragments thereof.

The RNA sequence may also correspond to a fragment of SEQ ID NO:1. Preferably, the fragment is selected from the following locations of SEQ ID NO:1: position 419-922, 923-1219, 1220-1885, 1886-2473, 2474-3604, 3605-3820, 3821-5224, 5225-7252, 7253-7441, 7442-8482, 8483-9997, 9998-12077. Alternatively, the fragment may be selected from any one of SEQ ID NOs:3-15.

Substantial homology or identity exists when a PMC virus polynucleotide sequence or fragment thereof will hybridise to another PMC virus polynucleotide (or a complementary strand thereof) under selective hybridisation conditions.

Selective hybridisation may be under low, moderate or high stringency conditions, but is preferably under high stringency.

Typically, selective hybridisation will occur when there is at least about 55% identity over a stretch of at least about 14 nucleotides, preferably at least about 65%, more preferably at least about 75% and most preferably at least about 90%. The length of homology comparison, as described, may be over longer stretches and in certain embodiments will often be over a stretch of at least about nine nucleotides, usually at least about 20 nucleotides, more usually at least about 24 nucleotides, typically at least about 28 nucleotides, more typically at least about 32 nucleotides and preferably at least about 36 or more nucleotides.

Thus, the polynucleotide sequences of the invention preferably have at least 75%, more preferably at least 85%, more preferably at least 90% homology to the sequences shown in the sequence listings herein. More preferably there is at least 95%, more preferably at least 98%, homology. Nucleotide homology comparisons may be conducted as described below for polypeptides. A preferred sequence comparison program is the GCG Wisconsin Bestfit program.

In the context of the present invention, a homologous sequence is taken to include a nucleotide sequence which is at least 60, 70, 80 or 90% identical, preferably at least 95 or 98% identical at the nucleic acid level over at least 20, 50, 100, 200, 300, 500 or 819 nucleotides with the corresponding nucleotide sequences set out in SEQ ID NO:1. In particular, homology should typically be considered with respect to those regions of the sequence that encode contiguous amino acid sequences known to be essential for the function of one or more of PMC virus proteins, rather than non-essential neighbouring sequences.

PMC virus polynucleotide sequence fragments of the invention will preferably be at least 15 nucleotides in length, more preferably at least 20, 30, 40, 50, 100 or 200 nucleotides in length. Generally, the shorter the length of the polynucleotide sequence, the greater the homology required to obtain selective hybridisation. Consequently, where a polynucleotide sequence of the invention consists of less than about 30 nucleotides, it is preferred that the percentage identity is greater than 75%, preferably greater than 90% or 95% compared with the polynucleotide sequences set out in the sequence listings herein. Conversely, where a polynucleotide sequence of the invention consists of, for example, greater than 50 or 100 nucleotides, the percentage identity compared with the polynucleotide sequences set out in the sequence listings herein may be lower, for example greater than 50%, preferably greater than 60 or 75%.

Nucleic acid sequences according to the present invention which are homologous to the sequences as represented by a SEQ ID NO: 1 can be characterized and isolated according to any of the techniques known in the art, such as amplification by means of sequence-specific primers, hybridization with sequence-specific probes under more or less stringent conditions, serological screening methods or via the LiPA typing system.

DNA

The DNA of the new PMC virus also is provided. The DNA sequence is preferably derived from the RNA sequences described above. Most preferably, the DNA sequence is that shown in SEQ ID NO: 1 or fragments thereof.

The invention also provides DNA fragments hybridisable with the genomic RNA of PMC. The DNA or DNA fragment sequence may be derived from the cDNA sequence of the PMC virus or fragments thereof. The DNA, cDNA or fragments thereof may be in the form of recombinant DNAs.

The DNA sequence may also be a fragment of SEQ ID NO:1. Preferably, the fragment is selected from the following locations of SEQ ID NO:1: position 419-922, 923-1219, 1220-1885, 1886-2473, 2474-3604, 3605-3820, 3821-5224, 5225-7252, 7253-7441, 7442-8482, 8483-9997, 9998-12077.

Variant Nucleic Acids

Nucleic acid sequences and fragments, which would include some deletions or mutations which would not substantially alter their ability to hybridizing with the genome of PMC virus, are also provided by the present invention. Such variants are to be considered as forming obvious equivalents of the RNA, DNA or fragments referred to above.

Other preferred variant nucleic acid sequences of the present invention include sequences which are redundant as a result of the degeneracy of the genetic code compared to any of the above-given nucleic acid sequences of the present invention. These variant nucleic acid sequences will thus encode the same amino acid sequences as the nucleic acid sequences they are derived from. Preferably, the RNAs of these variants, and the related cDNAs derived from said RNAs, are hybridisable to corresponding parts of the RNA and cDNA of PMC virus.

Also included within the present invention are sequence variants of the DNA sequence of SEQ ID NO: 1 or corresponding RNA sequence or fragments thereof, containing either deletions and/or insertions of one or more nucleotides, especially insertions or deletions of 1 or more codons.

Also included are substitutions of some non-essential nucleotides by others (including modified nucleotides and/or inosine).

Particularly preferred variant polynucleotides of the present invention also include sequences which hybridise under stringent conditions with any of the nucleic acid sequences of the present invention. Thus, sequences which show a high degree of homology (similarity) to any of the nucleic acid sequences of the invention as described above are preferred. Particularly preferred are sequences which are at least 80%, 85%, 90%, 95% or more homologous to said nucleic acid sequences of the invention. Preferably, said sequences will have less than 20%, 15%, 10%, or 5% variation of the original nucleotides of said nucleic acid sequences.

Probes and Primers

Primer and probes are further provided, which can be made starting from any RNA or DNA sequence or sequence fragment according to the invention. Preferably, such probes or primers are between about 5 to 50 nucleotides long, more preferably from about 10 to 25 nucleotides. Probes and primers of the present invention may be used in PCR, sequencing reactions, hybridisation reactions and other applications known to the skilled person.

The present invention also relates to an oligonucleotide primer comprising part of SEQ ID NO: 1, said primer being able to act as a primer for specifically amplifying the nucleic acid of the PMC virus. Preferably, the primer is a single stranded DNA oligonucleotide sequence capable of acting as a point of initiation for synthesis of a primer extension product which is complementary to the nucleic acid strand to be copied. The specific length and sequence of the primer used will depend on the complexity of the required DNA or RNA targets, as well as on the conditions of primer use, such as temperature and ionic strength. The fact that amplification primers do not have to match exactly with corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules using primer extension. During amplification, the amplified products can be conveniently labelled either using labelled primers or by incorporating labelled nucleotides. Labels may be isotopic ($^{32}P$, $^{35}S$, etc.) or non-isotopic (biotin, digoxigenin, etc.). The amplification reaction is repeated between 20 and 70 times, advantageously between 25 and 45 times.

The present invention also relates to an oligonucleotide probe comprising part of SEQ ID NO:1, with said probe being able to act as a hybridisation probe for the PMC virus. Preferably, the probe can be used for specific detection and/or classification into types and/or subtypes of PMC virus. Preferably, the probe is a single stranded sequence-specific oligonucleotide sequence which has a sequence that is complementary to the target sequence of the PMC virus to be detected.

Those skilled in the art will recognise that the stringency of hybridisation will be affected by such conditions as salt concentration, temperature, or organic solvents, in addition to the base composition, length of the complementary strands and the number of nucleotide base mismatches between the hybridising nucleic acids. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. An example of stringent hybridisation conditions is 65° C. and 0.1×SSC (1×SSC=0.15 M NaCl, 0.015 M sodium citrate pH 7.0).

Optionally, the probe of the invention is labelled and/or attached to a solid substrate. The solid substrate can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin or haptens.

The probes of the invention may include also an isolated polynucleotide attached to a label or reporter molecule and may be used to isolate other polynucleotide sequences, having sequence similarity by standard methods. For techniques for preparing and labelling probes see, e.g. Sambrook et al., (1989) or Ausubel et al., (2001).

Oligonucleotides according to the present invention and used as primers or probes may also contain or consist of nucleotide analogues such as phosphorothioates (Matsukura et al., 1987), alkylphosphoriates (Miller et al., 1979) or peptide nucleic acids (Nielsen et al., 1991; Nielsen et al., 1993) or may contain interculating agents (Asseline et al., 1984). The introduction of these modifications may be advantageous in order to positively influence characteristics such as hybridization kinetics, reversibility of the hybrid-formation, biological stability of the oligonucleotide molecules, etc.

Recombinant DNAs containing fragments of the DNA sequence of PMC virus are also provided by the present invention, and may be used as, for example, probes. Preferably, the plasmid used to generate the recombinant DNA is a plasmid amplifiable in prokaryotic or eukaryotic cells and carrying said fragments. For example, using cloned DNA containing a DNA fragment of PMC virus as a molecular hybridization probe, either by marking with radionucleotides or with fluorescent reagents, PMC virus RNA may be detected directly, for example, in blood, body fluids and blood products.

Nucleic Acid Arrays

PMC virus polynucleotide sequences (preferably in the form of probes) may also be immobilised to a solid phase support for the detection of PMC virus. Alternatively the PMC virus polynucleotide sequences will form part of a library of DNA molecules that may be used to detect simultaneously a number of different genes from PMC virus. In a further alternate form of the invention, PMC virus polynucleotide sequences together with other polynucleotide sequences (such as from other bacteria or viruses) may be immobilised on a solid support in such a manner permitting identification of the presence of PMC virus and/or any of the other polynucleotide sequences bound onto the solid support.

Techniques for producing immobilised libraries of DNA molecules have been described in the art. Generally, most prior art methods describe the synthesis of single-stranded nucleic acid molecule libraries, using for example masking techniques to build up various permutations of sequences at the various discrete positions on the solid substrate. U.S. Pat. No. 5,837,832 describes an improved method for producing DNA arrays immobilised to silicon substrates based on very large scale integration technology. In particular, U.S. Pat. No. 5,837,832 describes a strategy called "tiling" to synthesize specific sets of probes at spatially defined locations on a substrate that may be used to produce the immobilised DNA libraries of the present invention. U.S. Pat. No. 5,837,832 also provides references for earlier techniques that may also be used. Thus polynucleotide sequence probes may be synthesised in situ on the surface of the substrate.

Alternatively, single-stranded molecules may be synthesised off the solid substrate and each pre-formed sequence applied to a discrete position on the solid substrate. For example, polynucleotide sequences may be printed directly onto the substrate using robotic devices equipped with either pins or pizo electric devices.

The library sequences are typically immobilised onto or in discrete regions of a solid substrate. The substrate may be porous to allow immobilisation within the substrate or substantially non-porous, in which case the library sequences are typically immobilised on the surface of the substrate. The solid substrate may be made of any material to which polypeptides can bind, either directly or indirectly. Examples of suitable solid substrates include flat glass, silicon wafers, mica, ceramics and organic polymers such as plastics, including polystyrene and polymethacrylate. It may also be possible to use semi-permeable membranes such as nitrocellulose or nylon membranes, which are widely available. The semi-permeable membranes may be mounted on a more robust solid surface such as glass. The surfaces may optionally be coated with a layer of metal, such as gold, platinum or other transition metal. A particular example of a suitable solid substrate is the commercially available BiaCore™ chip (Pharmacia Biosensors).

Preferably, the solid substrate is generally a material having a rigid or semi-rigid surface. In preferred embodiments, at least one surface of the substrate will be substantially flat, although in some embodiments it may be desirable to physically separate regions for different polymers with, for example, raised regions or etched trenches. It is also preferred that the solid substrate is suitable for the high density application of DNA sequences in discrete areas of typically from 50 to 100 μm, giving a density of 10000 to 40000 dots/$cm^{-2}$.

The solid substrate is conveniently divided up into sections. This may be achieved by techniques such as photoetching, or by the application of hydrophobic inks, for example teflon-based inks (Cel-line, USA).

Discrete positions, in which each different member of the library is located may have any convenient shape, e.g., circular, rectangular, elliptical, wedge-shaped, etc.

Attachment of the polynucleotide sequences to the substrate may be by covalent or non-covalent means. The polynucleotide sequences may be attached to the substrate via a layer of molecules to which the library sequences bind. For example, the polynucleotide sequences may be labelled with biotin and the substrate coated with avidin and/or streptavidin. A convenient feature of using biotinylated polynucleotide sequences is that the efficiency of coupling to the solid substrate can be determined easily. Since the polynucleotide sequences may bind only poorly to some solid substrates, it is often necessary to provide a chemical interface between the solid substrate (such as in the case of glass) and the nucleic acid sequences. Examples of suitable chemical interfaces include hexaethylene glycol. Another example is the use of polylysine coated glass, the polylysine then being chemically modified using standard procedures to introduce an affinity ligand. Other methods for attaching molecules to the surfaces of solid substrate by the use of coupling agents are known in the art, see for example WO98/49557.

Binding of complementary polynucleotide sequences to the immobilised nucleic acid library may be determined by a variety of means such as changes in the optical characteristics of the bound polynucleotide sequence (i.e. by the use of ethidium bromide) or by the use of labelled nucleic acids, such as polypeptides labelled with fluorophores. Other detection techniques that do not require the use of labels include optical techniques such as optoacoustics, reflectometry, ellipsometry and surface plasmon resonance (see WO97/49989).

Thus, the present invention provides a solid substrate having immobilized thereon at least one polynucleotide of the present invention, preferably two or more different polynucleotide sequences of the present invention. In a preferred embodiment the solid substrate further comprises polynucleotide sequences derived from genes other than the PMC virus polynucleotide sequence.

Antisense Nucleic Acids and Ribozymes

The present invention also extends to the preparation of antisense nucleotides and ribozymes that may be used to interfere with the expression of PMC virus amino acid sequences at the translational level. This approach utilises antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule [See: Weintraub, (1990) *Sci. Am.*, 262:40-46; Marcus-Sekura, (1988) *Anal. Biochem.*, 172:289-295]. In the cell, they hybridise to that mRNA, forming a double-stranded molecule. The cell does not translate an mRNA complexed in this double-stranded form. Therefore, antisense nucleic acids interfere with the expression of mRNA into protein. Oligomers of about fifteen nucleotides and molecules that hybridise to the AUG initiation codon will be particularly efficient, since they are easy to synthesize and are likely to pose fewer problems than larger molecules when introducing them into infected cells. Antisense methods have been used to inhibit the expression of many genes in vitro [Hambor et al., (1988) *J. Exp. Med.*, 168:1237-1245].

Ribozymes are RNA molecules possessing the ability to specifically cleave other single-stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognise specific nucleotide sequences in an RNA molecule and cleave it [Cech, (1988) *J. Am. Med. Assoc.*, 260:3030-3034]. Because they are sequence-specific, only mRNAs with particular sequences are inactivated.

Investigators have identified two types of ribozymes, Tetrahymena-type and "hammerhead"-type. Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species and eighteen base recognition sequences are preferable to shorter recognition sequences.

The PMC polynucleotide sequences described herein may thus be used to prepare antisense molecules against, and ribozymes that cleave, mRNAs for PMC virus amino acid sequences, thus inhibiting expression of the PMC virus polynucleotide sequences.

Polypeptide Sequences

Polypeptides

The invention also covers polypeptides encoded by the above RNA and DNA nucleotide sequences and fragments thereof. The invention further provides an isolated PMC virus amino acid sequence as shown in SEQ ID NO: 2 and fragments thereof. More desirably, the PMC virus amino acid sequence is provided in substantially purified form. Further provided are polypeptide fragments having lower molecular weights and having peptide sequences or fragments in common with those shown in SEQ ID NO:2.

The term "isolated" is used to describe a PMC virus amino acid sequence that has been separated from components that accompany it in its natural state. Further, a PMC virus amino acid sequence is "substantially purified" when at least about 60 to 75% of a sample exhibits a single PMC virus amino acid sequence. A substantially purified PMC virus amino acid sequence will typically comprise about 60 to 90% W/W of a PMC virus amino acid sequence sample, more usually about 95%, and preferably will be over about 99% pure. Protein purity or homogeneity may be indicated by a number of means well known in the art, such as polyacrylamide gel electrophoresis of a protein sample, followed by visualizing a single PMC virus amino acid sequence band upon staining the gel. For certain purposes, higher resolution may be provided by using HPLC or other means well known in the art which are utilised for application.

The invention further contemplates fragments of the PMC virus amino acid sequence. A PMC virus amino acid sequence fragment is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

In a highly preferred form of the invention the fragments exhibit ligand-binding, immunological activity and/or other biological activities characteristic of PMC virus amino acid sequences. More preferably, the fragments possess immunological epitopes consistent with those present on native PMC virus amino acid sequences.

As used herein, "epitope" refers to an antigenic determinant of a polypeptide. An epitope could comprise three amino acids in a spatial conformation that is unique to the epitope. Generally, an epitope consists of at least five amino acids, and more usually consists of at least 8-10 amino acids. Methods of determining the spatial conformation of such amino acids are known in the art.

Preferred PMC virus amino acid sequences of the invention will have one or more biological properties (eg in vivo, in vitro or immunological properties) of the native full-length PMC virus amino acid sequence. Alternatively, fragments of the full-length PMC virus amino acid sequence may have one or more biological properties of one or more of the genes which the full length amino acid sequence encodes.

Preferably, the fragments of the full length PMC virus amino acid sequence SEQ ID NO:2 are chosen from the following locations in SEQ ID NO:2: 1-167, 168-267, 268-489, 490-685, 686-1062, 1063-1134, 1135-1602, 1603-2278, 2279-2341, 2342-2688, 2689-3193, 3194-3886. Alternatively, the fragment may be selected from any one of SEQ ID NOs:16-27.

Non-functional PMC virus amino acid sequences are also included within the scope of the invention since they may be useful, for example, as antagonists of PMC virus genes. The biological properties of analogues, fragments, or derivatives relative to wild type may be determined, for example, by means of biological assays.

PMC virus amino acid sequences, including analogues, fragments and derivatives, can be prepared synthetically (e.g., using the well known techniques of solid phase or solution phase peptide synthesis). Preferably, solid phase synthetic techniques are employed. Alternatively, PMC virus amino acid sequences of the invention can be prepared using well known genetic engineering techniques, as described infra. In yet another embodiment, PMC virus amino acid sequences can be purified (e.g., by immunoaffinity purification) from a biological fluid, such as but not limited to whole blood, plasma, faeces, serum, or urine from animals, including pigs, cattle, sheep, chickens, human beings, dogs, horses, and fish.

Variant Polypeptides

PMC virus amino acid sequence analogues preferably include those having an amino acid sequence wherein one or more of the amino acids is substituted with another amino acid, which substitutions do not substantially alter the biological activity of the molecule.

In the context of the invention, an analogous sequence is taken to include a PMC virus amino acid sequence which is at least 60, 70, 80 or 90% homologous, preferably at least 95 or 98% homologous at the amino acid level over at least 20, 50, 100 or 200 amino acids, with the amino acid sequence set out in SEQ ID NO:1. In particular, homology should typically be considered with respect to those regions of the sequence known to be essential for the function of the protein or proteins encoded by the PMC virus RNA, rather than non-essential neighbouring sequences.

Although homology can be considered in terms of similarity (i.e. amino acid residues having similar chemical properties/functions), in the context of the present invention it is preferred to express homology in terms of sequence identity. The terms "substantial homology" or "substantial identity", when referring to PMC virus amino acid sequences, indicate that the PMC virus amino acid sequence in question exhibits at least about 70% identity with an entire naturally-occurring PMC amino acid sequence or portion thereof, usually at least about 80% identity and preferably at least about 90 or 95% identity.

In a highly preferred form of the invention, a PMC virus amino acid sequence analogue will have 80% or greater amino acid sequence identity to the PMC virus amino acid sequence set out in SEQ ID NO:2. Examples of PMC virus amino acid sequence analogues within the scope of the invention include the amino acid sequence of SEQ ID NO:2 wherein: (a) one or more aspartic acid residues is substituted with glutamic acid; (b) one or more isoleucine residues is substituted with leucine; (c) one or more glycine or valine residues is substituted with alanine; (d) one or more arginine residues is substituted with histidine; or (e) one or more tyrosine or phenylalanine residues is substituted with tryptophan.

PMC virus amino acid sequence derivatives are also provided by the invention and include PMC virus amino acid sequences, analogues or fragments thereof which are substantially homologous in primary structure but which include chemical and/or biochemical modifications or unusual amino acids. Such modifications include, for example, acetylation, carboxylation, phosphorylation, glycosylation, ubiquitination, labelling, (e.g., with radionucleotides), and various enzymatic modifications, as will be readily appreciated by those well skilled in the art.

In one form of the invention the chemical moieties suitable for derivatisation are selected from among water soluble polymers. The polymer selected should be water soluble so that the protein to which it is attached does not precipitate in an aqueous environment, such as a physiological environment. Preferably, for therapeutic use of the end-product preparation, the polymer will be pharmaceutically acceptable. One skilled in the art will be able to select the desired polymer based on considerations such as whether the polymer/protein conjugate will be used therapeutically, and if so, the desired dosage, circulation time, resistance to proteolysis and other considerations. For the present proteins and peptides, these may be ascertained using the assays provided herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols and polyvinyl alcohol. Polyethylene glycol propionaldehyde may provide advantages in manufacturing due to its stability in water.

In another form of the invention the amino acid sequences may be modified to produce a longer half life in an animal host, for example, by fusing one or more antibody fragments (such as an Fc fragment) to the amino or carboxyl end of a PMC virus amino acid sequence.

Where the PMC virus amino acid sequence is to be provided in a labelled form, a variety of methods for labelling amino acid sequences are well known in the art and include radioactive isotopes such as $^{32}P$, ligands which bind to labelled antiligands (eg, antibodies), fluorophores, chemiluminescent agents, enzymes and antiligands which can serve as specific binding pair members for a labelled ligand. The choice of label depends on the sensitivity required, stability requirements, and available instrumentation. Methods of labelling amino acid sequences are well known in the art [See, e.g., Sambrook at al., *Molecular Cloning: A Laboratory Manual*, Second Edition, Cold Spring Harbor Laboratory Press, Cold Spring Harbor, N.Y. (1989); and Ausubel, F., Brent, R., Kingston, R. E., Moore, D. D., Seidman, J. G., Smith, J. A., Struhl, K. *Current protocols in molecular biology*. Greene Publishing Associates/Wiley Intersciences, New York (2001)].

The PMC virus amino acid sequences of the invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

The invention also provides for fusion polypeptides, comprising PMC virus amino acid sequences and fragments. Thus PMC virus amino acid sequences may be fusions between two or more PMC virus amino acid sequences or between a PMC virus amino acid sequence and a related protein. Likewise, heterologous fusions may be constructed which would exhibit a combination of properties or activities of the derivative proteins. For example, ligand-binding or other domains may be "swapped" between different fusion polypeptides or fragments. Such homologous or heterologous fusion polypeptides may display, for example, altered strength or specificity of binding. Fusion partners include immunoglobulins, bacterial beta-galactosidase, trpE, protein A, beta-lactamase, alpha amylase, alcohol dehydrogenase and yeast alpha mating factor.

Modified PMC virus amino acid sequences may be synthesised using conventional techniques, or may be encoded by a modified polynucleotide sequence and produced using recombinant nucleic acid methods. The modified polynucleotide sequence may also be prepared by conventional techniques. Fusion proteins will typically be made by either recombinant nucleic acid methods or may be chemically synthesised.

Diagnostics

In accordance with another embodiment the invention provides diagnostic and prognostic methods to detect the presence of PMC virus using PMC virus glycoproteins, proteins and other peptides and polypeptides (whether obtained in a purified state from PMC virus preparations, or by chemical synthesis) and/or antibodies derived there from and/or PMC virus polynucleotide sequences.

Diagnostic and prognostic methods will generally be conducted using a biological sample obtained from an animal, such as a pig. A "sample" refers to a sample of tissue or fluid suspected of containing a PMC polynucleotide or polypeptide from an animal, but not limited to, e.g., whole blood, blood cells, plasma, serum, milk, faecal samples, tissue and samples of in vitro cell culture constituents.

Polypeptide/Antibody-Based Diagnostics

Means are provided for the detection of proteins of PMC virus, particularly for the diagnosis of PMC or for the detection of antibodies against PMC virus or its proteins, particularly in subjects afflicted with PMC or more generally in asymtomatic carriers and in animal derived products such as meat. Such methods are also referred to as immunoassays.

The invention thus provides a method for detecting the presence of a PMC virus amino acid sequence in a sample, comprising the steps of:

a) contacting a sample suspected of containing a PMC virus amino acid sequence with an antibody that specifically binds to the PMC virus amino acid sequence under conditions which allow for the formation of reaction complexes comprising the antibody and the PMC virus amino acid sequence; and
b) detecting the formation of reaction complexes comprising the antibody and PMC virus amino acid sequence in the sample, wherein detection of the formation of reaction complexes indicates the presence of PMC virus amino acid sequence in the sample.

Particularly the invention relates to an in vitro process of diagnosis making use of an amino acid sequence encoding an envelope glycoprotein or of a polypeptide bearing an epitope of a glycoprotein from PMC virus or any other viral protein (structural or non-structural) for the detection of anti-PMC virus antibodies in serum, milk or body fluids. Preferably, the antibody used in the above methods binds to the E0, E1, E2, NS2, NS3, NS4A, NS4B and/or NS5A, NS5B proteins of PMC virus.

The invention also provides a method for detecting the presence of a PMC virus antibody in a sample, comprising the steps of:

a) contacting a sample suspected of containing a PMC virus antibody with an amino acid sequence under conditions which allow for the formation of reaction complexes comprising the PMC virus antibody and the amino acid sequence; and
b) detecting the formation of reaction complexes comprising the antibody and amino acid sequence in the sample, wherein detection of the formation of reaction complexes indicates the presence of PMC virus antibody in the sample.

A method is also provided for the detection of anti-PMC virus antibodies, comprising the steps of:

a) depositing a predetermined amount of one or several PMC virus antigens onto a solid support such as a microplate;
b) introducing increasing dilutions of a biological fluid (e.g., blood serum or plasma, milk, cerebrospinal fluid, lymphatic fluid or other body fluids) onto the antigens and incubating;
c) washing the solid support with an appropriate buffer;
d) adding specific labelled antibodies directed against the antibodies of the subject; and
e) detecting the antigen-antibody-antibody complex formed, which is then indicative of the presence of PMC virus antibodies in the biological fluid.

Preferably, the antibody used in these methods is derived from an affinity-purified polyclonal antibody, and more preferably a mAb. In addition, it is preferable for the antibody molecules used herein be in the form of Fab, Fab', $F(ab')_2$ or F(v) portions or whole antibody molecules.

Particularly preferred methods for detecting PMC virus based on the above methods include enzyme linked immunosorbent assays, radioimmunoassays, immunoradiometric assays and immunoenzymatic assays, including sandwich assays using monoclonal and/or polyclonal antibodies.

Three such procedures that are especially useful utilise either PMC virus amino acid sequences (or fragments thereof) labelled with a detectable label, antibody $Ab_1$ labelled with a detectable label, or antibody $Ab_2$ labelled with a detectable label. The procedures may be summarized by the following equations wherein the asterisk indicates that the particle is labelled and "AA" stands for the PMC virus amino acid sequence:

A. $AA^*+Ab_1=AA^*Ab_1$
B. $AA+Ab^*_1=AA\ Ab_1^*$
C. $AA+Ab_1+Ab_2^*=Ab_1\ AA\ Ab_2^*$

The procedures and their application are all familiar to those skilled in the art and accordingly may be utilised within the scope of the present invention. The "competitive" or "blocking" procedure, Procedure A, is described in U.S. Pat. Nos. 3,654,090 and 3,850,752. Procedure B is representative of well-known competitive assay techniques. Procedure C, the "sandwich" procedure, is described in U.S. Pat. Nos. RE 31,006 and 4,016,043. Still other procedures are known, such as the "double antibody" or "DASP" procedure.

In each instance, the PMC virus amino acid sequences form complexes with one or more antibody(ies) or binding partners and one member of the complex is labelled with a detectable label. The fact that a complex has formed and, if desired, the amount thereof, can be determined by known methods applicable to the detection of labels.

It will be seen from the above that a characteristic property of $Ab_2$ is that it will react with $Ab_1$. This is because $Ab_1$, raised in one mammalian species, has been used in another species as an antigen to raise the antibody, $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary antibody, and $Ab_2$ will be referred to as a secondary or anti-$Ab_1$ antibody.

The labels most commonly employed for these studies are radioactive elements, enzymes, chemicals that fluoresce when exposed to ultraviolet light, and others.

A number of fluorescent materials are known and can be utilised as labels. These include, for example, fluorescein, rhodamine and auramine. A particular detecting material is anti-rabbit antibody prepared in goats and conjugated with fluorescein through an isothiocyanate.

The PMC virus amino acid sequences or their binding partners can also be labelled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes, which can be used in these procedures, are known and can be utilized. The preferred enzymes are peroxidase, β-glucuronidase, β-D-glucosidase, β-D-galactosidase, urease, glucose oxidase plus peroxidase and alkaline phosphatase. U.S. Pat. Nos. 3,654,090, 3,850,752 and 4,016,043 are referred to by way of example for their disclosure of alternate labelling material and methods.

In another embodiment of the invention there are provided in vitro methods for evaluating the level of PMC virus antibodies in a biological sample comprising the steps of:

a) detecting the formation of reaction complexes in a biological sample according to the method noted above; and
b) evaluating the amount of reaction complexes formed, which amount of reaction complexes corresponds to the level of PMC virus antibodies in the biological sample.

Preferably, the antibody used in the above methods binds to the E0, E1, E2, NS2, NS3, NS4A, NS4B and/or NS5A, NS5B proteins of PMC virus.

In another embodiment of the invention there are provided in vitro methods for evaluating the level of PMC virus polypeptides in a biological sample comprising the steps of:

a) detecting the formation of reaction complexes in a biological sample according to the method noted above; and
b) evaluating the amount of reaction complexes formed, which amount of reaction complexes corresponds to the level of PMC virus polypeptide in the biological sample.

Preferably, the polypeptide used in the above methods encodes the E0, E1, E2, NS2, NS3, NS4A, NS4B and/or NS5A, NS5B proteins of PMC virus.

Further there are provided in vitro methods for monitoring therapeutic treatment of a disease associated with PMC virus in an animal host comprising evaluating, as describe above, the levels of PMC virus antibodies in a series of biological samples obtained at different time points from an animal host undergoing such therapeutic treatment.

The methods for detecting polypeptides using antibodies, or immunoassays, according to the present invention may utilize antigens from the different domains of the new and unique polypeptide sequences of the present invention that maintain linear (in case of peptides) and conformational epitopes (in case of polypeptides) recognized by antibodies in the sera from subjects infected with PMC virus.

It is within the scope of the invention to use, for instance, single or specific oligomeric antigens, dimeric antigens, as well as combinations of single or specific oligomeric antigens.

The PMC virus antigens of the present invention may be employed in virtually any assay format that employs a known antigen to detect antibodies. Of course, a format that denatures the PMC virus conformational epitope should be avoided or adapted.

A common feature of all of these detection methods is that the antigen is contacted with the test specimen suspected of containing PMC virus antibodies under conditions that permit the antigen to bind to any such antibody present in the component. Such conditions will typically be physiologic temperature, pH and ionic strength, using an appropriate predetermined quantity of antigen. The incubation of the antigen with the specimen is followed by detection of immune complexes comprised of the antigen and antibodies derived from the specimen typically by using a labelled second antibody that is directed against the immunoglobulins of the test animal species.

Design of the immunoassays is subject to a great deal of variation, and many formats are known in the art. Protocols may, for example, use solid supports, or immunoprecipitation. Assays which amplify the signals from the immune complex are also known; examples of which are assays which utilize biotin and avidin or streptavidin, and enzyme-labelled and mediated immunoassays, such as ELISA assays. Furthermore, the immunoassay may be, without limitation, in a heterogeneous or in a homogeneous format, and of a standard or competitive type.

In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon™), diazotized paper, nylon membranes, activated beads, and Protein A beads. For example, Dynatech Immunolon™ 1 or Immunlon™ 2 microtiter plates or 0.25 inch polystyrene beads (Precision Plastic Ball) can be used in the heterogeneous format. The solid support containing the antigenic polypeptides is typically washed after separating it from the test sample, and prior to detection of bound antibodies. Both standard and competitive formats are know in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of PMC virus antibodies in the antibody-antigen complexes is directly monitored. This may be accomplished by determining whether labelled anti-xenogeneic (e.g. anti-swine) antibodies which recognize an epitope on anti-PMC virus antibodies will bind due to complex formation. In a competitive format, the amount of PMC virus antibodies in the sample is deduced by monitoring the competitive effect on the binding of a known amount of labelled antibody (or other competing ligand) in the complex.

Complexes formed comprising anti-PMC virus antibody (or in the case of competitive assays, the amount of competing antibody) are detected by any of a number of known techniques, depending on the format. For example, unlabelled PMC virus antibodies in the complex may be detected using a conjugate of anti-xenogeneic Ig complexed with a label (e.g. an enzyme label).

In an immunoprecipitation or agglutination assay format, the reaction between the PMC virus antigens and the antibody forms a network that precipitates from the solution or suspension and forms a visible layer or film of precipitate. If no anti-PMC antibody is present in the test specimen, no visible precipitate is formed.

There currently exist three specific types of particle agglutination (PA) assays. These assays are used for the detection of antibodies to various antigens when coated to a support. One type of this assay is the haemagglutination assay using red blood cells (RBCs) that are sensitized by passively adsorbing antigen (or antibody) to the RBC. The addition of specific antigen antibodies present in the body component, if any, causes the RBCs coated with the purified antigen to agglutinate.

To eliminate potential non-specific reactions in the haemagglutination assay, two artificial carriers may be used instead of RBC in the PA. The most common of these are latex particles. However, gelatin particles may also be used. The assays utilizing either of these carriers are based on passive agglutination of the particles coated with purified antigens.

Nucleic Acid-Based Diagnostics

The present invention further provides methods for detecting the presence or absence of PMC virus in a biological sample, which comprise the steps of:

c) bringing the biological sample into contact with a polynucleotide probe or primer comprising a PMC virus polynucleotide of the invention under suitable hybridising conditions; and d) detecting any duplex formed between the probe or primer and nucleic acid sequences in the sample.

According to one embodiment of the invention, detection of PMC virus may be accomplished by directly amplifying PMC virus polynucleotide sequences from biological sample, using known techniques and then detecting the presence of PMC virus polynucleotide sequences.

The present invention thus also relates to a method for the detection of PMC virus nucleic acids present in a biological sample, comprising:

c) amplifying the nucleic acid with at least one primer as defined above, d) detecting the amplified nucleic acids.

Preferably, the nucleic acid is extracted and/or purified (eg from a from a tissue sample) prior to amplification.

The present invention also relates to a method for the detection of PMC virus nucleic acids present in a biological sample, comprising:

d) hybridizing the nucleic acids of the biological sample at appropriate conditions with one or more probes as defined above, e) washing under appropriate conditions, and f) detecting the hybrids formed.

Preferably, the hybridizing conditions are denatured conditions.

Preferably, the nucleic acid is extracted and/or purified (eg from a from a tissue sample) prior to hybridisation. More preferably, the nucleic acid sample is amplified with at least one primer as defined above, after extraction or at least prior to hybridisation. Preferably, said probes are attached to a solid substrate or detected in a liquid phase by photometric or fluorogenic detection or by other methods of visualisation such as by agarose gel electrophoresis.

The present invention also relates to a method as defined above, wherein said nucleic acids are labelled during or after amplification.

Suitable assay methods for purposes of the present invention to detect hybrids formed between the oligonucleotide probes and the nucleic acid sequences in a sample may comprise any of the assay formats known in the art, such as the conventional dot-blot format, sandwich hybridization or reverse hybridization. For example, the detection can be accomplished using a dot blot format, the unlabelled amplified sample being bound to a membrane, the membrane being incorporated with at least one labelled probe under suitable hybridization and wash conditions, and the presence of bound probe being monitored.

An alternative and preferred method is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the nucleic acids of the sample and the oligonucleotide probes according to the present invention may be used.

In one form of the invention, the target nucleic acid sequence is amplified by PCR and then detected using any of the specific methods mentioned above. Other useful diagnostic techniques for detecting the presence of PMC virus polynucleotide sequences include, but are not limited to: 1) allele-specific PCR; 2) single stranded conformation analysis; 3) denaturing gradient gel electrophoresis; 4) RNase protection assays; 5) the use of proteins which recognize nucleotide mismatches, such as the *E. coli* mutS protein; 6) allele-specific oligonucleotides; and 7) fluorescent in situ hybridisation.

In addition to the above methods, PMC virus polynucleotide sequences may be detected using conventional probe technology. When probes are used to detect the presence of the PMC virus polynucleotide sequences, the biological sample to be analysed, such as blood or serum, may be treated, if desired, to extract the nucleic acids. The sample polynucleotide sequences may be prepared in various ways to facilitate detection of the target sequence; e.g. denaturation, restriction digestion, electrophoresis or dot blotting. The targeted region of the sample polynucleotide sequence usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Sample polynucleotide sequences and probes are incubated under conditions that promote stable hybrid formation of the target sequence in the probe with the putative PMC virus polynucleotide sequence in the sample. Preferably, high stringency conditions are used in order to prevent false positives.

Detection, if any, of the resulting hybrid is usually accomplished by the use of labelled probes. Alternatively, the probe may be unlabelled, but may be detectable by specific binding with a ligand that is labelled, either directly or indirectly. Suitable labels and methods for labelling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labelled moiety.

It is also contemplated within the scope of this invention that the nucleic acid probe assays of this invention may employ a cocktail of nucleic acid probes and/or primers capable of detecting PMC virus polynucleotide sequences. Thus, in one example to detect the presence of PMC virus polynucleotide sequences in a cell sample, more than one probe complementary to PMC virus polynucleotide sequences is employed and in particular the number of different probes is alternatively 2, 3, or 5 different nucleic acid probe sequences.

Additionally, the present invention provides a method for detecting viral RNA or DNA comprising the steps of:

a) immobilizing PMC virus on a support (e.g., a nitrocellulose filter);
b) disrupting the virion; and
c) hybridizing with a probe.

Preferably, the probe is labelled. More preferably, the probe is radiolabelled or fluorescent- or enzyme-labelled. Such an approach to detection of virus has already been developed for Hepatitis B virus in peripheral blood (Scotto J. et al. Hepatology (1983), 3, 379-384).

The present invention also provides a method for rapid screening of genomic DNA derived from the tissue of subjects with PMC virus related symptoms to detect proviral PMC virus related DNA or RNA present in the tissues. Thus, the present invention also provides a method for screening the tissue of subjects comprising the steps of:

a) extracting DNA from tissue;
b) restriction enzyme cleavage of said DNA;
c) electrophoresis of the fragments; and
d) Southern blotting of genomic DNA from tissues and subsequent hybridization with labelled cloned PMC virus DNA.

Hybridization in situ can also be used.

Antigenic Polypeptide Production

Viral RNA and DNA according to the invention can be used for expressing PMC viral antigens for diagnostic purposes, as well as for the production of a vaccine against PMC virus. The methods which can be used to achieve expression of antigenic polypeptides are multifold:

a) DNA can be transfected into mammalian cells with appropriate selection markers by a variety of techniques, such as calcium phosphate precipitation, polyethylene glycol, protoplast-fusion, etc and the resultant proteins purified.

b) DNA fragments corresponding to genes can be cloned into expression vectors for *E. coli*, yeast or mammalian cells and the resultant proteins purified.

c) The provival RNA or DNA can be "shot-gunned" (fragmented) into prokaryotic expression vectors to generate fusion polypeptides. Recombinants, producing antigenically competent fusion proteins, can be identified by simply screening the recombinants with antibodies against PMC virus antigens.

Particular reference in this respect is made to those portions of the genome of PMC virus which, in the figures, are shown to belong to open reading frames and which encode the products having the polypeptide sequences shown. Preferably, the nucleic acid sequences used in the above methods encode the E0, E1, E2, NS2, NS3, NS4A, NS4B and/or NS5A, NS5B proteins of PMC. Preferably, polypeptides are provided containing sequences in common with polypeptides comprising antigenic determinants included in the proteins encoded and expressed by the PMC virus genome.

Antibodies

Antibodies to PMC Proteins

The different peptides according to this invention can also be used themselves for the production of antibodies, preferably monoclonal antibodies specific for the respective different peptides. Thus, according to the invention, PMC virus amino acid sequences produced recombinantly or by chemical synthesis and fragments or other derivatives or analogues thereof, including fusion proteins, may be used as an immunogen to generate antibodies that recognize the PMC virus amino acid sequence. Such antibodies include but are not limited to polyclonal, monoclonal, chimeric, single chain, Fab fragments and a Fab expression library.

Thus, the present invention provides a method for the generation of antibodies comprising the steps of:

a) providing a PMC virus polypeptide sequence to a subject; and
b) collecting the antibodies generated in the subject against the polypeptide.

Preferably, the polypeptide used to generate the antibody is antigenic. More preferably, the polypeptide is chosen from the list comprising the E0, E1, E2, NS2, NS3, NS4A, NS4B and/or NS5A or NS5B proteins of PMC virus. More preferably, the protein used to generate the antibody is the E0, E2, NS2 and/or NS3 proteins or a fragment or derivative thereof. For example, in a highly preferred embodiment, a composition of the invention comprises both a PMC virus E0/E2 complex and an PMC virus NS2/NS3 complex.

A molecule is "antigenic" when it is capable of specifically interacting with an antigen recognition molecule of the immune system, such as an immunoglobulin (antibody) or T cell antigen receptor. An antigenic amino acid sequence contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, $F(ab')_2$ and F(v) (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds antigen.

Exemplary antibody molecules are intact immunoglobulin molecules, substantially intact immunoglobulin molecules and those portions of an immunoglobulin molecule that contain the paratope, including those portions known in the art as Fab, Fab', $F(ab')_2$ and F(v), which portions are preferred for use in the therapeutic methods described herein.

Fab and $F(ab')_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from $F(ab')_2$ portions followed by reduction with mercaptoethanol of the disulfide bonds linking the two heavy chain portions, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts.

For the production of hybridomas secreting said monoclonal antibodies, conventional production and screening methods can be used. These monoclonal antibodies, which themselves are part of the invention, provide very useful tools for the identification and even determination of relative proportions of the different polypeptides or proteins in biological samples, particularly animals samples containing PMC virus or related viruses.

Adjuvants include, but are not limited to, complete Freund's adjuvant, incomplete Freund's adjuvant, saponin, mineral gels such as aluminium hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (*bacille Calmette-Guerin*) and *Corynebacterium parvum*. Preferably, the adjuvant is pharmaceutically acceptable.

Further examples of adjuvants which may be effective include but are not limited to: N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Additional examples of adjuvants and other agents include aluminium hydroxide, aluminium phosphate, aluminium potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, immuno stimulating complexes (ISCOMs), liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

Typically, adjuvants such as Amphigen (oil-in-water), Alhydrogel (aluminium hydroxide), or a mixture of Amphigen and Alhydrogel are used. Only aluminium hydroxide is approved for human use.

The proportion of immunogenic polypeptide and adjuvant can be varied over a broad range so long as both are present in effective amounts. For example, aluminium hydroxide can be present in an amount of about 0.5% of the vaccine mixture ($Al_2O_3$ basis). Conveniently, the vaccines are formulated to contain a final concentration of immunogen in the range of from 0.2 to 200 μg/ml, preferably 5 to 50 μg/ml, most preferably 15 μg/ml.

After formulation, the vaccine may be incorporated into a sterile container which is then sealed and stored at a low temperature, for example 4° C., or it may be freeze-dried. Lyophilisation permits long-term storage in a stabilised form.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

The PMC virus polypeptides of the invention may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

Compositions of the present invention may further comprise antigenic polypeptides that are not coupled to PMC virus polypeptides and/or biologically active molecules whose primary purpose is not to serve as an antigen but to modulate the immune response in some other aspect. Examples of biologically molecules that modulate the immune system of an animal or human subject include cytokines.

The term "cytokine" refers to any secreted polypeptide that influences the function of other cells mediating an immune response. Some examples of cytokines include, but are not limited to, interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (1-9), interleukin-10 (IL-10), interleukin-11 (IL-11), interleukin-12 (IL-12), interferon-α (IFN-α), interferon-β (IFN-β), interferon-γ (IFN-γ), tumour necrosis factor-α (TNF-α), tumour necrosis factor-β (TNF-β), granulocyte colony stimulating factor (G-CSF), granulocyte/macrophage colony stimulating factor (GM-CSF), and transforming growth factor-β(TGF-β).

Various procedures known in the art may be used for the production of polyclonal antibodies to PMC virus amino acid sequences, or fragment, derivative or analogues thereof.

For the production of antibody, various host animals can be immunised by injection with the PMC virus amino acid sequence, or a derivative (e.g., fragment or fusion protein) thereof, including but not limited to rabbits, mice, rats, sheep, goats, etc.

In one embodiment, the PMC virus amino acid sequences or fragment thereof can be conjugated to an immunogenic carrier, e.g., bovine serum albumin (BSA) or keyhole limpet hemocyanin (KLH).

Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum.*

For preparation of monoclonal antibodies directed toward the PMC virus amino acid sequences, or fragments, analogues, or derivatives thereof, any technique that provides for the production of antibody molecules by continuous cell lines in culture may be used. These include but are not limited to the hybridoma technique originally developed by Kohler at al., (1975) *Nature,* 256:495-497, the trioma technique, the human B-cell hybridoma technique [Kozbor et al., (1983) *Immunology Today,* 4:72], and the EBV-hybridoma technique to produce human monoclonal antibodies [Cole et al., (1985) in *Monoclonal Antibodies and Cancer Therapy, pp.* 77-96, Alan R. Liss, Inc.]. Immortal, antibody-producing cell lines can be created by techniques other than fusion, such as direct transformation of B lymphocytes with oncogenic DNA, or transfection with Epstein-Barr virus. See, e.g., U.S. Pat. Nos. 4,341,761; 4,399,121; 4,427,783; 4,444,887; 4,451,570; 4,466,917; 4,472,500; 4,491,632; and 4,493,890.

In an additional embodiment of the invention, monoclonal antibodies can be produced in germ-free animals. According to the invention, swine antibodies may be used and can be obtained by using swine hybridomas or by transforming B cells with PMC virus in vitro. In fact, according to the invention, techniques developed for the production of "chimeric antibodies" [Morrison et al., (1984) *J. Bacteriol.,* 159-870; Neuberger et al., (1984) *Nature,* 312:604-608; Takeda at al., (1985) *Nature,* 314:452-454] by splicing the genes from a mouse antibody molecule specific for a PMC amino acid sequence together with genes from an antibody molecule of appropriate biological activity can be used; such antibodies are within the scope of this invention. Such chimeric antibodies are preferred for use in therapy of intestinal diseases or disorders, since the antibodies are much less likely than xenogenic antibodies to induce an immune response, in particular an allergic response, themselves.

According to the invention, techniques described for the production of single chain antibodies (U.S. Pat. No. 4,946, 778) can be adapted to produce PMC virus amino acid sequence-specific single chain antibodies. An additional embodiment of the invention utilises the techniques described for the construction of Fab expression libraries [Huse et al., (1989) *Science,* 246:1275-1281] to allow rapid and easy identification of monoclonal Fab fragments with the desired specificity for a PMC virus amino acid sequence, or its derivatives, or analogues.

Antibody fragments, which contain the idiotype of the antibody molecule, can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

Screening for Antibodies

In the production of antibodies, screening for the desired antibody can be accomplished by techniques known in the art, e.g., radioimmunoassay, ELISA, "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention. For example, to select antibodies that recognise a specific epitope of a PMC virus amino acid sequence, one may assay generated hybridomas for a product that binds to a PMC virus amino acid sequence fragment containing such epitope. For selection of an antibody specific to a PMC virus amino acid sequence from a particular species of animal, one can select on the basis of positive binding with PMC virus amino acid sequence expressed by or isolated from cells of that species of animal.

Labelling Antibodies

Advantageously, the labelling of the anti-immunoglobulin antibodies is achieved by an enzyme selected from among those which are capable of hydrolysing a substrate, which substrate undergoes a modification of its radiation-absorption, at least within a predetermined band of wavelengths. The detection of the substrate, preferably comparatively with respect to a control, then provides a measurement of the likelihood of exposure of an animal to the virus, or of the effective presence, of the disease.

Thus, preferred methods of immunoenzymatic and also immunofluorescent detections, in particular according to the ELISA technique, are provided. Titrations may be determinations by immunofluorescence or direct or indirect immunoenzymatic determinations. Quantitative titrations of antibodies on the serums studied can be made.

Epitope Bearing Fragments

Antibodies according to the present invention may be generated using polypeptide fragments (or molecules, particularly glycoproteins having the same polypeptidic backbone as the polypeptides mentioned hereinabove) bearing an epitope characteristic of a protein or glycoprotein of PMC virus. The polypeptide or molecule may further have N-terminal and C-terminal extremities respectively either free or, independently from each other, covalently bonded to amino acids other than those which are normally associated with them in the larger polypeptides or glycoproteins of the PMC virus, which last mentioned amino acids are then free or belong to another polypeptidic sequence.

Conjugation to Increase Immunogenicity

Peptide sequences of small size bearing an epitope or immunogenic determinant, (eg those which are readily generated by chemical synthesis), may require coupling or covalent conjugation to a physiologically acceptable and non-toxic carrier molecule in order to increase their in vivo immunogenic character and thus enhance the production of antibodies.

Particularly, the invention relates to antibodies generated using hybrid polypeptides containing any of the epitope bearing-polypeptides which have been defined more specifically hereinabove, recombined with other polypeptides fragments normally foreign to the PMC virus proteins, having sizes sufficient to provide increased immunogenicity to the epitope-bearing-polypeptide. The foreign polypeptide fragments are preferably immunogenically inert and/or do not interfere with the immunogenic properties of the epitope-bearing-polypeptide.

Such hybrid polypeptides, which may contain from 5 up to 150, even 250 amino acids, usually consist of the expression products of a vector which contains a nucleic acid sequence encoding said epitope-bearing-polypeptide expressible under the control of a suitable promoter or replicon in a suitable host.

Said epitope-bearing-polypeptides, particularly those whose N-terminal and C-terminal amino acids are free, may also be generated by chemical synthesis according to techniques well known in the chemistry of proteins.

Examples of carrier molecules or macromolecular supports which can be used for making the conjugates according to the invention are natural proteins, such as tetanic toxoid, ovalbumin, serum-albumins, hemocyanins, etc. Synthetic macromolecular carriers, for example polysines or poly(D-L-alanine)-poly(L-lysine), can also be used. Other types of macromolecular carriers that can be used, which generally have molecular weights higher than 20,000, are known from the literature.

The conjugates can be synthesized by known processes such as are described by Frantz and Robertson [Infection & Immunity, 33, 193-198 (1981)] and by P. E. Kauffman [pplied and Environmental Microbiology", October 1981 Vol. 42, No. 4, pp. 611-614]. For instance, the following coupling agents can be used: glutaric aldehyde, ethyl chloroformate, water-soluble carbodiimides such as(N-ethyl-N'(3-dimethylamino-propyl) carbodiimide, HCl), diisocyanates, bis-diazobenzidine, di- and trichloro-s-triazines, cyanogen bromides and benzaquinone, as well as the coupling agents mentioned in Scand. J. Immunol., 1978, vol. 8, pp. 7-23 (Avrameas, Ternynck, Guesdon).

Any coupling process can be used for bonding one or several reactive groups of the peptide, on the one hand, and one or several reactive groups of the carrier, on the other hand. Coupling is advantageously achieved between the carboxyl and amine groups carried by the peptide and the carrier in the presence of a coupling agent of the type used in protein synthesis, e.g., 1-ethyl-3-(3-dimethylaminoproyl)-carbodiimide, N-hydroxybenzotriazole, etc. Coupling between amine groups respectively borne by the peptide and the carrier can also be made with glutaraldehyde, for instance, according to the method described by Boquet et al. (1982) Molec. Immunol., 19, 1441-1549, when the carrier is haemocyanin.

The immunogenicity of epitope-bearing-peptides can also be increased by oligomerisation thereof, for example in the presence of glutaraldehyde or any other suitable coupling agent. In particular, the invention relates to the water soluble immunogenic oligomers thus obtained, comprising particularly from 2 to 10 monomer units.

Vaccines

The invention also relates to vaccine compositions whose active principle is a polypeptide or fragment thereof of the present invention i.e. the hereinabove disclosed polypeptides of PMC virus, fusion polypeptides or oligopeptides, in association with a suitable pharmaceutically or physiologically acceptable carrier. The present invention further provides immunogenic polypeptides, and more particularly protective polypeptides, for use in the preparation of vaccine compositions against PMC or related syndromes.

Thus, the present invention provides a vaccine composition comprising a PMC virus polypeptide or fragment thereof.

Preferably, the polypeptide is an antigenic polypeptide. More preferably, the vaccine further comprises a pharmaceutically acceptable carrier or diluent.

The invention also provides a vaccine composition comprising a PMC virus nucleotide or fragment thereof that encodes for a PMC virus polypeptide.

The term "vaccine" as used herein, refers to mean any composition of the invention containing PMC virus peptide or polypeptide or nucleotide sequences coding for PMC virus polypeptides having at least one antigenic determinant which, when administered to a animal, is capable of stimulating an immune response against the antigenic determinant. It will be understood that the term vaccine does not necessarily imply that the composition will provide a complete protective response. Rather a therapeutic effect will be sufficient.

The phrase "immune response" refers to any cellular process that is produced in the animal following stimulation with an antigen and is directed toward the elimination of the antigen from the animal. The immune response typically is mediated by one or more populations of cells characterized as being lymphocytic and/or phagocytic in nature.

A vaccine may generate an immune response that blocks the infectivity, either partially or fully, of an infectious agent. The administration of the vaccine of the present invention may be for either a prophylactic or therapeutic purpose. When provided prophylactically, the vaccine is provided in advance of any exposure to PMC virus or in advance of any symptom of any symptoms due to PMC virus infection. The prophylactic administration of the immunogen serves to prevent or attenuate any subsequent infection by PMC virus in a mammal or reduce the severity of infection and/or symptoms. When provided therapeutically, the vaccine is provided at (or shortly after) the onset of the infection or at the onset of any symptom of infection or disease caused by PMC virus. The therapeutic administration of the vaccine serves to attenuate the infection or disease.

The immune response generated against an introduced PMC virus peptide or polypeptide will be dictated by the amino acid constitution of the antigenic peptide or polypeptide. Such determinants may define either humoral or cell mediated antigenic regions. Without being limited to any particular mode of action, it is contemplated that the immune response generated by the PMC virus peptide or polypeptide will preferably include both humoral and cell mediated immune responses. Where a cell mediated immune response is effected it preferably leads to a T cell cascade, and more specifically by means of a cytotoxic T cell cascade.

The term "cytotoxic T cell", as used herein, refers to any T lymphocyte expressing the cell surface glycoprotein marker CD8+ that is capable of targeting and lysing a target cell which bears a major histocompatibility class I (MHC Class I) complex on its cell surface and is infected with an intracellular pathogen.

Preferably, the vaccine composition is developed to generate antibodies against the E0 and E2 envelope glycoproteins and the NS2 and NS3 non-structural proteins.

The vaccine compositions of the present invention may be used to vaccinate animals and humans against infectious diseases, preferably against PMC. The term "animal" includes: mammals such as farm animals including sheep, goats, pigs, cows, horses, llamas, household pets such as dogs and cats, and primates; birds, such as chickens, geese and ducks; fish; and reptiles such as crocodiles and alligators.

The vaccine composition according to the invention preferably contains a nucleotide sequence as described above, either as such or as a vaccine strain or in a vector or host organism, or a polypeptide as described above, in an amount effective for producing protection against a pestivirus infection. The vaccine can also be a multipurpose vaccine comprising other immunogens or nucleotides encoding these. The vaccines can furthermore contain conventional carriers, adjuvants, solubilizers, emulsifiers, preservatives etc. The vaccines according to the invention can be prepared by conventional methods.

Preferably, the active principle is a peptide containing less than 250 amino acid units, preferably less than 150, particularly from 5 to 150 amino acid residues, as deducible from the complete genome of PMC virus.

The term 'effective amount' refers to an amount of epitope-bearing polypeptide sufficient to induce an immunogenic response in the subject to which it is administered either in a single dose or as part of a series of doses. Preferably, the effective amount is sufficient to effect prophylaxis or treatment, as defined above. The exact amount necessary will vary according to the application. For vaccine applications or for the generation of polyclonal antiserum/antibodies, for example, the effective amount may vary depending on the taxonomic group or species of subject to be treated (e.g. nonhuman primate, primate, etc.), the age and general health and physical condition of the subject, the severity of the condition being treated, the capacity of the subject's immune system to synthesize antibodies, the degree of protection desired, the formulation of the vaccine, the strain of infecting PMC virus, the particular polypeptide selected and its mode of administration, and other relevant factors. It is also believed that effective amounts will be found within a relatively large, non-critical range. An appropriate effective amount can be readily determined using only routine experimentation.

By way of example, suitable dosages of the vaccine compositions are those which are effective to elicit antibodies in vivo, in the host, particularly a porcine host. Suitable doses range from 10 to 500 μg of polypeptide, protein or glycoprotein, for instance 50 to 100 μg. Other preferred ranges of proteins for prophylaxis of PMC are 0.01 to 1000 μg/dose, preferably 0.1 to 100 μg/dose. Several doses may be needed per subject in order to achieve a sufficient immune response and subsequent protection against PMC.

The immunogenic compositions are conventionally administered using standard procedures, for example, intravenously, subcutaneously, intramuscularly, intraorbitally, ophthalmically, intraventricularly, intracranially, intracapsularly, intraspinally, intracisternally, intraperitoneally, buccal, rectally, vaginally, intranasally, orally or by aerosol administration.

Preferably, the immunogenic composition is administered parenterally, typically by injection, for example, subcutaneously or intramuscularly. However, additional formulations suitable for other methods of administration include oral formulations and suppositories or prepared for pulmonary, nasal or other forms of administration. Dosage treatment may be a single dose schedule or a multiple dose schedule.

The mode of administration of the immunogenic vaccine compositions prepared in accordance with the invention will necessarily depend upon such factors as the stability of the immunogenic compositions under physiological conditions, the intensity of the immune response required etc.

The vaccine compositions of the invention may be co-administered with additional immune response enhancers or biological response modifiers including, but not limited to, the cytokines IFN-α, IFN-γ, IL-2, IL-4, IL-6, TNF, or other cytokine-affecting immune cells. In accordance with this aspect of the invention, the PMC virus peptide or polypeptide is administered in combination therapy with a therapeutically active amount of one or more of these cytokines. In addition, conventional antibiotics may be coadministered with the PMC virus peptide or polypeptide. The choice of suitable antibiotics will however be dependent upon the disease in question.

Parenteral Delivery

The compounds provided herein can be administered by any parenteral techniques such as subcutaneous, intravenous and intraperitoneal injections. Typically, such vaccines are prepared either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients and carriers, which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine.

Oral Delivery

Contemplated for use herein are oral solid dosage forms, which are described generally in Martin, Remington's Pharmaceutical Sciences, 18th Ed. (1990 Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatised with various polymers (E.g., U.S. Pat. No. 5,013,556). A description of possible solid dosage forms for the therapeutic is given by Marshall, in Modern Pharmaceutics, Chapter 10, Banker and Rhodes ed., (1979), herein incorporated by reference. In general, the formulation will include a PMC virus polypeptide or polynucleotide, and inert ingredients which allow for protection against the stomach environment, and release of the biologically active material in the intestine.

Also specifically contemplated are oral dosage forms of PMC virus polypeptides or polynucleotides. In this respect the PMC virus polypeptides or polynucleotides may be chemically modified so that oral delivery is efficacious. Generally, the chemical modification contemplated is the attachment of at least one moiety to the protein (or peptide) molecule itself, where said moiety permits (a) inhibition of proteolysis; and (b) uptake into the blood stream from the stomach or intestine. Also desired is the increase in overall stability of the protein and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski et al., 1981, supra; Newmark et al., J. Appl. Biochem., 4:185-189 (1982). Other polymers that could be used are poly-1,3-dioxolane and poly-1,3,6-tioxocane. Preferred for pharmaceutical usage, as indicated above, are polyethylene glycol moieties.

For PMC virus polypeptides or polynucleotides the location of release may be the stomach, the small intestine (the duodenum, the jejunem, or the ileum), or the large intestine. One skilled in the art has available formulations that will not dissolve in the stomach, yet will release the material in the duodenum or elsewhere in the intestine. Preferably, the release will avoid the deleterious effects of the stomach environment, either by protection of the complex or by release of the biologically active material beyond the stomach environment, such as in the intestine.

To ensure full gastric resistance, a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, PMC virus polypeptides or polynucleotides may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, alpha-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall and these can include but are not limited to: stearic acid including its magnesium and calcium salts, polytetrafluoroethylene (PTFE), liquid paraffin, vegetable oils and waxes. Soluble lubricants may also be used such as sodium lauryl sulphate, magnesium lauryl sulphate, polyethylene glycol of various molecular weights, and Carbowax 4000 and 6000.

Glidants that might improve the flow properties of the complex during formulation and to aid rearrangement during compression might be added. The glidants may include starch, talc, pyrogenic silica and hydrated silicoaluminate.

To aid dissolution of the therapeutic into the aqueous environment, a surfactant might be added as a wetting agent. Surfactants may include anionic detergents such as sodium lauryl sulphate, dioctyl sodium sulphosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the complex either alone or as a mixture in different ratios.

Additives which potentially enhance uptake of the complex are for instance the fatty acids oleic acid, linoleic acid and linolenic acid.

Controlled release formulation may be desirable. The complex could be incorporated into an inert matrix which permits release by either diffusion or leaching mechanisms i.e., gums. Slowly degenerating matrices may also be incorporated into the formulation. Another form of a controlled release of this therapeutic is by a method based on the Oros therapeutic system (Alza Corp.), i.e. the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film-coated tablet; the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Pulmonary Delivery

Also contemplated herein is pulmonary delivery of vaccine composition. The PMC virus polypeptides or polynucleotides may be delivered to the lungs of an animal while inhaling and traverses across the lung epithelial lining to the blood-stream.

Contemplated for use in the practice of this invention are a wide range of mechanical devices designed for pulmonary delivery of therapeutic products, including but not limited to nebulizers, metered-dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of the complex. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified proteins may also be prepared in different formulations depending on the type of chemical modification or the type of device employed.

Formulations suitable for use with a nebulizer, either jet or ultrasonic, will typically comprise the complex suspended in water at a concentration of about 0.1 to 25 mg of biologically active protein per ml of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the complex suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the complex and may also include a bulking agent, such as lactose, sorbitol, sucrose, or mannitol in amounts which facilitate dispersal of the powder from the device, e.g., 50 to 90% by weight of the formulation. The protein (or derivative) should most advantageously be prepared in particulate form with an average particle size of less than 10 microns, most preferably 0.5 to 5 microns, for most effective delivery to the distal lung.

Nasal Delivery

Nasal delivery of the vaccine comprising PMC virus polypeptides or polynucleotides is also contemplated. Nasal delivery allows the passage of the protein to the blood stream directly after administering the therapeutic product to the nose, without the necessity for deposition of the product in the lung. Formulations for nasal delivery include those with dextran or cyclodextran.

Therapeutic Compositions

Polypeptide Based Therapies

The PMC virus polypeptides according to present invention also can be used as a prophylactic or therapeutic, which may be utilised for the purpose of stimulating humoral and cell mediated responses in animals, such as swine, thereby providing protection against infection with PMC virus. Natural infection with PMC virus induces circulating antibody titres against PMC virus. Therefore, PMC virus amino acid sequence or parts thereof, have the potential to form the basis of a systemically or orally administered prophylactic or therapeutic to provide protection against PMC.

Thus, the invention provides pharmaceutical compositions comprising a PMC virus polypeptide that enhances the immunocompetence of the host individual and elicits specific immunity against pathogens, preferably PMC virus.

The therapeutic regimens and pharmaceutical compositions of the invention are described elsewhere in the specification. These compositions are believed to have the capacity to prevent the onset and progression of infectious disease such as PMC.

Preferably the compositions are combined with a pharmaceutically acceptable carrier or diluent to produce a pharmaceutical composition (which may be for human or animal use). Compositions of the invention comprising PMC virus polypeptides may also be combined with suitable components to obtain vaccine compositions. Accordingly, in one embodiment the present invention provides a PMC virus amino acid sequence or fragments thereof described herein in a therapeutically effective amount admixed with a pharmaceutically acceptable carrier, diluent, or excipient.

The phrase "therapeutically effective amount" is used herein to mean an amount sufficient to reduce by at least about 15%, preferably by at least 50%, more preferably by at least 90%, and most preferably prevent, a clinically significant deficit in the activity, function and response of the animal host. Alternatively, a therapeutically effective amount is sufficient to cause an improvement in a clinically significant condition in the animal host or to stimulate by at least about 15%, preferably by at least 50%, more preferably by at least 90%, and most preferably completely, a animal's immune system, causing it to generate an immunological memory against the antigenic determinant.

The phrase "pharmaceutically acceptable" refers to molecular entities and compositions that are physiologically tolerable and do not typically produce an allergic or similarly untoward reaction, such as gastric upset and the like, when administered to an animal. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, *Remington's Pharmaceutical Sciences*, 18th Ed., Mack Publishing Co., Easton, Pa., (1990).

In a more specific form of the invention there are provided pharmaceutical compositions comprising therapeutically effective amounts of PMC virus amino acid sequence or an analogue, fragment or derivative product thereof together with pharmaceutically acceptable diluents, preservatives, solubilizes, emulsifiers, adjuvants and/or carriers. Such compositions include diluents of various buffer content (e.g., Tris-HCl, acetate, phosphate), pH and ionic strength and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Martin, Remington's Pharmaceutical Sciences, 18th Ed. 1990, Mack Publishing Co., Easton, Pa., pp 1435-1712 that are herein incorporated by reference. The compositions may be prepared in liquid form, or may be in dried powder, such as lyophilised form.

The present invention also provides for the use of PMC virus amino acid sequences according to the invention, for manufacture of a medicament for modulation of a disease associated with PMC virus.

Antibody Based Therapeutics

The present invention also provides therapeutic compositions comprising antibodies prepared against the polypeptides of the invention.

The antibodies can be used directly as antiviral agents. To prepare antibodies, a host animal is immunized using one or more PMC virus proteins bound to a carrier as described above for vaccines. The host serum or plasma is collected following an appropriate time interval to provide a composition comprising antibodies reactive with the protein(s) of the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

Such therapeutic antibody compositions may additionally contain one or more of the additional agents described above in relation to polypeptide therapeutics.

The present invention provides for the use of antibodies against the PMC virus according to the invention, for manufacture of a medicament for modulation of a disease associated with PMC virus.

Polynucleotide Based Therapy

The present invention further provides therapeutic compositions comprising PMC virus nucleic acid sequences as well as antisense and ribozyme polynucleotide sequences hybridisable to a polynucleotide sequence encoding a PMC virus amino acid sequence according to the invention.

Polynucleotide sequences encoding antisense constructs or ribozymes for use in therapeutic methods are desirably administered directly as a naked nucleic acid construct. Uptake of naked nucleic acid constructs is enhanced by several known transfection techniques, for example those including the use of transfection agents. Example of these agents include cationic agents (for example calcium phosphate and DEAE-dextran) and lipofectants (for example Iipofectam™ and Transfectam™). Typically, nucleic acid constructs are mixed with the transfection agent to produce a composition.

Alternatively the antisense construct or ribozymes may be combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular, oral or transdermal administration.

Also addressed by the present invention is the use of polynucleotide sequences of the invention, as well as antisense and ribozyme polynucleotide sequences hybridisable to a polynucleotide sequence encoding a PMC virus amino acid sequence according to the invention, for manufacture of a medicament for modulation of a disease associated with PMC virus.

Administration of Therapeutic Compositions

It will be appreciated that therapeutic compositions provided accordingly to the invention may be administered by any means known in the art. Therapeutic compositions may be for administration by injection, or prepared for oral, pulmonary, nasal or other forms of administration. The mode of administration of the therapeutic compositions prepared in accordance with the invention will necessarily depend upon such factors as the stability of the complex under physiological conditions, the intensity of the immune response required etc.

Preferably, the pharmaceutical compositions for administration are administered by injection, orally, or by the pulmonary, or nasal route.

Preferably, the therapeutic compositions are administered using standard procedures, for example, intravenously, subcutaneously, intramuscularly, intraorbitally, ophthalmically, intraventricularly, intracranially, intracapsularly, intraspinally, intracisternally, intraperitoneally, buccal, rectally, vaginally, intranasally, orally or by aerosol administration.

The PMC virus amino acid sequence or antibodies derived there from, or polynucleotide sequences are more preferably delivered by intravenous, intra-arterial, intraperitoneal, intramuscular, or subcutaneous routes of administration. Alternatively, the PMC virus amino acid sequence or antibodies derived there from, properly formulated, can be administered by nasal or oral administration. The routes of administration described are intended only as a guide since a skilled practitioner will be able to determine readily the optimum route of administration and any dosage for any particular animal and condition.

The present invention further provides a method of inducing a protective immune response in an animal or human against a PMC virus comprising the steps of:

a) administering to said animal or human an effective amount of a composition of the invention.

The present invention also provides methods for enhancing an animal's immunocompetence and the activity of its immune effector cells against a PMC virus comprising the step of:

a) administering a composition comprising a therapeutically effective amount of a PMC virus peptide or polypeptide.

Live Vector Delivery Agent

In another aspect of the invention, the PMC virus may be used as a live vector for delivery of recombinant antigens.

Thus, the present invention provides a live vector comprising the PMC virus and a heterologous polynucleotide.

Preferably, the heterlolgous polynucleotide is operably linked to the polyneucletide sequence of the PMC virus, such that expression of the polynucleotide sequence of the PMC virus also leads to expression of the heterologous polynucleotide sequence.

Furthermore, the PMC virus may have one or more sections of autologous polynucleotide sequence removed. Removal of such sequence may preferably render the live virus attenuated in pathogenicity in a host subject.

For example, the PMC virus may be used as a delivery vector to deliver gene sequences that encode a protein from a second infective agent into a subject to be vaccinated against the second infective agent. The second infective agent may be a virus (such as classical swine fever virus), a bacteria, a parasite etc.

Alternatively, the PMC virus may be used as a delivery vector to deliver antigens from some other source. For example, a PMC virus vector may be used to deliver antigenic proteins to a subject to stimulate the subject to make antibodies against the antigenic proteins that may be collected for purposes such as use in diagnostic kits etc.

Drug Screening Assays

The present invention also provides assays that are suitable for identifying substances such as drugs, agents or ligands that bind to PMC virus amino acid sequences. In addition, assays are provided that are suitable for identifying substances that interfere with PMC virus amino acid sequences. Assays are also provided that test the effects of candidate substances identified in preliminary in vitro assays on intact cells in whole cell assays.

Thus, the present invention provides a method of screening for drugs comprising the steps of:

a) contacting an agent with a PMC virus amino acid sequence or fragment thereof and b) assaying for the presence of a complex between the agent and the PMC virus amino acid sequence or fragment.

The present invention also provides a method of screening for ligands of the proteins of the PMC virus comprising the steps of:

a) contacting a ligand with a PMC virus amino acid sequence or fragment thereof and b) assaying for the presence of a complex between the PMC virus amino acid sequence or fragment and a ligand.

One type of assay for identifying substances such as drugs, agents or ligands that bind to PMC virus amino acid sequences involves contacting a PMC virus amino acid sequence, which is immobilised on a solid support, with a non-immobilised candidate substance and determining whether and/or to what extent the PMC virus amino acid sequences and candidate substance bind to each other. Alternatively, the candidate substance may be immobilised and the PMC virus amino acid sequence non-immobilised.

In a preferred assay method, the PMC virus amino acid sequence is immobilised on beads such as agarose beads. Typically this is achieved by expressing the component as a GST-fusion protein in bacteria, yeast or higher eukaryotic cell lines and purifying the GST-fusion protein from crude cell extracts using glutathione-agarose beads. The binding of the candidate substance to the immobilised PMC virus amino acid sequence is then determined. This type of assay is known in the art as a GST pulldown assay. Again, the candidate substance may be immobilised and the PMC virus amino acid sequence non-immobilised.

It is also possible to perform this type of assay using different affinity purification systems for immobilising one of the components, for example Ni-NTA agarose and hexahistidine-tagged components.

Binding of the PMC virus amino acid sequence to the candidate substance may be determined by a variety of methods well known in the art. For example, the non-immobilised component may be labelled (with for example, a radioactive label, an epitope tag or an enzyme-antibody conjugate). Alternatively, binding may be determined by immunological detection techniques. For example, the reaction mixture can be Western blotted and the blot probed with an antibody that detects the non-immobilised component. ELISA techniques may also be used.

Candidate substances are typically added to a final concentration of from 1 to 1000 nmol/ml, more preferably from 1 to 100 nmol/ml. In the case of antibodies, the final concentration used is typically from 100 to 500 μg/ml, more preferably from 200 to 300 μg/ml.

In a competitive binding assay the PMC virus amino acid sequence or fragment is typically labelled. Free PMC virus amino acid sequence or fragment is separated from that present in a protein:protein complex, and the amount of free (i.e., uncomplexed) label is a measure of the binding of the agent being tested to the PMC virus amino acid sequence or its interference with PMC virus amino acid sequence: ligand binding, respectively.

Another technique for drug screening provides high throughput screening for compounds having suitable binding affinity to the PMC virus amino acid sequence and is described in detail in PCT Application WO 84/03564, published on Sep. 13, 1984. Briefly stated, large numbers of different small peptide test compounds are synthesised on a solid substrate, such as plastic pins or some other surface. The peptide test compounds are reacted with PMC virus amino acid sequence and washed. Bound PMC virus amino acid sequence is then detected by methods well known in the art.

This invention also contemplates the use of competitive drug screening assays in which antibodies capable of specifically binding the PMC virus amino acid sequence compete with a test compound for binding to the PMC virus amino acid sequence or fragments thereof. In this manner, the antibodies can be used to detect the presence of any peptide that shares one or more antigenic determinants of the PMC virus amino acid sequence.

Kits

In a further embodiment of this invention, kits may be prepared to determine the presence or absence of PMC virus in suspected infected animals and/or to quantitatively measure PMC infection. In accordance with the testing techniques discussed above, one class of such kits will contain at least the labelled PMC virus amino acid sequence or its binding partner, for instance an antibody specific thereto, and directions depending upon the method selected, e.g., "competitive," "sandwich," "DASP" and the like. The kits may also contain peripheral reagents such as buffers, stabilizers, etc.

Thus, kits for PMC virus serum immunoassay may be either (a) a sandwich type immunoassay, employing a first anti-PMC virus antibody as capture or detector antibody and a second anti-PMC virus antibody as a detector or capture antibody to complement the first anti-PMC virus antibody, or (b) a competitive type immunoassay, employing a anti-PMC virus antibody with a labelled PMC virus antigen or a PMC virus antigen attached to a solid phase.

Accordingly, a test kit may be prepared for the demonstration of the presence of PMC virus comprising:

(a) a predetermined amount of at least one labelled immunochemically reactive component obtained by the direct or indirect attachment of the present PMC virus amino acid sequence or a specific binding partner thereto, to a detectable label;

(b) other reagents; and (c) directions for use of said kit.

More specifically, the diagnostic test kit may comprise:

(a) a known amount of the PMC virus amino acid sequence as described above (or a binding partner) generally bound to a solid phase to form an immunosorbent, or in the alternative, bound to a suitable tag, or there are a plural of such end products, etc;

(b) if necessary, other reagents; and (c) directions for use of said test kit.

In a further variation, the test kit may be prepared and used for the purposes stated above, which operates according to a predetermined protocol (e.g. "competitive," "sandwich," "double antibody," etc.), and comprises:

(a) a labelled component which has been obtained by coupling the PMC virus amino acid sequence to a detectable label;

(b) one or more additional immunochemical reagents of which at least one reagent is a ligand or an immobilized ligand, which ligand is selected from the group consisting of:

(i) a ligand capable of binding with the labelled component (a);

(ii) a ligand capable of binding with a binding partner of the labelled component (a);

(iii) a ligand capable of binding with at least one of the component(s) to be determined; or (iv) a ligand capable of binding with at least one of the binding partners of at least one of the component(s) to be determined; and (c) directions for the performance of a protocol for the detection and/or determination of one or more components of an immunochemical reaction between the PMC virus amino acid sequence and a specific binding partner thereto.

Kits to Detect Antibodies

The invention also provides diagnostic kits for the in vitro detection of antibodies against the PMC virus, which kits comprise any of the polypeptides identified herein and all the biological and chemical reagents, as well as equipment, necessary for performing diagnostic assays.

Accordingly, the invention provides a kit for demonstrating the presence of PMC virus comprising:

(a) a predetermined amount of at least one labelled antibody to the PMC virus;

(b) other reagents; and (c) directions for use of said kit.

Preferably, the polypeptide used in the kit is an antigenic or epitope bearing polypeptide. Most preferably, the polypeptide is a polypeptide encoding, but not exclusively limited to, the E0, E2, NS2 or NS3 protein.

Preferred kits comprise all reagents required for carrying out ELISA assays. Thus preferred kits will include, in addition to any of said polypeptides, suitable buffers and anti-species immunoglobulins, which anti-species immunoglobulins are labelled either by an immunofluorescent molecule or by an enzyme. In the last instance, preferred kits also comprise a substrate hydrolysable by the enzyme and providing a signal, particularly modified absorption of a radiation, at least in a determined wavelength, which signal is then indicative of the presence of antibody in the biological fluid to be assayed with said kit. Kits may also include labelled monoclonal or polyclonal antibodies that are directed against PMC virus epitopes and these labelled antibodies may be used to block or compete with antibodies from the test specimen. If the activity of the labelled antibody is blocked, no or a reduced reaction will occur and it can be deduced that the test specimen contains antibodies to PMC virus.

The present invention also relates to a diagnostic kit for use in detecting the presence of PMC virus antibodies, said kit comprising at least one peptide as defined above, with said peptide being preferably bound to a solid support.

The peptide, for example, can be attached to a variety of different solid supports to enable the washing away of unreacted reagents during the course of using the kit. These include: microwells, coated test tubes, coated magnetic particles, wands or sticks, and membranes (nitrocellulose and others).

Preferably, the peptides are attached to specific locations on the solid support. More preferably, the solid support is a membrane strip and said peptides are coupled to the membrane in the form of parallel lines. Preferably, the peptide used in the kit is an antigenic or epitope bearing peptide.

The PMC virus antigens of the present invention will typically be packaged in the form of a kit for use in these immunoassays. The kit will normally contain, in separate containers, the PMC virus antigen, control antibody formulations (positive and/or negative), labelled antibody when the assay format requires the same and signal generating reagents (e.g. enzyme substrate) if the label does not generate a signal directly. The PMC virus antigen may be already bound to a solid support or may be provided separately, with reagents for binding it to the solid support. Instructions (e.g. written, tape, CD-ROM, etc.) for carrying out the assay usually will be included in the kit.

Immunoassays that utilize PMC virus antigens are useful in screening samples (such as blood, serum, plasma, milk, body fluids) to detect if the subject from which the tissue was derived has been exposed to or infected with PMC virus.

The solid support used in the kits of the present invention can include polymeric or glass beads, nitrocellulose, microparticles, microwells of a reaction tray, test tubes and magnetic beads.

The signal generating compound can include an enzyme, a luminescent compound, a fluorophore such as fluorescein, a time-resolved fluorescent probe such as a europium chelate, a chromogen, a radioactive element, a chemiluminescent compound such as an acridinium ester or particles such as colloidal gold, plain latex, or dyed latex. Examples of enzymes include alkaline phosphatase, horseradish peroxidase and beta-galactosidase.

Kits to Detect Polypeptides and Antigens

The present invention further provides a diagnostic kit for use in detecting the presence of PMC virus proteins.

Accordingly, the invention provides a kit for demonstrating the presence of PMC virus comprising:

(a) a predetermined amount of at least one labelled polypeptide derived from the PMC virus;

(b) other reagents; and (c) directions for use of said kit.

Preferably, said antibody is bound to a solid support. The antibody can be attached to a variety of different solid supports to enable the washing away of unreacted reagents during the course of using the kit. These include: microwells, coated test tubes, coated magnetic particles, wands or sticks, and membranes (nitrocellulose and others). Preferably, the antibodies are attached to specific locations on a solid substrate.

The anti-PMC virus antibody can be attached to the solid support by a variety of means such as passive adsorption, covalent coupling, or by using a solid phase pre-coated with a secondary binder such as protein A, protein G, a secondary antibody specific for the primary antibody, avidin, or an antibody specific for a particular ligand (i.e.: biotin, dinitrophenol, fluorescein, and others). In the case of avidin or any of the ligand specific antibodies, it is necessary to covalently attach the ligand to the anti-PMC virus antibody.

For example, ELISA kits may be used to detect the presence of antigens to PMC virus in a sample to demonstrate that an animal is suffering from PMC or is, for example, a non-symptomatic carrier of the virus.

Preferably, the protein to be detected using the present kit is an antigen or an epitope bearing region of a PMC virus protein. Most preferably, the antibody binds to the E0, E2, NS2 or NS3 protein of PMC.

Kits to Detect Nucleic Acid Sequences

The invention also provides kits for screening animals suspected of being infected with PMC virus, or to confirm that an animal is infected with PMC virus, by detecting PMC virus nucleic acid sequences.

Accordingly, the invention provides a kit for demonstrating the presence of PMC virus comprising:

(a) a predetermined amount of at least one labelled nucleic acid sequence derived from the PMC virus;

(b) other reagents; and (c) directions for use of said kit.

For example, the polynucleotide sequence may be one or more primers, such as those exemplified above, and the instructions for use may be instructions to perform PCR on RNA or DNA extracted from a tissue sample from a subject.

Vectors, Host Cells Etc

Vectors

The present invention also provides a recombinant expression vector comprising a PMC virus nucleic acid sequence or a part thereof as defined above, operably linked to prokaryotic, eukaryotic or viral transcription and translation control elements.

The invention further relates to the hosts (prokaryotic or eukaryotic cells) which are transformed by the above mentioned vectors and recombinants and which are capable of expressing said RNA and/or DNA fragments.

According to another embodiment the present invention provides methods for preparing a PMC virus amino acid sequence, comprising the steps of:

(a) culturing a host cell containing a vector as described above under conditions that provide for expression of the PMC virus amino acid sequence; and (b) recovering the expressed PMC virus sequence.

This procedure can also be accompanied by the step of:

(c) subjecting the amino acid sequence to protein purification.

The present invention also relates to a method for the production of a recombinant PMC virus polypeptide, comprising the steps of:

a) transforming an appropriate cellular host with a recombinant vector, in which a PMC virus polynucleotide sequence or a part thereof has been inserted under the control of appropriate regulatory elements, b) culturing said transformed cellular host under conditions enabling the expression of said insert, and, c) harvesting said polypeptide.

Vectors provided by the present invention will typically comprise a PMC virus polynucleotide sequence encoding the desired amino acid sequence and preferably transcription and translational regulatory sequences operably linked to the amino acid encoding sequence so as to allow for the expression of the antigenic polypeptide in the cell. Preferably, the vector will include appropriate prokaryotic, eukaryotic or viral promoter sequence followed by the PMC virus nucleotide sequences as defined above. The recombinant vector of the present invention may preferably allow the expression of any one of the PMC virus polypeptides as defined above in a prokaryotic, or eukaryotic host or in living mammals when injected as naked RNA or DNA.

The vector may comprise a plasmid, a cosmid, a phage, or a virus or a transgenic animal. Particularly useful for vaccine development may be BCG or adenoviral vectors, as well as avipox recombinant viruses. Examples of such expression vectors are described in Sambrook et al., (1989) supra or Ausubel et al., (2001) supra. Many useful vectors are known in the art and may be obtained from such vendors as Stratagene, New England Biolabs, Promega Biotech, and others.

It may be desirable to use regulatory control sequences that allow for inducible expression of the antigenic polypeptide, for example in response to the administration of an exogenous molecule. Alternatively, temporal control of expression of the antigenic polypeptide may occur by only introducing the polynucleotide into the cell when it is desired to express the polypeptide.

It may also be convenient to include an N-terminal secretion signal so that the antigenic polypeptide is secreted into the cell medium.

Expression vectors may also include, for example, an origin of replication or autonomously replicating sequence and expression control sequences, a promoter, an enhancer and necessary processing information sites, such as ribosome-binding sites, RNA splice sites, polyadenylation sites, transcriptional terminator sequences, and mRNA stabilising sequences. Secretion signals may also be included where appropriate, from secreted polypeptides of the same or related species, which allow the protein to cross and/or lodge in cell membranes, and thus attain its functional topology, or to be secreted from the cell. Such vectors may be prepared by means of standard recombinant techniques well known in the art and discussed, for example, in Sambrook et al., (1989) or Ausubel et al., (2001).

An appropriate promoter and other necessary vector sequences will be selected so as to be functional in the host, and may include, when appropriate, those naturally associated with outer membrane lipoprotein genes.

Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 or promoters derived from murine Moloney leukaemia virus, avian sarcoma viruses, adenovirus II, bovine papilloma virus or polyoma. In addition, the construct may be joined to an amplifiable gene (e.g., DHFR) so that multiple copies of the gene may be made.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

Vectors containing PMC virus polynucleotide sequences can be transcribed in vitro and the resulting RNA introduced into the host cell by well-known methods, e.g., by injection, or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. The introduction of PMC virus polynucleotide sequences into the host cell may be achieved by any method known in the art, including, inter alia, those described above.

In a preferred embodiment, the PMC virus polynucleotide is part of a viral vector, such as a baculovirus vector, or infectious virus, such as a baculovirus. This provides a convenient system since not only can recombinant viral stocks can be maintained and stored until ready for use. Desirably, the nucleotide sequence encoding the antigenic peptide or polypeptides is inserted into a recombinant baculovirus that has been genetically engineered to produce antigenic peptide or polypeptides, for instance, by following the methods of Smith et al (1983) *Mol Cell Biol* 12: 2156-2165. A number of viral transfer vectors allow more than one polynucleotide sequence encoding a polypeptide to be inserted into the same vector so that they can be co-expressed by the same recombinant virus.

Host Cells

To produce a cell capable of expressing PMC virus amino acid sequences, preferably polynucleotide sequences of the invention are incorporated into a recombinant vector, which is then introduced into a host prokaryotic or eukaryotic cell.

The invention also provides host cells transformed or transfected with a PMC virus polynucleotide sequence. Preferred host cells include yeast, filamentous fungi, plant cells, insect, amphibian, avian species, bacteria, mammalian cells, and human cells in tissue culture. Illustratively, such host cells are selected from the group consisting of *E. coli, Pseudomonas, Bacillus, Streptomyces*, yeast, CHO, R1.1, B-W, L-M, COS1. COS 7, BSC1, BSC40, BMT10, and Sf9 cells.

Large quantities of PMC virus polynucleotide sequence of the invention may be prepared by expressing PMC virus polynucleotide sequences or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or *Pseudomonas* may also be used. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate.

Also provided are mammalian cells containing a PMC virus polynucleotide sequences modified in vitro to permit higher expression of PMC virus amino acid sequence by means of a homologous recombinational event consisting of inserting an expression regulatory sequence in functional proximity to the PMC virus amino acid sequence encoding sequence.

The invention is not limited to the production of one antigenic polypeptide at a time in the host cell. Multiple polynucleotides encoding different antigenic polypeptides of interest may be introduced into the same host cell. The polynucleotides may be part of the same nucleic acid molecule or separate nucleic acid molecules.

General

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

As used herein the term "derived" and "derived from" shall be taken to indicate that a specific integer may be obtained from a particular source albeit not necessarily directly from that source.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

EXAMPLES

The following examples serve to more fully describe the manner of using the above-described invention, as well as to set forth the best modes contemplated for carrying out various aspects of the invention. It is understood that these methods in no way serve to limit the true scope of this invention, but rather are presented for illustrative purposes.

Example 1

Sample Preparation

Tissue samples were extracted and prepared using a method whose main basis was derived from Allander et al (2001) "A virus discovery method incorporating DNase treatment and its application to the identification of two bovine parvovirus species." Proc Natl Acad Sci USA. 98(20): 11609-14, with some modifications to improve the efficiency from Baugh et al (2001) "Quantitative analysis of mRNA amplification by in vitro transcription." Nucleic Acids Res. 29(5): E29. However, the methods were modified to improve efficiency.

1. Preparation of Serum Samples:
a) Obtain at least 240 μL of supernatant from a tissue homogenate or serum and divide into 2×120 ul lots
b) To each 120 ul of sample add 240 ul of PBS or $H_2O$ (or take 50 ul sera+100 ul PBS)
c) Filter diluted sample through two separate 0.2 um filters by centrifuging at 2000×g (wash top of filter and keep at −20° C.)
d) Add 25 ul DNASE I (250 U) to each tube of filtered sample and incubate at 37° C. for 2 hr
e) Add 1 ul of RNase Cocktail (500 U Rnase A, 20000 U Rnase T1) to each tube and incubate at RT for 1 hr.
f) Take 1 tube of treated sample (360 ul) for RNA extraction and one tube for DNA extraction (add 500 ul DNAeasy AL+50 ul proteinase K etc and elute in 50 ul water).
2. RNA Extraction:
   a) Divide sample into 90 ul lots and add 600 ul RLT, ie 4×690 ul
   b) Homogenize by passing through 21G syringe at least 5×
   c) Add 690 ul of 70% ethanol to each tube of sample and mix by pipetting
   d) Apply 700 ul of sample to column at a time and centrifuge for 15 sec at 10,000 rpm. Place flow through waste in a 5 ml container and keep at −80° C.
   e) Add 700 ul of buffer RW1 to the column and centrifuge for 15 sec at 10,000 rpm. Discard flow through material and collection tube.

f) Transfer column to a new tube and add 500 ul of RPE centrifuge for 15 sec at 10,000 rpm, discard flow through material g) Repeat step (f) using same tube but centrifuge for 2 min at 10,000 rpm.

h) Transfer column to a new tube and centrifuge for 1 min at 10,000 rpm.

i) Elute the RNA in 20 ul of RNAse free water, let the water sit on the column for 1 minute before centrifuging. Reuse the eluate and centrifuge for 1 min at 10,000 rpm to collect any left over RNA on column.

j) Store RNA at −80° C. until needed.

3. DNA Extraction:

a) To 360 ul of sample add 36 ul of proteinase K and 360 ul of buffer AL, mix by vortex, incubate at 70° C. for 10 minutes.

b) Add 360 ul of 100% ethanol, mix by vortexing c) Pipette mixture from step (b) into DNAeasy column and centrifuge at 8,000 rpm for 1 minute. Place flow-through into a tube and store at −80° C.

d) Place column in a new tube and add 500 ul of AW1 spin at 8,000 rpm for 1 minute. Discard flow through and tube.

e) Place column in a new tube and add 500 ul of AW2 and spin at 13,000 rpm for 3 minutes. Discard flow through and spin for another 1 minute and discard flow through and tube.

f) Place column in a new tube, add 50 ul of water and let sit for 1 minute. Spin at 8,000 rpm for 1 min and collect eluate. Reapply the 50 ul eluate and spin again.

g) Store DNA at −80° C. until needed.

RNA Sequence-Independent Single Primer Amplification (SISPA) for Double Stranded RNA Viruses The SISPA method employed was developed from that of Baugh et al and Allander et al, to maximise yield and product length while minimising template-independent side reactions. However, the present method is applied to low yield viral RNA, not total mRNA and a melting step has been added.

4. First Strand cDNA Synthesis a) Mix together the following:

1 ul random hexamers (10 pmol)

8 ul-9 ul RNA (in $H_2O$)

b) Mix, heat 90° C. 3 minutes, spin and put on ice c) On ice add:

| | |
|---|---|
| $1^{st}$ strand buffer | 4 ul |
| 0.1M dTT | 2 ul |
| 5 mM dNTP | 2 ul |
| SSIII (400U) | 1 ul |
| T4gene32 | 1 ul |

$1^{St}$ strand buffer: 50 mM Tris-HCl (pH 8.3), 75 mM KCl, 3 mM $MgCl_2$ d) Mix, spin and heat at 50° C. for 30 minutes e) Add another 1 ul of SSIII and leave for another 30 min at 50° C.

f) Heat inactivate at 70° C. for 10 minutes and then place on ice

5. Second Strand cDNA Synthesis a) On Ice Mix:

| | |
|---|---|
| H2O | 87 ul |
| 5X $2^{nd}$ strand buffer | 30 ul |
| 5 mM dNTPs | 6 ul |
| DNA polymerase (40U) | 4 ul |
| *E. coli* DNA ligase (10U) | 1 ul |
| RNase H (2U) | 2 ul |
| $1^{st}$ strand DNA mix (step 1) | 20 ul |

-continued $2^{nd}$ Strand Buffer: 20 mM Tris-HCl (pH 6.9), 4.6 mM $MgCl_2$, 90 mM KCl, 0.15 mM b-$NAD^+$, 10 mM $(NH_4)_2SO_4$ b) Mix, spin and incubate at 16° C. for 2 hrs. *NOTE: can start DNA SISPA whilst this incubation is underway.* c) Add 10 ul (10 U) T4 DNA polymerase (1 u/ul) and incubate at 16° C. for 15 min.

d) Heat $2^{nd}$ strand synthesis at 72° C. 10 minutes, let cool to 37° C.

6. Clean Up DNA a) Spin phase lock at 13,000 rpm for 30 sec at 4° C.

b) Add 150 ul of step 2 reaction c) Add equal volume phenol/chloroform 160 ul d) Shake lightly e) Spin at 13000 rpm 5 minutes, 4° C.

f) Transfer upper phase to new tube ~160 ul g) Precipitate DNA add 100% ethanol 2.5V i.e 375 ul and 1 ul glycogen (20 mg/ml) Leave at −20° C. for 2 hrs or 0/N h) Spin at 13000 rpm 20 minutes, remove S/N off pellet i) Wash pellet 1×70% ethanol 13000 rpm 5 min at 4° C.

j) Take pellet up in 35 ul of water *NOTE: can stop here and freeze at −80° C. until the DNA SISPA sample is also ready.*

DNA SISPA

7. Second DNA Strand Synthesis a) Mix together the following:

| | |
|---|---|
| DNA | 50 ul |
| 10 pmol random hexamers (10 pmol/ul) | 1 ul |
| 5U 3'-5' exo Klenow fragment DNA polymerase | 1 ul |
| Buffer (supplied with Klenow fragment DNA polymerase) | 1 ul |
| 5 mM dNTP | 1 ul |
| T4gene32 | 1 ul |

b) Leave at 37° C. for 1 hr

8. Clean Up DNA a) Spin phase lock at 13,000 rpm for 30 sec at 4° C.

b) Add 60 ul of step 1 reaction c) Add equal volume phenol/chloroform 60 ul d) Shake lightly e) Spin at 13,000 rpm 5 minutes, 4° C.

f) Transfer upper phase to new tube ~60 ul g) Precipitate DNA add 100% ethanol 2.5V i.e 150 ul and 1 ul glycogen (20 mg/ml) Leave at −20° C. for 2 hrs or overnight h) Spin at 13,000 rpm for 20 minutes, remove supernatant off pellet i) Wash pellet 1×70% ethanol 13,000 rpm 5 min at 4° C.

j) Take pellet up in 44 ul of water *NOTE: can stop here and freeze at −80° C. until the RNA SISPA sample is also ready.*

Generation of Recombinant Nucleic Acid Sequences

9. Restriction Digest a) Add 10 U Csp 6.1 (i.e 1 ul of 10 U/ul stock) to 35 ul of sample, add 4 ul of Buffer B and 5 ul of Csp6I b) Incubate at 37° C. for 2 hr c) Inactivate at 65° C. for 20 minutes 10. Dephosphorylate Digested DNA a) To inactivated restriction digest (50 ul) add:

6 ul of 10×CIP dephosphorylation buffer 0.3 ul of CIP 18 U/ul 3.7 ul water

CIP Dephosphorylase buffer 1×: 0.05M Tris-HCl, 0.1 mM EDTA, pH8.5 b) Incubate at 37° C. for 30 minutes c) Add another 0.3 ul of CIP 18 U/ul and incubate at 37° C. for 30 minutes 11. Clean Up DNA a) Spin phase lock at 13,000 rpm for 30 sec at 4° C.

b) Add 60 ul dephosphorylated DNA c) Add equal volume (60 ul) phenol/chloroform d) Shake lightly e) Spin at 13,000 rpm 5 minutes, 4° C.

f) Transfer upper phase to new tube ~50 ul g) Precipitate DNA add 2.5 volumes 100% ethanol (150 ul) and 1 ul glycogen (20 mg/ml) Leave at −20° C. for 2 hrs or overnight h) Spin at 13,000 rpm 20 minutes, remove supernatant off pellet i) Wash pellet 1×70% ethanol, spin 13,000 rpm 5 min at 4° C.

j) Dessicate for 2-3 minutes or air dry for 15 minutes k) Reconstitute in 5.8 ul $H_2O$.

12. Adaptor Ligation a) Mix together:

| | |
|---|---|
| T4 DNA ligase (5U/ul) | 1.2 ul |
| 5X Ligase Buffer | 2 ul |
| 50 pmol adaptor (phosphorylated ends) | 1 ul |
| DNA from Step 3. | 5.8 ul |

Ligase buffer 5×: 330 mM Tris-HCl, 25 mM $MgCl_2$, 25 mM DTT, 5 mM ATP, pH 7.5 b) Incubate 4° C. for 1 hr and 16° C. overnight

13. PCR Reaction (Results FIG. 2)

a) Set up the following mix:

| | |
|---|---|
| Ligated DNA (step 4) | 2 ul |
| 50 pmol NBam24 | 1 ul |
| 5 mM dNTP | 2 ul |
| 2 mM MgCl2 | 2 ul |
| 10X PCR Buffer | 5 ul |
| $H_2O$ | 38 ul |

10× PCR buffer: 100 mM Tris-HCl, 500 mM KCl (pH 8.3)

b) Heat at 72° C. for 3 minutes c) Add 0.5 ul Taq DNA polymerase (5 U/ul)

d) Run cycle:

72° C. for 5 minutes (94° C. for 1 minute, 72° C. for 3 minutes)×40 hold at 4° C.

e) Run 10 ul and 40 ul of product on 1.0% EtBr gel (leave a well between them to make purification easier)

14. Cloning PCR Product a) Cut out sections of smeared region from gel as a lot of the dominant bands can be contaminating sequence from the products used in the methods, rather than the actual sample. Bands can also be hard to see if they are in the smeared regions.

b) Clean up DNA from agarose using the Minielute Gel Extraction Kit (Qiagen)

1. Excise the DNA fragment from the agarose gel with a clean, sharp scalpel.
2. Weigh the gel slice in a colourless tube. Add 3 volumes of Buffer QG to 1 volume of gel (100 mg ~100 µl).
3. Incubate at 50° C. for 10 min (or until the gel slice has completely dissolved). To help dissolve gel, mix by vortexing the tube every 2-3 min during the incubation.
4. After the gel slice has dissolved completely, check that the colour of the mixture is yellow (similar to Buffer QG without dissolved agarose). Note: If the colour of the mixture is orange or violet, add 10 µl of 3 M sodium acetate, pH 5.0, and mix. The colour of the mixture will turn to yellow.
5. Add 1 gel volume of isopropanol to the sample and mix by inverting the tube several times.
6. Place a MinElute column in a provided 2 ml collection tube in a suitable rack.
7. To bind DNA, apply the sample to the MinElute column, and centrifuge for 1 min.
8. Discard the flow-through and place the MinElute column back in the same collection tube.
9. Add 500 µl of Buffer QG to the spin column and centrifuge for 1 min.
10. Discard the flow-through and place the MinElute column back in the same collection tube.
11. To wash, add 750 µl of Buffer PE to the MinElute column and centrifuge for 1 min.
12. Discard the flow-through and centrifuge the MinElute column for an additional 1 min at ≥10,000×g (~13,000 rpm).
13. Place the MinElute column into a clean 1.5 ml microcentrifuge tube.
14. To elute DNA, add 10 µl of Buffer EB (10 mM Tris.Cl, pH 8.5) or $H_2O$ to the centre of the membrane, let the column stand for 1 min, and then centrifuge for 1 min.

c) For ligations and cloning use Invitrogen TA Cloning® Kit Version V 7. Set up the 10 µl ligation reaction as follows:

| | |
|---|---|
| Fresh PCR product | 6 µl |
| 10X Ligation Buffer | 1 µl |
| pCR ® 2.1 vector (25 ng/µl) | 2 µl |
| T4 DNA Ligase (4.0 Weiss units) | 1 µl |

Incubate the ligation reaction at 14° C. overnight, or at −20° C. until you are ready for transformation.

d) Transform One Shot® Competent Cells.

1. Centrifuge vials containing the ligation reactions briefly and place them on ice.
2. Thaw on ice one 50 µl vial of frozen One Shot® Competent Cells (enough for 2 ligations).
3. Pipette 2 µl of each ligation reaction into 25 ul of competent cells and mix by stirring gently with the pipette tip.
4. Incubate the vials on ice for 30 minutes. Store the remaining ligation mixtures at −20° C.
5. Heat shock the cells for 30 seconds at 42° C. without shaking. Immediately transfer the vials to ice.
6. Add 125 µl of room temperature SOC medium to each vial.
7. Shake the vials horizontally at 37° C. for 1 hour at 225 rpm in a shaking incubator.
8. Spread 50 µl to 100 µl from each transformation vial on LB agar plates containing ~80 mg/ml X-Gal and 100 µg/ml ampicillin.
9. Incubate plates overnight at 37° C. Place plates at 4° C. for 2-3 hours to allow for proper colour development.

15. Screening Colonies for Inserts and Sequencing (Results FIG. 3)

a) Use HotStarTaqMaster Mix (50 ul/well of plate):

| 1X | 110X (sufficient for one plate) |
|---|---|
| 25 ul HotStarTaqMaster Mix (vortex) | 2750 ul |
| 12.5 ul M13-20f (50 pmol) | 1375 ul |
| 12.5 ul M13-20f (50 pmol) | 1375 ul |
| add 50ul per well of the plate | |

To make the M13-20f (50 μmol) and M13r (50 μmol) stocks: mix 0.5 ul of 100 uM primer with 12 ul of water i.e 500 ul of 100 uM stock primer+1200 ul water (from HotStarTaq Kit).

b) Place sterile aluminium foil over the plate containing the HotStar TaqMaster Mix. Stab through the foil to make a hole, and then stab a bacterial colony into each well of the plate.

c) Take off aluminium foil and add strip caps to seal plate.

d) Run PCR protocol:

95° C. for 15 min (94° C. for 30 s, 50° C. for 30 s, 72° C. for 1 min) X30

72° C. for 1 min

4° C. hold.

e) Run 5-10 ul of PCR on gel f) Use Qiagen Mini elute to clean up the remaining PCR product to sequence.

Example 2

Enzyme Linked Immunosorbent Assay to Detect Antibodies to PMC Virus

1. Clone and express the PMC virus protein of interest (eg E2, NS3) in baculovirus and purify the expressed protein. This purified protein can be used as an antigen to detect specific antibodies to the PMC virus proteins of interest.

2. Coat 'medium binding' 96 well microplates (50 uL per well) with antigen diluted in carbonate buffer (0.05M Carbonate buffer 1× (pH 9.6): $Na_2CO_3$ (1.59 gm); $NaHCO_3$ (2.93 gm) water to 114 Hold overnight at room temperature (18-25° C.).

3. Dilute samples and controls (Negative, High and Low Positive) 1/100 in sample diluent (phosphate buffered saline (pH 7.3) solution containing 1% skim milk powder and 0.05% Tween 20).

4. Wash plates 5 times with PBS-Tween and tap to dry.

5. Transfer diluted samples and controls to the ELISA plate in duplicate: 50 uL to each well.

6. Incubate at 37° C. for 1 hr in a humidified container.

7. Wash plates 5 times with PBS-Tween, rotate and wash 5 more times, then tap to dry.

8. Dilute conjugate (antiporcine IgG, horseradish peroxidase conjugated) in sample diluent and add 50 uL to each well.

9. Incubate at 37° C. for 1 hr in a humidified container.

10. Wash plates 10 times with PBS-Tween, then 5 times with purified water.

11. Develop by adding 100 uL of TMB substrate to each well. Incubate at 37° C. in the dark for about 10 min until target OD is achieved for controls. A commercially available TMB substrate can be used (eg. Boehringer Mannheim Corp., Pierce Chemical Co., and Kirkegaard & Perry Laboratories).

12. Stop by adding 100 uL of 1M sulphuric acid.

13. Read OD values at 450 nm.

14. Calculate results.

Example 3

Enzyme Linked Immunosorbent Assay to Detect Antigens of PMC Virus

It should be noted that working solutions of the detector reagent and enzyme conjugate reagents should be made within approximately 1 hour of anticipated use and then stored at 4° C.

Materials

ELISA Wash Buffer—10× concentrate: 1 M Tris; HCl (6.25 Normal) for pH adjustment; 0.01% Thimerosal; and 5% Tween 20.

Detector Reagent—10× concentrate: 25% Ethylene Glycol, 0.01% Thimerosal, approximately 5% biotinylated goat anti-PMC virus antibody, and 0.06% yellow food colouring in PBS (pH 7.4). The working Detector Reagent is prepared by mixing 1 part of the Detector Reagent—10× concentrate, 1 part of NSB Reagent 10× concentrate, and 8 parts of Reagent Diluent Buffer. This working agent should be prepared within approximately 1 hour of anticipated use.

NSB Reagent—10× concentrate: 25% Ethylene Glycol, 0.01% Thimerosal, 0.2% Mouse IgG, 0.06% red food colouring in PBS (pH 7.4).

Reagent Diluent Buffer: 2.5% Bovine Serum Albumin, 0.01% Thimerosal, and 1.0% bovine gamma globulin in PBS (pH 7.4).

Enzyme Conjugate Reagent—10× concentrate: 25% Ethylene Glycol, 0.01% Thimerosal, streptavidin-biotinylated horseradish peroxidase complex (dilution approximately 1 to 700), 0.1% rabbit albumin, and 0.02% rabbit gamma globulin in PBS (pH7.4). Working Enzyme Conjugate Reagent should be prepared by mixing 1 part of Enzyme Conjugate Reagent—10× concentrate, 1 part of NSB Reagent—10× concentrate, and 8 parts of Reagent Diluent buffer. This working reagent should be prepared within approximately 1 hour of anticipated use.

Negative Control: 1% Igepal, and 0.01% Thimerosal in PBS (pH 7.4).

Positive Control: 1% Igepal, 0.01% Thimerosal, 1% Bovine Serum Albumin, PMC virus culture (dilution approximately 1:20) and 50 μM phenyl methyl sulfonyl fluoride in PBS (pH7.4).

Method

1. Prepare specimens by standard methods. For samples containing cells (tissues, white blood cells) homogenise the tissue and add sample lysis buffer (1% NP40). Allow at least 1 hour for antigen extraction and mix continually.

2. Clarify specimens by centrifuging for 15 minutes at approximately 2000 g;

3. Coat 96 well microplates with purified polyclonal antiserum raised against PMC virus antigens (100 uL/well). Alternatively, a mixture of anti-PMC virus monoclonal antibodies may be used. Each 96-well tray is coated overnight at room temperature with 0.1 ml per well of a solution containing purified antibody at 5 μg/ml and bovine serum albumin at 10 μg/ml in carbonate buffer (pH9.6). Following the coating, each tray is washed three times with ELISA wash buffer and allowed to dry overnight at 4° C. A foil pouch is used to encase each tray after drying, and a desiccant is included inside each pouch to remove moisture.

4. Wash ELISA plates 3 times by pipetting 0.2 ml of ELISA Wash Buffer into each well and tap or pipette dry prior to the addition of sample.

5. Block ELISA plates with Blocking solution 1 (200 uL/well) for 30 min at 37° C. in a humidified container.
6. Transfer 100 uL of each specimen (including controls) to the ELISA plate;
7. Incubate plates for 60 min at 37° C. in a humidified container;
8. Wash ELISA plates 5 times with ELISA Wash Solution;
9. Block ELISA plates with Blocking Solution 2 (150 uL) for 30 min at 37° C. in a humidified container; 10 Wash ELISA plates 5 times;
11. Add Detector Reagent containing biotinylated anti-PMC virus monoclonal antibody (100 uL) to all wells;
12 Incubate plates for 60 min at 37° C. in a humidified container;
13 Wash plates 5 times;
14. Add Enzyme Conjugate Reagent containing streptavidin-biotinylated horseradish peroxidase complex and add 100 uL to all wells;
15. Incubate plates for 30 min at 37° C. in a humidified container;
16. Wash plates 10 times;
17. Prepare and add 100 uL of TMB substrate solution to all wells. A commercially available TMB substrate may be used (eg. Boehringer Mannheim Corp, Pierce Chemical Co, and Kirkegaard & Perry Laboratories).
18. Incubate plates for approx 10 min at room temperature in the dark;
19. Stop reaction with 1M sulphuric acid (100 uL per well);
20. Read ODs on ELISA plate reader at 450 nm;
21. Calculate results.

Example 4

Detection of PMC Virus RNA by Reverse Transcriptase (RT) Polymerase Chain Reaction (PCR)

a) Extract RNA from the test specimen as described in Example 1. Include in all steps of the reactions known positive and negative controls and a 'blank'.

b) Reverse transcribe (RT) the RNA as follows:

1. Mix together the following:

| | |
|---|---|
| random hexamers (50 pmol) | 1 ul |
| RNA (in H2O) | 9 ul |

2. Heat at 90° C. for 3 minutes, spin and put on ice
3. On ice add:

| | |
|---|---|
| 1st strand buffer | 4 ul |
| 0.1M dTT | 2 ul |
| 5 mM dNTP | 2 ul |
| SSIII (200U) | 1 ul |

4. Mix, spin heat at 45° C. for 60 minutes.
5. Heat inactivate at 70° C. for 10 minutes
6. Place on ice.

c) Set up 1st round PCR

1. Mix together the following PCR reagents

| | |
|---|---|
| RT | 5 ul |
| Forward primer 4 uM | 1 ul |
| Reverse primer 4 uM | 1 ul |
| Hotstart PCR mix (Qiagen) | 12.5 ul |
| Water | 5.5 ul |

(see Table 3 for 1st reaction PCR primers)

2. Cycle the PCR machine at:

95° C. for 15 minutes
(94° C. for 30 sec, 50° C. for 30 sec, 72° C. for 1 min)×40
72° C. for 1 min
4° C. hold d) Set up Nested PCR 1. Mix together the following PCR reagents:

| | |
|---|---|
| 1st PCR product | 1 ul |
| Forward nested primer 2 0uM | 1 ul |
| Reverse nested primer 2 0uM | 1 ul |
| Hotstart PCR mix (Qiagen) | 12.5 ul |
| Water | 9.5 ul |

(see Table 3 for nested PCR primers. If no nested primer is listed, use 1st PCR primer)

2. Cycle the PCR machine at

95° C. for 15 minutes
(94° C. for 30 sec, 50° C. for 30 sec, 72° C. for 1 min)×25
72° C. for 1 min
4° C. hold e) Run 5 ul of nested PCR product on a 1.5% ethidium bromide gel for 1 hour. Depending on the primers used, the expected size of the product is as listed in Table 1.

TABLE 3

Primers for PCR detection of PMC virus

| Clone | Virus | *Primer name | Primer Sequence (5' to 3') | SEQ ID NO | Nested Product |
|---|---|---|---|---|---|
| CR3 9 | Pestivirus | CR39F (63) | CACATCTAGCAGCAGACTATGA | 28 | 103 bp |
| | | CR39R (190) | GTACCAGTTGCACCACCC | 29 | |
| | | CR39FN (87) | TGAAAAGGATTCACGG | 30 | |
| ER5 10 | Pestivirus | ER510F (7) | AAACCGACGAAGTAGACC | 31 | 114 bp |
| | | ER510R (213) | AGACGAGAACATAGTGGC | 32 | |
| | | ER510FN (68) | GAAACAGTAAAGCCAACG | 33 | |
| | | ER510RN (182) | CTGGTAATCGGAAACATC | 34 | |

TABLE 3-continued

Primers for PCR detection of PMC virus

| Clone | Virus | *Primer name | Primer Sequence (5' to 3') | SEQ ID NO | Nested Product |
|---|---|---|---|---|---|
| ER6 2 | Pestivirus | ER62F (203) | GGGACCGAGGGATACGA | 35 | 98 bp |
| | | ER62FN (373) | AGAGGTAATTGGGTAT | 36 | |
| | | ER62R (637) | CAGCAGGTTGATTTCTTCAT | 37 | |
| | | ER62RN (516) | TTGCCAAGTTTCAC | 38 | |
| ER5 5 | Pestivirus | ER55F (31) | AAACCGCCGAAGTAAACC | 39 | 143 bp |
| | | ER55R (214) | CTGGAGCCCTGGTAATGG | 40 | |
| | | ER55FN (64) | GACGGGAATGGGTTCA | 41 | |
| | | ER55RN (162) | TAGGTGCTTCTTATTGGTAT | 42 | |

*F = forward primer, R = reverse primer, FN = forward nested primer, RN = reverse nested primer

Example 5

Determination of Full Length Viral Sequence

Once the authenticity of the presence of PMC virus sequence has been confirmed in a sample by PCR, the entire viral sequence can be acquired by designing PCR primers to span the gaps between the clones (refer to Table 4). RT-PCR was carried out as either a two step (RT then PCR) or one step RT-PCR reaction.

1. RT Reaction:

a) Mix together the following:

1 ul random hexamers (50 μmol)

4 ul RNA 4 ul Rnase free water b) Heat 70° C. 10 minutes, spin and put on ice c) On ice add 4 ul 1st strand buffer 2 ul 0.1M dTT 2 ul 5 mM dNTP 2 ul SSIII (400 U)

d) Mix, spin heat at 42° C. for 60 minutes.

e) Heat inactivate at 70° C. for 10 minutes f) Place on ice

2. PCR Reaction:

a) Mix together the following PCR reagents

| | |
|---|---|
| RT | 1 ul |
| Forward primer 20 uM | 1 ul |
| Reverse primer 20 uM | 1 ul |
| Hotstart PCR mix (Qiagen) | 12.5 ul |
| Water | 13.5 ul |

(see Table 4 for PCR primers)

b) Cycle the PCR machine at:

95° C. for 15 minutes (94° C. for 30 sec, 47° C. for 30 sec, 72° C. for 2 min)×40

72° C. for 1 min

4° C.—hold

3. One Step RT-PCR Method a) Mix Together the Following Reagents from the SSIII RT-PCR Kit

| | |
|---|---|
| 2x reaction mix | 25 ul |
| Forward primer 30 uM | 1 ul |
| Reverse primer 30 uM | 1 ul |
| SSIII RT/Platinum mix | 2 ul for products 2.5 kb or less |
| | 4 ul for products 2.5 kb or more |
| Water | 15.8 ul for products 2.5 kb or less |
| | 13.8 ul for products 2.5 kb or more |

(see Table 4 for PCR primers)

b) Cycle the PCR machine at:

50° C. for 50 minutes

94° C. for 2 min (94° C. for 15 sec, 50° C. for 30 sec, 68° C. for 1 min/kb)×40

68° C. for 5 min

4° C.—hold

RT-PCR product of interest was PCR spin cleaned and cloned into the Invitrogen TA cloning vector PCR2.1 (see Example 1). Positive clones were then identified and sent for sequencing, as described in Example 1.

The primers used for sequencing were M13r, m13-20, primers in Table 4 and primers designed specifically for sequencing (see Table 5).

Plasmid sequence, PCR primers and poor sequence reads were removed from the sequence before being used in the program Bioedit (Hall, T. A. (1999) BioEdit: a user-friendly biological sequence alignment editor and analysis program for Windows 95/98/NT. Nucl. Acids. Symp. Ser. 41:95-98.). Bioedit allowed the construction of contigs and the production of the full length consensus sequence for the virus.

TABLE 4

Primers designed to PCR the gaps between the SISPA clones sequences

| Region to PCR | *Primer names | Primer Sequence (5' to 3') | SEQ ID NO | Product size |
|---|---|---|---|---|
| 5'UTR-Erns | JFP1F | CATGCCCATAGTAGGAC | 43 | 1338 bp |
| | JFRR3R | ACCAGTTRCACCAMCCAT | 44 | |

TABLE 4-continued

| Primers designed to PCR the gaps between the SISPA clones sequences | | | | |
|---|---|---|---|---|
| Region to PCR | *Primer names | Primer Sequence (5' to 3') | SEQ ID NO | Product size |
| Erns-P7 | CR39-Er55PCRF | AGGGCTCTCACATGGTTGTC | 45 | 1810 bp |
| | ER55-510-512 R | CCATTACCAGGGCTCCAG | 46 | |
| Erns-NS5A | CR39F(63) | CACATCTAGCAGCAGACTATGA | 47 | 2349 bp |
| | ER55RN(162) | TAGGTGCTTCTTATTGGTAT | 48 | |
| P7-NS5A | ER55-510-512 F | CGTTGGCTTTACTGTTTCATTG | 49 | 5560 bp |
| | CR316-CR24R | TCCCCGAAGCTTGGTTTAAT | 50 | |
| NS3-NS5A | NS3F | GTCAGGCCTGCCTATCTTTG | 51 | 4431 bp |
| | CR316-CR24R | TCCCCGAAGCTTGGTTTAAT | 52 | |
| NS5A-NS5B | CR316-CR24F | CGGGACCATTAAACCAAGC | 53 | 2440 bp |
| | ER62-ER63R | CAGGGGGTTCCAAGAATACA | 54 | |

*F = forward primer, R = reverse primer

TABLE 5

| Primers designed for sequencing | | | |
|---|---|---|---|
| Protein location of primer | *Primer names | Primer Sequence (5' to 3') | SEQ ID NO |
| 5 UTR | 5utr(140)R | GGTGTACTCACCGCTTAGCC | 55 |
| NPRO | NPRO(630)RS | TTGCTACAATCGCCCTTCTT | 56 |
| NPRO | NPRO(779)FS | AGGGAGAATGACAGGGTCTG | 57 |
| Capsid | capsid(927)FS | ACAAAGGAGCAAAACCCAAG | 58 |
| ERNS | EO(1365)RS | GTCACGTTGGTGGACCCTAC | 59 |
| E1 | E1(2402)RS | AGCCAGAAATGCCACAGC | 60 |
| E1 | E1(2606)FS | ACCTGTGTGGGTGCTAACAT | 61 |
| E2 | E2(3086)RS | TTACTTTGTCTTCCCGTTGC | 62 |
| NS2 | NS2(4409)FS | CCAAGAAACTTCCCCATACG | 63 |
| NS2 | ns2(4460)RS | TTCCACATCCTCTTTCTTCTTTT | 64 |
| NS3 | NS3(5170)RS | GCTGGCCCTCGAATGATCCA | 65 |
| NS3 | NS3(5468)FS | GTTCCCTGTGTCCTTGCTGA | 66 |
| NS3 | NS3(5670)RS | TGTTTTTGTCTTGGCACTGG | 67 |
| NS3 | NS3(6296)FS | GAGCACAACAGGGCAGAAAT | 68 |
| NS3 | NS3(6479)RS | CCATCTTCCTTGTAGGCACA | 69 |
| NS3 | NS3F(6525)F | GTCAGGCCTGCCTATCTTTG | 70 |
| NS3 | NS3(7153)FS | GGAGAAGTCACTGACGCACA | 71 |
| NS3 | NS3(7241)RS | GCCATTTCAATCCCAGTATG | 72 |
| NS4B | NS4B(7715)FS | GGGGTCCACACAGCATTGTA | 73 |
| NS4B | NS4B(7893)RS | CCCTTGATACTCACGCCTGT | 74 |
| NS4B | NS4B(8532)FS | GCCGACTCAAAATGGAGAAA | 75 |
| NS5A | NS5A(8810)RS | GCCACCCTATTCTTGGATCTC | 76 |
| NS5B | NS5B(10889)FS | AAATGAGAAGAGGGCAGTGG | 77 |

TABLE 5-continued

| Primers designed for sequencing | | | |
|---|---|---|---|
| Protein location of primer | *Primer names | Primer Sequence (5' to 3') | SEQ ID NO |
| NS5B | NS5BF-10936 | AAGGCCACCACTCAAATCAC | 78 |
| NS5B | NS5BR-12039 | AGGCTTCTGCTTGACCCAGT | 79 |

*FS = forward primer, RS = reverse primer

NOTE:

Numbers in brackets are estimated locations on Reference pestivirus strain NADL.

Example 6

UTR Sequences

5'RACE and 3'Race were used to aquire the 5'UTR and 3'UTR sequences.

5' RACE Method

Sequence data from the complete 5' untranslated region (UTR) was generated using rapid amplification of cDNA ends (RACE, BD), as described by BD Biosciences Clonetech with the following modifications. PMC virus-specific primer CR24R (5'TCCCCGAAGCTTGGTTTAAT3', SEQ ID NO: 80) was used to generate the cDNA. Hotstart PCR (Qiagen) was carried out with primers CR39R (Table 3) and BD Universal primer A mix (5' CTAATACGACTCACTATAGGGCAAGCAGTGGTATCAACGCAGAGT3', SEQ ID NO: 81; and 5'CTAATACGACTCACTATAGGGC3', SEQ ID NO: 82) with an annealing temperature of 67° C. and extension time of 2 minutes. The PMC virus specific primer $N^{Pro}$(630)RS (Table 5) and BD nested Universal Primer A (5'AAGCAGTGGTATCAACGCAGAT3', SEQ ID NO: 83) were used for the Hotstart Nested PCR, with an annealing temperature of 55° C. and an extension time 2 minutes. Nested PCR products were cleaned, cloned and sequenced.

2. 3' RACE Method

Sequence data from the complete 3' untranslated region was generated by first adding a poly (A) tail to the viral RNA, using Epicentre's A-Plus Ploy(A) polymerase tailing Kit for 8 minutes. This was followed by rapid amplification of cDNA ends (RACE, BD), as described by BD Biosciences Clonetech with the following modifications. Hotstart PCR (Qiagen) was carried out with primers ER62F (Table 3) and BD Universal primer A mix (5' CTAATACGACTCACTATAGGGCAAGCAGTGGTATCAACGCAGAGT3', SEQ ID NO: 84; and 5'CTAATACGACTCACTATAGGGC3', SEQ ID NO: 85) with an annealing temperature of 65° C. and extension time of 2 minutes. The PMC virus specific primer NS5B (12100)F (Table 5) and BD nested Universal Primer A (5'AAGCAGTGGTATCAACGCAGAT3', SEQ ID NO: 86) were used for the Hotstart Nested PCR, with an annealing temperature of 65° C. and an extension time 2 minutes. Nested PCR products were cleaned, cloned and sequenced.

Example 7

Real Time PCR

The following primers and a matching probe based on Taqman® technology were developed:

```
Forward primer:
                                     (SEQ ID NO: 87)
CAGTTGGTGTGATCCATGATCCT

Reverse primer:
                                     (SEQ ID NO: 88)
GGCCTCACCCTGCAACTTT

Probe:
                                     (SEQ ID NO: 89)
6FAM-AAGTCTTCAGCAGTTAACT-MGBNFQ
```

6FAM=6 carboxyfluorescein; MGBNFQ="minor groove binder non-fluorescence quencher." Similar primer/probe combinations may be developed for other segments of the PMC genome.

A Real Time PCR assay was carried out using the following steps:

a) Extract RNA from the test specimen. Include in all steps of the reactions known positive and negative controls and a 'blank'.

b) Prepare reaction mixture (volumes per sample) as follows:

| | |
|---|---|
| 2x Mastermix (Roche) | 12.5 uL |
| 40x Multiscribe | 0.625 uL |
| Forward primer | 1 uL |
| Reverse Primer | 1 uL |
| Taqman Probe | 1 uL |
| Template (sample) | 2 uL |
| Water | 6.875 uL |

c) Set up cycling conditions for the PCR cycler available (the cycles below are appropriate for a Cepheid Smartcycler)

Cycle the PCR machine at:

Stage 1: Repeat 1×

48° C. for 30 min

95° C. for 10 min

Stage 2: Repeat 45×

95° C. for 15 secs

58° C. for 30 secs each d) Determine results using the Smartcycler software using cycle-threshold (CT) values. A CT value of <35 is considered to be positive. Values between 35-40 are suspicious and values>40 are negative.

Example 8

Production of Recombinant Baculoviruses and Expression of Recombinant PMC Virus Proteins 1. Cloning of PCR Fragments PCR products are purified with PCR SPINCLEAN™ columns (Progen Industries, Limited), according to the manufacturer's instructions. If the PCR reaction produces non-specific bands in addition to the required product, or subcloning from another plasmid was necessary, the DNA can be further purified by elution from a 0.8% agarose gel, using a modification of the method described by Heery (1990).

Purified PCR fragments are digested and ligated into pBlueBacHis A, B or C baculovirus transfer vectors (MaxBac Baculovirus Expression System, Invitrogen Corporation) containing compatible cohesive overhangs, using standard cloning protocols (Sambrook et al., 1989; Current Protocols in Molecular Biology, 1991). A, B or C vectors provide three different reading frames to achieve protein expression in the baculovirus expression system.

2. Transformation of Baculovirus Plasmids with the PCR Fragments

The ligations are transformed into competent *E. coli* strain Top 10 (Invitrogen Corporation), Genotype: FmcrA D(mrr-hsdRMS-mcrBC) f80lacZDM15 DlacX74 deoR recA1 araD139 D(ara-leu)7697 galU galK rpsL endA1nupG, and/or Sure® *E. coli* (Stratagene), Genotype: e14$^-$(McrA$^-$)D (mcrCB-hsdSMR-mrr) 171 endA1supE44 thi-1 gyrA96 rel A1 lac recB recJ sbcc umuc::Tn5 (kan$^r$) uurC[F' proAB lacI$^a$Z D m15 Tn10(Tet$^r$)]°. Protocols for the preparation of competent cells and transformation of the bacteria are taken from the Invitrogen MaxBac Baculovirus Expression System Manual Version 1.8.

Screening bacterial clones for plasmid containing PCR fragment and plasmid purification for transfection Bacterial clones containing pBlueBacHis+PCR fragment are identified by growing colonies, extracting the plasmids using the boiling miniprep method described in Sambrook, et al. (1989), and then undertaking restriction digests of the plasmids to verify those containing the correct-sized insert. Recombinant plasmids are purified to a level suitable for transfection reactions using plasmid purification kits (QIAGEN Pty Ltd., tip-20 or tip-100 columns), according to the manufacturer's instructions.

3. Production of Purified Recombinant Baculoviruses by Cationic Liposome Transfection of Sf9 Cells to Produce Recombinant Baculoviruses Recombinant baculoviruses are produced by co-transfecting linearised wild-type *Autographa californica* nuclear polyhedrosis virus (AcMNPV) DNA and baculovirus transfer vector containing PCR fragment into Sf9 cells, by the technique of cationic liposome mediated transfection. This is carried out according to the Invitrogen MaxBac Baculovirus Expression System Manual Version 1.8.

4. Plaque Purifying Recombinant Baculoviruses

Recombinant virus is plaque purified three times before virus master stocks are prepared, ensuring the virus is cloned from a single particle and no wild-type virus is present. Plaque assays are set up according the Invitrogen MaxBac Baculovirus Expression System Manual Version 1.8.

After each round of plaque purification, the recombinant viruses are screened using a modified Pestivirus antigen-capture ELISA (PACE) (Shannon et al., 1991). The modified method involves supernatant+cells (50 μl/well) being added directly to a blocked, washed ELISA plate, and the plate incubated for 1 hr at 37° C. Antibody solution (50 μl/well) is then added. The antibody used is either biotinylated goat anti-pestivirus antiserum or individual anti-PMC virus monoclonal antibodies (mAbs). The plate is incubated overnight at 22° C., then developed as described by Shannon et al. (1991), omitting the incubation with biotinylated anti-mouse IgG for samples that are reacted with the biotinylated goat antiserum.

5. Recombinant Baculovirus Master, Seed and Working Stocks

The master virus stock for each of the recombinant baculoviruses constructed are made according the Invitrogen MaxBac Baculovirus Expression System Manual Version 1.8. The titre of the stock is determined by a plaque assay, as described above, except that the cells are overlaid with 1.5% carboxymethylcellulose (CMC, BDH; 6% CMC in deionised water, diluted 1 in 4 with complete TC100+X-gal [125 μg/ml, Boehringer Mannheim]). After 7 days, the blue plaques are counted to give the virus titre.

The seed and working stock are made from the master and seed stock, respectively using a low MOI of 0.1 to 0.5 pfu/ml. All virus stocks are stored at 4° C. for use in vaccine production. For long term storage of Master, Seed and Working stocks, each recombinant virus is ampouled and frozen at −80° C.

6. Optimisation of Recombinant Protein Production

Sf9 insect-cell suspensions, adapted to Sf-900 II Serum Free Media according to the protocol described by Gibco BRL (1995), are used to optimise recombinant protein expression. Two conical flasks, containing 50 ml cells ($1.5\times10^6$ cells per ml), are infected with recombinant baculovirus at a high and low MOI, between 0.1 and 5.0. A third flask acts as an uninfected control culture. The 3 flasks are incubated with shaking at 28° C., and 5 ml aliquots removed at 24 hr intervals for up to 7 days.

The samples are centrifuged at room temperature (RT) for 10 min at 900×g, and the supernatants carefully removed. The pellets and supernatants are stored at −20° C. until daily sampling is completed. The amount of specific, recombinant pestivirus protein in the samples is then determined using the modified PACE described above. The cell pellets are reconstituted in 200 μl or 250 μl NP-40 (1% [v/v] in PBS), vortexed and centrifuged at RT for 10 min at 900×g. Serial dilutions of the pellet extract (in 1% [v/v] NP40) are assayed. The culture supernatants are assayed undiluted, as well as serially diluted (in 1% [v/v] NP40). If cell viability is reduced at a higher rate of infection, then an MOI or 0.1 to 2 is more appropriate.

Modifications of the above-described modes of carrying out the various embodiments of this invention will be apparent to those skilled in the art based on the above teachings related to the disclosed invention. The above embodiments of the invention are merely exemplary and should not be construed to be in any way limiting.

What is claimed is:

1. An isolated RNA or DNA nucleotide sequence comprising:

a) an RNA or DNA sequence having at least 98% identity with SEQ ID NO: 11, wherein when the isolated RNA or DNA nucleotide sequence is an RNA nucleotide sequence, thymidine (t) nucleotides are substituted with uridine (u) nucleotides;

b) an RNA or DNA sequence having at least 95% sequence identity with SEQ ID NO: 11; or c) an RNA or DNA sequence having at least 90% sequence identity with SEQ ID NO: 11; or d) an RNA or DNA sequence comprising the complement of the nucleotide sequence of (a) or (b) or (c).

2. A method for detecting the presence or absence of porcine myocarditis syndrome (PMC) virus in a biological sample, comprising the steps of:

a) bringing the biological sample into contact with a polynucleotide probe or primer comprising an isolated RNA nucleotide sequence according to claim 1 under suitable hybridizing conditions; and b) detecting any duplex formed between the probe or primer and nucleic acid sequences in the sample.

3. A method for the detection of PMC virus nucleic acids present in a biological sample, comprising:

a) amplifying the RNA or DNA nucleotide sequence of claim 1 with at least one primer, and b) detecting the amplified nucleic acids.

4. A method for the detection of PMC virus nucleic acids present in a biological sample, comprising:

a) hybridizing the nucleic acids of the biological sample at appropriate conditions with one or more probes comprising an isolated RNA or DNA nucleotide sequence according to claim 1, b) washing under appropriate conditions, and c) detecting the hybrids formed.

5. A method for detecting viral RNA or DNA comprising the steps of:

a) immobilizing PMC virus on a support;

b) disrupting the virion; and c) hybridizing the nucleic acids of the virion with a probe comprising an isolated RNA or DNA nucleotide sequence according to claim 1.

6. A method for screening the tissue of subjects for PMC virus comprising the steps of:

a) extracting DNA from tissue;

b) restriction enzyme cleavage of said DNA;

c) electrophoresis of the fragments; and d) Southern blotting of genomic DNA from tissues and subsequent hybridization with a labelled cloned PMC virus DNA sequence according to claim 1.

7. An immunogenic composition comprising an isolated RNA or DNA nucleotide sequence according to claim 1.

8. A vector comprising:

(a) an isolated polynucleotide sequence encoding a PMC virus comprising an isolated RNA or DNA nucleotide sequence according to claim 1; and (b) a heterologous polynucleotide.

9. The vector of claim 8 wherein the heterologous polynucleotide is operably linked to the polynucleotide sequence of the PMC virus, such that expression of the polynucleotide sequence of the PMC virus also leads to expression of the heterologous polynucleotide sequence.

10. The vector of claim 8, wherein the PMC virus expressed from said vector is attenuated.

11. A kit for demonstrating the presence of PMC virus comprising:

(a) a predetermined amount of at least one labelled nucleic acid sequence derived from the PMC virus, wherein said nucleic acid sequence comprises an isolated RNA or DNA nucleotide sequence according to claim 1; and (b) directions for use of said kit.

12. A recombinant expression vector comprising an isolated RNA or DNA nucleotide sequence of claim 1, operably linked to prokaryotic, eukaryotic or viral transcription and translation control elements.

13. An isolated host cell transformed by the vector of claim 12.

14. A method for preparing a PMC virus amino acid sequence encoded by an isolated RNA or DNA nucleotide sequence according to claim 1, comprising the steps of:

(a) culturing a host cell containing a vector according to claim 12 under conditions that provide for expression of the PMC virus amino acid sequence; and (b) recovering the expressed PMC virus sequence.

15. The composition of claim 7 wherein the composition further comprises a pharmaceutically acceptable carrier or diluent and/or an adjuvant.

16. A method of inducing an immune response in an animal comprising the steps of: providing an immunogenic composition according to claim 7 to the animal in an amount effective for producing an immune response.

17. The method of claim 16 wherein the immunogenic composition is administered by a method selected from the group consisting of: intravenously, subcutaneously, intramuscularly, intraorbitally, ophthalmically, intraventricularly, intracranially, intracapsularly, intraspinally, intracisternally, intraperitoneally, buccal, rectally, vaginally, intranasally, orally and aerosol administration.

18. A method for preparing a PMC virus amino acid sequence, comprising the steps of:

(a) culturing a host cell containing a vector according to claim 12 under conditions that provide for expression of the PMC virus amino acid sequence; and (b) recovering the expressed PMC virus sequence.

* * * * *

SEQUENCE LISTING

```
<160> NUMBER OF SEQ ID NOS: 89

<210> SEQ ID NO 1
<211> LENGTH: 12077
<212> TYPE: DNA
<213> ORGANISM: PMC Virus

<400> SEQUENCE: 1

gtataacgac agtagttcaa gtgtcgttat gcatcattgg ccataacaaa ttatctaatt      60

tggaataggg acctgcgacc tgtacgaagg ccgagcgtcg gtagccattc cgactagtag     120

gactagtaca aataggtcaa ctggttgagc aggtgagtgt gctgcagcgg ctaagcggtg     180

agtacaccgt attcgtcaac aggtgctact ggaaaggatc acccactagc gatgcctgtg     240

tggacgagga catgtccaag ccaatgttat cagtagcggg ggtcgttact gagaaagctg     300

cccagaatgg gtagttgcac atacagtctg ataggatgcc ggcggatgcc ctgtattttg     360

accagtataa atattatccg ttgtaaagca tatgaatact tttactttta atacatatgg     420

agggagtgag gaaggaaaca tgttctttag aactgcaccc acgccgccac cagggtgcca     480

agaaccggtt tacacaagca caatgagacc aatttttggc gaaccccatc cacctctaca     540

caaacacagc acgttaaaat tgccacattg gagggggatc aaaacaatta gagttaagaa     600

gagagaattg ccaaagaagg gcgattgtag caactcaaca acagctccca cttcgggggt     660

gtacgttgaa ttaggggctg tgttctataa agattacacg ggcacggtat accatcgtgt     720

accgctagaa ctttgtacaa accaagagag gtgcgaggga tccaagtgtg tagggagaat     780

gacagggtct gatggcaggt tgtacaacgt tttagtatgt ccggacgatt gtatcctctt     840

tgagagacac tgtagaggtc aaacagtcgt cctgaaatgg atttccaacc ccttgacatc     900

accactttgg gtccagagtt gttctgacga caaaggagca aaacccaagg tgaaaccaaa     960
```

-continued

```
agacgacagg atgaagcaag gaaaaatagt gacaaagcct aaagagactg aagcagatca   1020
aaaaactaga ccaccagatg ccacgatagt ggttgacggg cagaagtatc aggtgaggaa   1080
gaaggggaaa gcgaaaccca agactcaaga cggcttatac cacaacaaga acaaaccaga   1140
agcgtccagg aagaagcttg agaaggcctt gctagcatgg gcaatattag cctgcctatt   1200
ggtggtaccg gtagggtcca ccaacgtgac acaatggaac ttatgggaca ataaaagtac   1260
tacagacata catagcgtca tgttttctag agggattaaa aggagtctgc atggaatttg   1320
gcccacacaa atctgcaaag ggatccctac acatctagca gcagactatg aactgaaaag   1380
gattcacggg atggtggatg caagccccat gaccaacttc acatgttgta ggctacagag   1440
acatgagtgg aacaagcatg ggtggtgcaa ctggtacaat atagagccgt ggatcaatct   1500
catgaataat acccaaggac tattaaacac tggagacaat ttcactgagt gcgcagtcac   1560
atgcaggtat gatgcagact taggggtgaa tatagtgact caagccagga ctactccaac   1620
tatcctgact ggctgtaaga aagggcacaa cttctctttc tcaggggagg tcagggcctc   1680
accctgcaac tttgagttaa ctgctgaaga cttgctcagg atcatggatc acaccaactg   1740
cgagggattt acctacttcg gggaaggaat cgttgacggt tacaccgagg tagtagagaa   1800
ggccaggtca agtggtttca gggctctcac atggttgtcg agtaagattg aaaacaccaa   1860
gaaaaaaata ttcggagctg aagccagtcc ttactgccca gtggctaaga gggtcttcaa   1920
cattatttat accaacaatt gcaccccgct tggactgcca gataagtcaa aaattatagg   1980
accaggaacc tttgacatca gtggcaggga tgaattcata tttccaaaac tcccctacca   2040
cgtagatgac ttcattctac tgagcttaat tgcaatgtct gattttgctc cagagacatc   2100
aagtataatc tacctggctt tgcactacct aatgccaagt aatgacaaca gggacttcgt   2160
gatggacctg gacccaaata aactaaacct tactgcaact aaatccgtgg caagtgtggt   2220
ccctacatcg gtgaatgtgt taggtgaatg ggtgtgcgtc aaaccaagtt ggtggcctta   2280
ttccgccgaa atcactaatc tgataggagg tgtcatcacc gtggcagact tagttatcaa   2340
gaccattgaa gaattgctaa atttgtggac cgaagcaaca gctgtggcat ttctggctgc   2400
tctaataaaa atttttagag gccagccgat ccaagcggta gcatggttaa tcatcatagg   2460
gggagcacaa gcccaaacct gcaaccctga attcatgtac gcattagcga aaaataccag   2520
cataggttca ttaggaccag aatcactgac gacaaggtgg taccaactaa ccagcggttt   2580
caaactcact gacagcacga ttgaagtcac ctgtgtgggt gctaacatga ggattcatgt   2640
agtgtgccca cttgtaagtg acagatattt ggccataaac caccctagag cactgccaac   2700
aacggcgtgg ttcaggaaaa tacacactca gcatgaggta ccaagagaaa gaatcatgag   2760
tgagtcaaaa aggaggtaca cttgtccttg tggttctaaa ccagtggtga ggtcaacaac   2820
acaattcaac ccaatatcta tatctacccc aagctttgaa cttgaatgcc ctaggggttg   2880
gactggggct gtagagtgta cactagtctc cccatcaact ctgacaacag agactatatt   2940
cacatacagg aagcccaaac cattcggact tgaaaactgg tgcaagtata cagtggtgga   3000
gaaagggatc ctgtattctt gtaaatttgg gggcaattca acatgcatca aagggcttat   3060
agttaaaggg caacgggaag acaaagtaag gtactgtgaa tggtgtggtt ataagttcag   3120
ttcaccaaat ggactgcctc agtatccact gggattgtgt gagaaagaac aatcagaagg   3180
actcagggat tatggtgact tcccatgctg caacaacggc acttgtattg acaaagaagg   3240
tagtgtgcaa tgctacatag gggataagaa agttaccgtg aagctgtata atgcctcact   3300
attggccccc atgccctgca aacccatagt gtataactcc caggggcccc cagcgcctaa   3360
```

-continued

```
gacctgcact tataggtggg cctcaacatt agaaaataaa tattatgaac ccagggacag   3420
ctactaccag caatacatta taaagtcagg gtatcaatat tggtttgatc tcacagcaaa   3480
ggatcatgtg gcagactgga tcacaaaata ctttccaata ataatagtgg ccttgttagg   3540
gggcagaggc accttgtggg tgttgatagc ttatgagttg ctaactcagt atgaggtagt   3600
aggagacgag aacatagtgg ctcaagctga agccctggta atcggaaaca tcttgatgag   3660
tttagactta gagataatta gctgcttcct tctgttgttg atcgtggtga aaaaacaagc   3720
tgtcaggaga acgttggctt tactgtttca ttggataact atgaacccat tccagtcagt   3780
aatgatcaca gtggtctact tcgtcggttt ggtgagggcc gaagagggaa ctaaagaggg   3840
tagtacaagc gggccaccaa tccatgtagt tgcaatactg ttattcctct tgtaccacac   3900
agtgaagtat aaggacttta acatagcaat gatcttactt ataacattgt ccctgaaaag   3960
ctcatcctac atacatacca gcttgtatga aattccattg cttgtggctg taataagtct   4020
cacatgctcc atatacattt ttgacttgca ggtaaagagc aagctagtgg ccccaactat   4080
aggtataatt ggagttaccc tagcaatgag agttttgtgg ctggtaaggc aaatgactat   4140
accaaccccc tctgtgtcca ttagtctgat agatccaaag atggtcataa tactctactt   4200
gatatcccta actattacag tcaatcacaa cctagaccta gcaagttatt gcttgaaact   4260
gggacctttt atcctatcat tcctaacaat gtgggtggat gttgtcatcc tcctgctcat   4320
gctgccttgg tacgaactag taaaagtcta ctacctaaaa aagaagaaag aggatgtgga   4380
aacatggttc caaaattcag gaatatccac ccaagaaact tccccatacg gatttgattt   4440
ttctagcccc ggggagggag tgcacacact accaatgcaa aataaaacca aattttgtag   4500
gactgcttac atgactgtac taagggcttt ggtgataaca gccatcagca gtgtctggaa   4560
accaataatt ttagcagaac tcctaataga ggcagtgtat tggacacaca ttaaaatagc   4620
caaagaattg gcggggtcaa gcaggttcgt tgctaggttc attgcatcta ttatagagtt   4680
gaattgggcc atggacgaaa aagaagcatc tcggtacaaa agattttacc tattatcatc   4740
caaaataaca gatctaatgg ttaagcacaa aatccaaaat gagacagtaa aatcctggtt   4800
tgaagaaact gaaatatttg gaatacaaaa agtggcaatg gtgataaggg ctcattctct   4860
gagtttggag ccaaatgcca tcctttgctc cgtttgtgaa gaaaaacaaa atcaaaaagc   4920
caaaaggccc tgccctaagt gtggtagtag aggcactcaa ataaagtgtg ggctgacact   4980
ggccgagttt gaggaagaac attacaaaaa aatatacatc ctcgaaggcc aagatgaaac   5040
tcccatgagg aaagaagaaa gacagcaagt aacttatgtc tctaggggtg ctctgttcct   5100
taggaatctt cctatcttag cttcaaaaaa caaataccta cttgtaggca atctgggtat   5160
ggaattgcaa gatttggaaa gtatgggatg gatcattcga gggccagccg tctgcaagaa   5220
gataatacac catgagaaat gcaggccttc aataccagac aaactcatgg cattcttcgg   5280
gattatgcct aggggagtta caccaagagc ccctacacgg ttccctgtgt ccttgctgaa   5340
gataagacgg ggttttgaga ccggctgggc ctacacacac cctggagggg taagtagtgt   5400
gatgcatgtc accgctgggt cggatatata tgtcaatgac tcaataggga ggacaaaaat   5460
ccagtgccaa gacaaaaaca ctacaacaga tgagtgtgaa tatggtgtga aaacagactc   5520
agggtgctct gatggagctc ggtgctatgt catcaaccct gaagcaacca acatagcagg   5580
gaccaagggg gccatggtac acctgaggaa agctggagga gagttcaact gcgtgactgc   5640
ccagggtacc cccgccttct ataatctaaa gaacttaaaa ggatggtcag gcctgcctat   5700
ctttgaagct gccacaggaa gagtggtagg aagggtaaaa gcaggaaaaa acactgacaa   5760
```

-continued

```
tgctccaaca accattatgt cagggacgca agtggcaaaa ccatcagagt gtgacctaga   5820
atcagtggtg aggaaactag agacaatgaa cagaggggaa ttcaaacaag tgactctggc   5880
tacaggcgca ggaaagacaa ccatgctacc aaagctgtta atagaatcca taggcaggca   5940
taagagagtg ttagtactga tcccgttgag agctgcagcg gagggggtgt accagtacat   6000
gagaaccaaa cacccaagca tatctttcaa cttgaggata ggggatctga aagaaggtga   6060
catggcaact gggatcacct atgcctctta tgggtacttc tgccaaatgg acatgcctag   6120
actggagaat gcaatgaagg aataccacta tattttcttg gatgaatatc actgtgccac   6180
accagaacag ttggcagtga tgtcaaaaat acataggttc ggtgaatcag ttagggtaat   6240
agccatgacc gccacgccat ccgggactgt gagcacaaca gggcagaaat tcacaattga   6300
ggaggtggta gtacctgaag tgatgaaggg ggaggacctt gctgatgatt acatcgaaat   6360
agcagggttg aaggtgccaa agaaagagtt agagggtaac gtactgactt ttgtgcctac   6420
aaggaagatg gcatcggaaa cagcaaaaaa attaaccaca cagggataca atgctggata   6480
ctacttcagt ggagaagatc catcatccct gcggacaact acttctaagt caccatatat   6540
agtagttgca accaatgcca ttgaatccgg ggtaacctta ccggaccttg atacagtaat   6600
agatacaggc atgaagtgtg aaaagagact aagaatcgaa aacaaagctc cctacatcgt   6660
aacaggactg aaaagaatgg ctataacaac gggggagcaa gctcaaagaa aaggtagggt   6720
aggcagggtt aaacctggga ggtacttgag aggacctgaa aacactgcag gtgaaaagga   6780
ctatcactat gaccttttac aggcacagag gtacggcatc caagactcaa taaacatcac   6840
caagtctttc agggagatga actatgattg ggcattatat gaggaagacc cgttaaagat   6900
tgcccaatta gagttgctaa acacactcct gatctcaagg gatctgccag tagtaacaaa   6960
aaatctgatg gcccgcacaa cacatcccga acctatacaa ttggcttaca atagtttaga   7020
aacccctgta ccggtggcat tcccaaaagt gaaaaatgga gaagtcactg acgcacatga   7080
aacttacgag ttgatgacct gtaggaagct tgagaaagac ccccctatat acctgtatgc   7140
aacagaagaa gaagatctcg tagtggacat actgggattg aaatggccag acgccacaga   7200
gagggctgtc ttggaagtgc aagacgccct gggccagatc acaggtttat ctgcagggga   7260
gacagcttta ctcatagccc tattagggtg ggtgggctac gaagccttgg tgaagaggca   7320
cgtgcctatg gtgacagaca tatacaccct agaagatgaa aaattggaag acactacaca   7380
cctacaattt gccccagatg atctgaacaa ttcagatacc attgagctcc aagacttatc   7440
gaatcaccaa atccaacaaa ttctagaagg tgggaaggaa tatgtcggcc aagcctacca   7500
attcctcagg ttgcaagctg agagggctgc caactcagac aaaggcaaga aagcaatggc   7560
agcggcccca ttactagccc acaagttcct ggaatacttg caagagcatg caggtgacat   7620
aaagaagtat ggtctatggg gggtccacac agcattgtat aacagcataa aagaaagact   7680
gggtcacgaa actgcattcg catctctggt tataaaatgg attgcctttt cctcagatgg   7740
agtcccgggg atgattaagc aagcagcagt agacttggtg gtatactata taatcaacag   7800
gcctgagtat caaggggata aggagacaca gaatgcaggt agacaatttg ttggctccct   7860
ttttgtttca tgtctagcag agtacacatt caaaaacttc aataaatcag cattagaagg   7920
attgatcgag cctgccttaa gctatctacc ctacgcttca agcgcactaa agttattcct   7980
accgactaga cttgaaagtg tagtgatact gtccactact atatacagaa catacttatc   8040
aatcaggaaa ggatctagtc agggtttagc cgggctggca gttagctcag cgatggagat   8100
catgaaccag aacccaatca gcgtggctat tgcactggca ctaggagtcg gagcaatagc   8160
```

-continued

```
ggcacataat gccattgaga gcagtgaggc aaaaaggact ctcctgatga aggtctttgt   8220
taagaacttt ttggaccaag cagccactga tgagcttgtg aaagagaacc ctgagaagat   8280
cataatggca gtgtttgagg gcattcaaac agctggaaat ccattgagac ttgtatacca   8340
tctatatgca atgttctaca aagggtggac tgccgcggaa atagctgaaa aaaccgctgg   8400
taggaacatt tttgtgttaa caatatttga aggattggaa atgttaggcc tggatgccga   8460
ctcaaaatgg agaaatctga gctctaatta tcttattgat gcagtgaaga aaatcattga   8520
aaaaatgact aaaacagcaa caagcttcac ctacagcttt ttgaaatctt tgcttcctgc   8580
cccttctcg tgtactaaat cagaaagaga tccaagaata gggtggcccc aaaaagacta   8640
cgactacctc gaggtccgat gcgcttgtgg gtataacagg agagctataa aaagagactc   8700
aggacctgtg ttatgggaga ccttagagga gacgggtcca gagtactgcc acaacagagg   8760
tgaaaggggg ctcagcaatg tgaagactac tagatgcttt gtccaaggag aggaaatccc   8820
tccaattgca ctgaggaaag gagtaggtga gatgttggtc aagggtgttt cattcagaat   8880
agattttgat aaagacaaga tactttcaac agacaagtgg aaggtaccac atagggcagt   8940
tacatcaatc tttgaggatt ggcagggtat tggttacaga gaggcttacc tagggaccaa   9000
accagactat gggggtctgg tgcccagatc ttgtgtaact gtaacaaaac aagggttaac   9060
attcttgaaa actgccagag gcatggcttt cacgactgac ctgaccatcc agaacatcaa   9120
aatgctgata gctacatgct tcaagaacaa ggtgaaggaa ggggagatac cagctacgat   9180
tgaaggggaa acatggatca acataccact agtgaatgag gacaccggga ccattaaacc   9240
aagcttcggg gaaagagtga ttcccgaacc atatgaggag gacccacttg aaggcccaag   9300
tgtaatcgtt gaaacaggag gcatagccat caaccaaata ggggtcaatc cacaatccag   9360
tacatgtgga acagttttta cagcagtgaa ggatctgtgc caaacagtta gtaataaagc   9420
caagaatatc aaaattgggt tttcggaagg ccaataccca ggtccagggg ttgcaaagaa   9480
gacactgaac cagctcatac aagatgaaga cccaaaacca ttcatatttg tttgtggctc   9540
tgacaagtca atgtctaatc gggcaaaaac tgcgaggaac atcaagagaa tcaccaccac   9600
aacacctgag aaattcagag acttggcaaa aaacaagaaa ttgataattg tgctgttagg   9660
tgatagatac catgaagata tagaaaagta tgcagacttc aagggcacct tcttgaccag   9720
acaaaccttg gaagcactag caagtgccaa agctgtagag aaggacatga ccaagaaaga   9780
agcagcaaga gtattggcaa tggaagaaaa ggatgaacta gaactcccag ggtggctgca   9840
tacagatgca cccaaattcc tagacattac taaggacaac atcacacatc acctaatagg   9900
ggacatgcag agtctgagag aaagagcagg ggagatagga gcaaaggcca ccactcaaat   9960
cactaagaaa gggagtgtat acacaatcaa tctgagtacg tggtgggagt cagagaggtt  10020
ggcatctttg gaacctttgt tccgggaact actatctaaa tgcaggccag tggacaggga  10080
gacatataag aattgtcatt ttgcaacagc agcccaactt gccggaggaa actgggtacc  10140
ggtagcacca gttgtacatc ttggggaaat tccggtaaag aagaaaaaga ctctccccta  10200
cgaggcatac aagctcctaa aagagatggt tgactcggag aaggaattcc ataaaccagt  10260
gagcagggaa aaacaccaat ggatactgaa caaagtgaaa actggtggtg acctcggctt  10320
aaaaaatcta gtatgtccag gtagggttgg agaaccaatc ctaagagaga agaagaaatt  10380
caacatttac aacaagagga ttaccagtac tatgttatca gtagggataa ggccagaaaa  10440
attgccagtg gtaagagccc agaccagtac caaagaattt catgaagcaa taagggacaa  10500
aatagacaaa aaagcaaaca cacagacccc aggcctacac aaagaattgt tggagatatt  10560
```

-continued

```
caactcaata tgtgccatcc ccgaacttag aaatacctac aaagaggttg attgggacgt  10620

tctaacctca ggcataaata ggaaaggtgc agccgggtac ttcgaaaaaa tgaacatagg  10680

ggagatcata gatagtgaca aaaaatcagt ggaacaactc ataaagagaa tgaaatcagg  10740

gctagaattc aactactatg agactgcaat accaaaaaat gagaagaggg cagtggtaga  10800

tgattggatg gaaggtgact atgtagaaga aaaaagacca agagtcatac agtatcctga  10860

ggcaaagatg agattagcta taaccaaagt aatgtataac tgggtcaagc agaagcctat  10920

agtaatccct ggatacgaag gtaagactcc tttgtttcat gttttcgaca aggtccacaa  10980

agaatggaaa aatttcaaca gtccagttgc agtcagtttt gacactaaag cctgggacac  11040

acaagtaaca cccaaagacc ttctcctcat atcagaaatc caaaagtatt attacaagaa  11100

agaataccat agattcatag ataatttgac cgagaaaatg gtggaggtac cagtggtttg  11160

tgaagacgga aacgtctaca taagagaagg tcagagggga agtggtcaac cagacactag  11220

cgcaggtaat agtatgttga atgtactgac tatgatatat gccttctgca aagctaactc  11280

catcccttac tcagccttcc acagggtagc aaagatacat gtgtgtggag atgatggttt  11340

cttgataact gagaaaagtt ttggtgaggc ctttgcgatc aaggggcctc aaattttgat  11400

ggaagcagga aaaccacaaa aacttatagg tgaatttgga ctgaaattgg catataaatt  11460

tgatgacatt gaattttgct cgcatacacc aataaaggtc aggtgggctg acaacaacac  11520

atcatacatg cccggaagag acacagctac cattctagct aaaatggcaa cccgccttga  11580

ctctagtggg gagaggggga ccgagggata cgagctggcc gtggccttca gtttcttact  11640

aatgtattct tggaaccccc tggtaagaag aatatgcctg cttgtcatgt ctacaattga  11700

cacaaaagaa gctagccaaa ataacactat atatacattt agggggggatc ccataggtgc  11760

ctacacagag gtaattgggt ataggctgga ccaactaaaa cagacagagt tctctaaatt  11820

ggctcagctg aatttgtcaa tggcaatact tcaaatatac aataaaaaca caaccaagag  11880

actcatcgaa gattgtgtga aacttggcaa ccaaaataag caaatattgg tgaatgcaga  11940

ccgtttgatc agcaagaaaa cgggctacac atatgagcca acagctggcc acactaagat  12000

aggcaagcac tatgaagaaa tcaacctgct gaaagataca ccacaaaaaa ctgtctacca  12060

aggaactgaa aggtata                                                 12077
```

<210> SEQ ID NO 2
<211> LENGTH: 3886
<212> TYPE: PRT
<213> ORGANISM: PMC Virus

<400> SEQUENCE: 2

```
Gly Gly Ser Glu Glu Gly Asn Met Phe Phe Arg Thr Ala Pro Thr Pro
1               5                   10                  15

Pro Pro Gly Cys Gln Glu Pro Val Tyr Thr Ser Thr Met Arg Pro Ile
            20                  25                  30

Phe Gly Glu Pro His Pro Pro Leu His Lys His Ser Thr Leu Lys Leu
        35                  40                  45

Pro His Trp Arg Gly Ile Lys Thr Ile Arg Val Lys Lys Arg Glu Leu
    50                  55                  60

Pro Lys Lys Gly Asp Cys Ser Asn Ser Thr Thr Ala Pro Thr Ser Gly
65                  70                  75                  80

Val Tyr Val Glu Leu Gly Ala Val Phe Tyr Lys Asp Tyr Thr Gly Thr
                85                  90                  95

Val Tyr His Arg Val Pro Leu Glu Leu Cys Thr Asn Gln Glu Arg Cys
            100                 105                 110
```

```
Glu Gly Ser Lys Cys Val Gly Arg Met Thr Gly Ser Asp Gly Arg Leu
        115                 120                 125

Tyr Asn Val Leu Val Cys Pro Asp Asp Cys Ile Leu Phe Glu Arg His
    130                 135                 140

Cys Arg Gly Gln Thr Val Val Leu Lys Trp Ile Ser Asn Pro Leu Thr
145                 150                 155                 160

Ser Pro Leu Trp Val Gln Ser Cys Ser Asp Asp Lys Gly Ala Lys Pro
                165                 170                 175

Lys Val Lys Pro Lys Asp Asp Arg Met Lys Gln Gly Lys Ile Val Thr
            180                 185                 190

Lys Pro Lys Glu Thr Glu Ala Asp Gln Lys Thr Arg Pro Pro Asp Ala
        195                 200                 205

Thr Ile Val Val Asp Gly Gln Lys Tyr Gln Val Arg Lys Lys Gly Lys
    210                 215                 220

Ala Lys Pro Lys Thr Gln Asp Gly Leu Tyr His Asn Lys Asn Lys Pro
225                 230                 235                 240

Glu Ala Ser Arg Lys Lys Leu Glu Lys Ala Leu Leu Ala Trp Ala Ile
                245                 250                 255

Leu Ala Cys Leu Leu Val Val Pro Val Gly Ser Thr Asn Val Thr Gln
            260                 265                 270

Trp Asn Leu Trp Asp Asn Lys Ser Thr Thr Asp Ile His Ser Val Met
        275                 280                 285

Phe Ser Arg Gly Ile Lys Arg Ser Leu His Gly Ile Trp Pro Thr Gln
    290                 295                 300

Ile Cys Lys Gly Ile Pro Thr His Leu Ala Ala Asp Tyr Glu Leu Lys
305                 310                 315                 320

Arg Ile His Gly Met Val Asp Ala Ser Pro Met Thr Asn Phe Thr Cys
                325                 330                 335

Cys Arg Leu Gln Arg His Glu Trp Asn Lys His Gly Trp Cys Asn Trp
            340                 345                 350

Tyr Asn Ile Glu Pro Trp Ile Asn Leu Met Asn Asn Thr Gln Gly Leu
        355                 360                 365

Leu Asn Thr Gly Asp Asn Phe Thr Glu Cys Ala Val Thr Cys Arg Tyr
    370                 375                 380

Asp Ala Asp Leu Gly Val Asn Ile Val Thr Gln Ala Arg Thr Thr Pro
385                 390                 395                 400

Thr Ile Leu Thr Gly Cys Lys Lys Gly His Asn Phe Ser Phe Ser Gly
                405                 410                 415

Glu Val Arg Ala Ser Pro Cys Asn Phe Glu Leu Thr Ala Glu Asp Leu
            420                 425                 430

Leu Arg Ile Met Asp His Thr Asn Cys Glu Gly Phe Thr Tyr Phe Gly
        435                 440                 445

Glu Gly Ile Val Asp Gly Tyr Thr Glu Val Val Glu Lys Ala Arg Ser
    450                 455                 460

Ser Gly Phe Arg Ala Leu Thr Trp Leu Ser Ser Lys Ile Glu Asn Thr
465                 470                 475                 480

Lys Lys Lys Ile Phe Gly Ala Glu Ala Ser Pro Tyr Cys Pro Val Ala
                485                 490                 495

Lys Arg Val Phe Asn Ile Ile Tyr Thr Asn Asn Cys Thr Pro Leu Gly
            500                 505                 510

Leu Pro Asp Lys Ser Lys Ile Ile Gly Pro Gly Thr Phe Asp Ile Ser
        515                 520                 525

Gly Arg Asp Glu Phe Ile Phe Pro Lys Leu Pro Tyr His Val Asp Asp
```

-continued

```
    530                 535                 540

Phe Ile Leu Leu Ser Leu Ile Ala Met Ser Asp Phe Ala Pro Glu Thr
545                 550                 555                 560

Ser Ser Ile Ile Tyr Leu Ala Leu His Tyr Leu Met Pro Ser Asn Asp
                565                 570                 575

Asn Arg Asp Phe Val Met Asp Leu Asp Pro Asn Lys Leu Asn Leu Thr
            580                 585                 590

Ala Thr Lys Ser Val Ala Ser Val Val Pro Thr Ser Val Asn Val Leu
        595                 600                 605

Gly Glu Trp Val Cys Val Lys Pro Ser Trp Trp Pro Tyr Ser Ala Glu
    610                 615                 620

Ile Thr Asn Leu Ile Gly Gly Val Ile Thr Val Ala Asp Leu Val Ile
625                 630                 635                 640

Lys Thr Ile Glu Glu Leu Leu Asn Leu Trp Thr Glu Ala Thr Ala Val
                645                 650                 655

Ala Phe Leu Ala Ala Leu Ile Lys Ile Phe Arg Gly Gln Pro Ile Gln
            660                 665                 670

Ala Val Ala Trp Leu Ile Ile Ile Gly Gly Ala Gln Ala Gln Thr Cys
        675                 680                 685

Asn Pro Glu Phe Met Tyr Ala Leu Ala Lys Asn Thr Ser Ile Gly Ser
    690                 695                 700

Leu Gly Pro Glu Ser Leu Thr Thr Arg Trp Tyr Gln Leu Thr Ser Gly
705                 710                 715                 720

Phe Lys Leu Thr Asp Ser Thr Ile Glu Val Thr Cys Val Gly Ala Asn
                725                 730                 735

Met Arg Ile His Val Val Cys Pro Leu Val Ser Asp Arg Tyr Leu Ala
            740                 745                 750

Ile Asn His Pro Arg Ala Leu Pro Thr Thr Ala Trp Phe Arg Lys Ile
        755                 760                 765

His Thr Gln His Glu Val Pro Arg Glu Arg Ile Met Ser Glu Ser Lys
    770                 775                 780

Arg Arg Tyr Thr Cys Pro Cys Gly Ser Lys Pro Val Val Arg Ser Thr
785                 790                 795                 800

Thr Gln Phe Asn Pro Ile Ser Ile Ser Thr Pro Ser Phe Glu Leu Glu
                805                 810                 815

Cys Pro Arg Gly Trp Thr Gly Ala Val Glu Cys Thr Leu Val Ser Pro
            820                 825                 830

Ser Thr Leu Thr Thr Glu Thr Ile Phe Thr Tyr Arg Lys Pro Lys Pro
        835                 840                 845

Phe Gly Leu Glu Asn Trp Cys Lys Tyr Thr Val Val Glu Lys Gly Ile
    850                 855                 860

Leu Tyr Ser Cys Lys Phe Gly Gly Asn Ser Thr Cys Ile Lys Gly Leu
865                 870                 875                 880

Ile Val Lys Gly Gln Arg Glu Asp Lys Val Arg Tyr Cys Glu Trp Cys
                885                 890                 895

Gly Tyr Lys Phe Ser Ser Pro Asn Gly Leu Pro Gln Tyr Pro Leu Gly
            900                 905                 910

Leu Cys Glu Lys Glu Gln Ser Glu Gly Leu Arg Asp Tyr Gly Asp Phe
        915                 920                 925

Pro Cys Cys Asn Asn Gly Thr Cys Ile Asp Lys Glu Gly Ser Val Gln
    930                 935                 940

Cys Tyr Ile Gly Asp Lys Lys Val Thr Val Lys Leu Tyr Asn Ala Ser
945                 950                 955                 960
```

-continued

```
Leu Leu Ala Pro Met Pro Cys Lys Pro Ile Val Tyr Asn Ser Gln Gly
                965                 970                 975

Pro Pro Ala Pro Lys Thr Cys Thr Tyr Arg Trp Ala Ser Thr Leu Glu
            980                 985                 990

Asn Lys Tyr Tyr Glu Pro Arg Asp  Ser Tyr Tyr Gln Gln  Tyr Ile Ile
        995                 1000                 1005

Lys Ser  Gly Tyr Gln Tyr Trp  Phe Asp Leu Thr Ala  Lys Asp His
    1010                 1015                 1020

Val Ala  Asp Trp Ile Thr Lys  Tyr Phe Pro Ile Ile  Ile Val Ala
    1025                 1030                 1035

Leu Leu  Gly Gly Arg Gly Thr  Leu Trp Val Leu Ile  Ala Tyr Glu
    1040                 1045                 1050

Leu Leu  Thr Gln Tyr Glu Val  Val Gly Asp Glu Asn  Ile Val Ala
    1055                 1060                 1065

Gln Ala  Glu Ala Leu Val Ile  Gly Asn Ile Leu Met  Ser Leu Asp
    1070                 1075                 1080

Leu Glu  Ile Ile Ser Cys Phe  Leu Leu Leu Leu Ile  Val Val Lys
    1085                 1090                 1095

Lys Gln  Ala Val Arg Arg Thr  Leu Ala Leu Leu Phe  His Trp Ile
    1100                 1105                 1110

Thr Met  Asn Pro Phe Gln Ser  Val Met Ile Thr Val  Val Tyr Phe
    1115                 1120                 1125

Val Gly  Leu Val Arg Ala Glu  Glu Gly Thr Lys Glu  Gly Ser Thr
    1130                 1135                 1140

Ser Gly  Pro Pro Ile His Val  Val Ala Ile Leu Leu  Phe Leu Leu
    1145                 1150                 1155

Tyr His  Thr Val Lys Tyr Lys  Asp Phe Asn Ile Ala  Met Ile Leu
    1160                 1165                 1170

Leu Ile  Thr Leu Ser Leu Lys  Ser Ser Ser Tyr Ile  His Thr Ser
    1175                 1180                 1185

Leu Tyr  Glu Ile Pro Leu Leu  Val Ala Val Ile Ser  Leu Thr Cys
    1190                 1195                 1200

Ser Ile  Tyr Ile Phe Asp Leu  Gln Val Lys Ser Lys  Leu Val Ala
    1205                 1210                 1215

Pro Thr  Ile Gly Ile Ile Gly  Val Thr Leu Ala Met  Arg Val Leu
    1220                 1225                 1230

Trp Leu  Val Arg Gln Met Thr  Ile Pro Thr Pro Ser  Val Ser Ile
    1235                 1240                 1245

Ser Leu  Ile Asp Pro Lys Met  Val Ile Ile Leu Tyr  Leu Ile Ser
    1250                 1255                 1260

Leu Thr  Ile Thr Val Asn His  Asn Leu Asp Leu Ala  Ser Tyr Cys
    1265                 1270                 1275

Leu Lys  Leu Gly Pro Phe Ile  Leu Ser Phe Leu Thr  Met Trp Val
    1280                 1285                 1290

Asp Val  Val Ile Leu Leu Leu  Met Leu Pro Trp Tyr  Glu Leu Val
    1295                 1300                 1305

Lys Val  Tyr Tyr Leu Lys Lys  Lys Lys Glu Asp Val  Glu Thr Trp
    1310                 1315                 1320

Phe Gln  Asn Ser Gly Ile Ser  Thr Gln Glu Thr Ser  Pro Tyr Gly
    1325                 1330                 1335

Phe Asp  Phe Ser Ser Pro Gly  Glu Gly Val His Thr  Leu Pro Met
    1340                 1345                 1350

Gln Asn  Lys Thr Lys Phe Cys  Arg Thr Ala Tyr Met  Thr Val Leu
    1355                 1360                 1365
```

-continued

```
Arg Ala  Leu Val Ile Thr Ala  Ile Ser Ser Val Trp  Lys Pro Ile
    1370                 1375                 1380

Ile Leu  Ala Glu Leu Leu Ile  Glu Ala Val Tyr Trp  Thr His Ile
    1385                 1390                 1395

Lys Ile  Ala Lys Glu Leu Ala  Gly Ser Ser Arg Phe  Val Ala Arg
    1400                 1405                 1410

Phe Ile  Ala Ser Ile Ile Glu  Leu Asn Trp Ala Met  Asp Glu Lys
    1415                 1420                 1425

Glu Ala  Ser Arg Tyr Lys Arg  Phe Tyr Leu Leu Ser  Ser Lys Ile
    1430                 1435                 1440

Thr Asp  Leu Met Val Lys His  Lys Ile Gln Asn Glu  Thr Val Lys
    1445                 1450                 1455

Ser Trp  Phe Glu Glu Thr Glu  Ile Phe Gly Ile Gln  Lys Val Ala
    1460                 1465                 1470

Met Val  Ile Arg Ala His Ser  Leu Ser Leu Glu Pro  Asn Ala Ile
    1475                 1480                 1485

Leu Cys  Ser Val Cys Glu Glu  Lys Gln Asn Gln Lys  Ala Lys Arg
    1490                 1495                 1500

Pro Cys  Pro Lys Cys Gly Ser  Arg Gly Thr Gln Ile  Lys Cys Gly
    1505                 1510                 1515

Leu Thr  Leu Ala Glu Phe Glu  Glu Glu His Tyr Lys  Lys Ile Tyr
    1520                 1525                 1530

Ile Leu  Glu Gly Gln Asp Glu  Thr Pro Met Arg Lys  Glu Glu Arg
    1535                 1540                 1545

Gln Gln  Val Thr Tyr Val Ser  Arg Gly Ala Leu Phe  Leu Arg Asn
    1550                 1555                 1560

Leu Pro  Ile Leu Ala Ser Lys  Asn Lys Tyr Leu Leu  Val Gly Asn
    1565                 1570                 1575

Leu Gly  Met Glu Leu Gln Asp  Leu Glu Ser Met Gly  Trp Ile Ile
    1580                 1585                 1590

Arg Gly  Pro Ala Val Cys Lys  Lys Ile Ile His His  Glu Lys Cys
    1595                 1600                 1605

Arg Pro  Ser Ile Pro Asp Lys  Leu Met Ala Phe Phe  Gly Ile Met
    1610                 1615                 1620

Pro Arg  Gly Val Thr Pro Arg  Ala Pro Thr Arg Phe  Pro Val Ser
    1625                 1630                 1635

Leu Leu  Lys Ile Arg Arg Gly  Phe Glu Thr Gly Trp  Ala Tyr Thr
    1640                 1645                 1650

His Pro  Gly Gly Val Ser Ser  Val Met His Val Thr  Ala Gly Ser
    1655                 1660                 1665

Asp Ile  Tyr Val Asn Asp Ser  Ile Gly Arg Thr Lys  Ile Gln Cys
    1670                 1675                 1680

Gln Asp  Lys Asn Thr Thr Thr  Asp Glu Cys Glu Tyr  Gly Val Lys
    1685                 1690                 1695

Thr Asp  Ser Gly Cys Ser Asp  Gly Ala Arg Cys Tyr  Val Ile Asn
    1700                 1705                 1710

Pro Glu  Ala Thr Asn Ile Ala  Gly Thr Lys Gly Ala  Met Val His
    1715                 1720                 1725

Leu Arg  Lys Ala Gly Gly Glu  Phe Asn Cys Val Thr  Ala Gln Gly
    1730                 1735                 1740

Thr Pro  Ala Phe Tyr Asn Leu  Lys Asn Leu Lys Gly  Trp Ser Gly
    1745                 1750                 1755

Leu Pro  Ile Phe Glu Ala Ala  Thr Gly Arg Val Val  Gly Arg Val
```

-continued

```
    1760                1765                1770

Lys Ala  Gly Lys Asn Thr Asp  Asn Ala Pro Thr Thr  Ile Met Ser
    1775                1780                1785

Gly Thr  Gln Val Ala Lys Pro  Ser Glu Cys Asp Leu  Glu Ser Val
    1790                1795                1800

Val Arg  Lys Leu Glu Thr Met  Asn Arg Gly Glu Phe  Lys Gln Val
    1805                1810                1815

Thr Leu  Ala Thr Gly Ala Gly  Lys Thr Thr Met Leu  Pro Lys Leu
    1820                1825                1830

Leu Ile  Glu Ser Ile Gly Arg  His Lys Arg Val Leu  Val Leu Ile
    1835                1840                1845

Pro Leu  Arg Ala Ala Ala Glu  Gly Val Tyr Gln Tyr  Met Arg Thr
    1850                1855                1860

Lys His  Pro Ser Ile Ser Phe  Asn Leu Arg Ile Gly  Asp Leu Lys
    1865                1870                1875

Glu Gly  Asp Met Ala Thr Gly  Ile Thr Tyr Ala Ser  Tyr Gly Tyr
    1880                1885                1890

Phe Cys  Gln Met Asp Met Pro  Arg Leu Glu Asn Ala  Met Lys Glu
    1895                1900                1905

Tyr His  Tyr Ile Phe Leu Asp  Glu Tyr His Cys Ala  Thr Pro Glu
    1910                1915                1920

Gln Leu  Ala Val Met Ser Lys  Ile His Arg Phe Gly  Glu Ser Val
    1925                1930                1935

Arg Val  Ile Ala Met Thr Ala  Thr Pro Ser Gly Thr  Val Ser Thr
    1940                1945                1950

Thr Gly  Gln Lys Phe Thr Ile  Glu Glu Val Val Val  Pro Glu Val
    1955                1960                1965

Met Lys  Gly Glu Asp Leu Ala  Asp Asp Tyr Ile Glu  Ile Ala Gly
    1970                1975                1980

Leu Lys  Val Pro Lys Lys Glu  Leu Glu Gly Asn Val  Leu Thr Phe
    1985                1990                1995

Val Pro  Thr Arg Lys Met Ala  Ser Glu Thr Ala Lys  Lys Leu Thr
    2000                2005                2010

Thr Gln  Gly Tyr Asn Ala Gly  Tyr Tyr Phe Ser Gly  Glu Asp Pro
    2015                2020                2025

Ser Ser  Leu Arg Thr Thr Thr  Ser Lys Ser Pro Tyr  Ile Val Val
    2030                2035                2040

Ala Thr  Asn Ala Ile Glu Ser  Gly Val Thr Leu Pro  Asp Leu Asp
    2045                2050                2055

Thr Val  Ile Asp Thr Gly Met  Lys Cys Glu Lys Arg  Leu Arg Ile
    2060                2065                2070

Glu Asn  Lys Ala Pro Tyr Ile  Val Thr Gly Leu Lys  Arg Met Ala
    2075                2080                2085

Ile Thr  Thr Gly Glu Gln Ala  Gln Arg Lys Gly Arg  Val Gly Arg
    2090                2095                2100

Val Lys  Pro Gly Arg Tyr Leu  Arg Gly Pro Glu Asn  Thr Ala Gly
    2105                2110                2115

Glu Lys  Asp Tyr His Tyr Asp  Leu Leu Gln Ala Gln  Arg Tyr Gly
    2120                2125                2130

Ile Gln  Asp Ser Ile Asn Ile  Thr Lys Ser Phe Arg  Glu Met Asn
    2135                2140                2145

Tyr Asp  Trp Ala Leu Tyr Glu  Glu Asp Pro Leu Lys  Ile Ala Gln
    2150                2155                2160
```

-continued

```
Leu Glu  Leu Leu Asn Thr Leu  Leu Ile Ser Arg Asp  Leu Pro Val
    2165                 2170                 2175

Val Thr  Lys Asn Leu Met Ala  Arg Thr Thr His Pro  Glu Pro Ile
    2180                 2185                 2190

Gln Leu  Ala Tyr Asn Ser Leu  Glu Thr Pro Val Pro  Val Ala Phe
    2195                 2200                 2205

Pro Lys  Val Lys Asn Gly Glu  Val Thr Asp Ala His  Glu Thr Tyr
    2210                 2215                 2220

Glu Leu  Met Thr Cys Arg Lys  Leu Glu Lys Asp Pro  Pro Ile Tyr
    2225                 2230                 2235

Leu Tyr  Ala Thr Glu Glu Glu  Asp Leu Val Val Asp  Ile Leu Gly
    2240                 2245                 2250

Leu Lys  Trp Pro Asp Ala Thr  Glu Arg Ala Val Leu  Glu Val Gln
    2255                 2260                 2265

Asp Ala  Leu Gly Gln Ile Thr  Gly Leu Ser Ala Gly  Glu Thr Ala
    2270                 2275                 2280

Leu Leu  Ile Ala Leu Leu Gly  Trp Val Gly Tyr Glu  Ala Leu Val
    2285                 2290                 2295

Lys Arg  His Val Pro Met Val  Thr Asp Ile Tyr Thr  Leu Glu Asp
    2300                 2305                 2310

Glu Lys  Leu Glu Asp Thr Thr  His Leu Gln Phe Ala  Pro Asp Asp
    2315                 2320                 2325

Leu Asn  Asn Ser Asp Thr Ile  Glu Leu Gln Asp Leu  Ser Asn His
    2330                 2335                 2340

Gln Ile  Gln Gln Ile Leu Glu  Gly Gly Lys Glu Tyr  Val Gly Gln
    2345                 2350                 2355

Ala Tyr  Gln Phe Leu Arg Leu  Gln Ala Glu Arg Ala  Ala Asn Ser
    2360                 2365                 2370

Asp Lys  Gly Lys Lys Ala Met  Ala Ala Ala Pro Leu  Leu Ala His
    2375                 2380                 2385

Lys Phe  Leu Glu Tyr Leu Gln  Glu His Ala Gly Asp  Ile Lys Lys
    2390                 2395                 2400

Tyr Gly  Leu Trp Gly Val His  Thr Ala Leu Tyr Asn  Ser Ile Lys
    2405                 2410                 2415

Glu Arg  Leu Gly His Glu Thr  Ala Phe Ala Ser Leu  Val Ile Lys
    2420                 2425                 2430

Trp Ile  Ala Phe Ser Ser Asp  Gly Val Pro Gly Met  Ile Lys Gln
    2435                 2440                 2445

Ala Ala  Val Asp Leu Val Val  Tyr Tyr Ile Ile Asn  Arg Pro Glu
    2450                 2455                 2460

Tyr Gln  Gly Asp Lys Glu Thr  Gln Asn Ala Gly Arg  Gln Phe Val
    2465                 2470                 2475

Gly Ser  Leu Phe Val Ser Cys  Leu Ala Glu Tyr Thr  Phe Lys Asn
    2480                 2485                 2490

Phe Asn  Lys Ser Ala Leu Glu  Gly Leu Ile Glu Pro  Ala Leu Ser
    2495                 2500                 2505

Tyr Leu  Pro Tyr Ala Ser Ser  Ala Leu Lys Leu Phe  Leu Pro Thr
    2510                 2515                 2520

Arg Leu  Glu Ser Val Val Ile  Leu Ser Thr Thr Ile  Tyr Arg Thr
    2525                 2530                 2535

Tyr Leu  Ser Ile Arg Lys Gly  Ser Ser Gln Gly Leu  Ala Gly Leu
    2540                 2545                 2550

Ala Val  Ser Ser Ala Met Glu  Ile Met Asn Gln Asn  Pro Ile Ser
    2555                 2560                 2565
```

-continued

```
Val Ala  Ile Ala Leu Ala Leu  Gly Val Gly Ala Ile  Ala Ala His
    2570                 2575                 2580

Asn Ala  Ile Glu Ser Ser Glu  Ala Lys Arg Thr Leu  Leu Met Lys
    2585                 2590                 2595

Val Phe  Val Lys Asn Phe Leu  Asp Gln Ala Ala Thr  Asp Glu Leu
    2600                 2605                 2610

Val Lys  Glu Asn Pro Glu Lys  Ile Ile Met Ala Val  Phe Glu Gly
    2615                 2620                 2625

Ile Gln  Thr Ala Gly Asn Pro  Leu Arg Leu Val Tyr  His Leu Tyr
    2630                 2635                 2640

Ala Met  Phe Tyr Lys Gly Trp  Thr Ala Ala Glu Ile  Ala Glu Lys
    2645                 2650                 2655

Thr Ala  Gly Arg Asn Ile Phe  Val Leu Thr Ile Phe  Glu Gly Leu
    2660                 2665                 2670

Glu Met  Leu Gly Leu Asp Ala  Asp Ser Lys Trp Arg  Asn Leu Ser
    2675                 2680                 2685

Ser Asn  Tyr Leu Ile Asp Ala  Val Lys Lys Ile Ile  Glu Lys Met
    2690                 2695                 2700

Thr Lys  Thr Ala Thr Ser Phe  Thr Tyr Ser Phe Leu  Lys Ser Leu
    2705                 2710                 2715

Leu Pro  Ala Pro Phe Ser Cys  Thr Lys Ser Glu Arg  Asp Pro Arg
    2720                 2725                 2730

Ile Gly  Trp Pro Gln Lys Asp  Tyr Asp Tyr Leu Glu  Val Arg Cys
    2735                 2740                 2745

Ala Cys  Gly Tyr Asn Arg Arg  Ala Ile Lys Arg Asp  Ser Gly Pro
    2750                 2755                 2760

Val Leu  Trp Glu Thr Leu Glu  Glu Thr Gly Pro Glu  Tyr Cys His
    2765                 2770                 2775

Asn Arg  Gly Glu Arg Gly Leu  Ser Asn Val Lys Thr  Thr Arg Cys
    2780                 2785                 2790

Phe Val  Gln Gly Glu Glu Ile  Pro Pro Ile Ala Leu  Arg Lys Gly
    2795                 2800                 2805

Val Gly  Glu Met Leu Val Lys  Gly Val Ser Phe Arg  Ile Asp Phe
    2810                 2815                 2820

Asp Lys  Asp Lys Ile Leu Ser  Thr Asp Lys Trp Lys  Val Pro His
    2825                 2830                 2835

Arg Ala  Val Thr Ser Ile Phe  Glu Asp Trp Gln Gly  Ile Gly Tyr
    2840                 2845                 2850

Arg Glu  Ala Tyr Leu Gly Thr  Lys Pro Asp Tyr Gly  Gly Leu Val
    2855                 2860                 2865

Pro Arg  Ser Cys Val Thr Val  Thr Lys Gln Gly Leu  Thr Phe Leu
    2870                 2875                 2880

Lys Thr  Ala Arg Gly Met Ala  Phe Thr Thr Asp Leu  Thr Ile Gln
    2885                 2890                 2895

Asn Ile  Lys Met Leu Ile Ala  Thr Cys Phe Lys Asn  Lys Val Lys
    2900                 2905                 2910

Glu Gly  Glu Ile Pro Ala Thr  Ile Glu Gly Glu Thr  Trp Ile Asn
    2915                 2920                 2925

Ile Pro  Leu Val Asn Glu Asp  Thr Gly Thr Ile Lys  Pro Ser Phe
    2930                 2935                 2940

Gly Glu  Arg Val Ile Pro Glu  Pro Tyr Glu Glu Asp  Pro Leu Glu
    2945                 2950                 2955

Gly Pro  Ser Val Ile Val Glu  Thr Gly Gly Ile Ala  Ile Asn Gln
```

-continued

```
    2960                2965                2970

Ile Gly  Val Asn Pro Gln Ser  Ser Thr Cys Gly Thr  Val Phe Thr
    2975                2980                2985

Ala Val  Lys Asp Leu Cys Gln  Thr Val Ser Asn Lys  Ala Lys Asn
    2990                2995                3000

Ile Lys  Ile Gly Phe Ser Glu  Gly Gln Tyr Pro Gly  Pro Gly Val
    3005                3010                3015

Ala Lys  Lys Thr Leu Asn Gln  Leu Ile Gln Asp Glu  Asp Pro Lys
    3020                3025                3030

Pro Phe  Ile Phe Val Cys Gly  Ser Asp Lys Ser Met  Ser Asn Arg
    3035                3040                3045

Ala Lys  Thr Ala Arg Asn Ile  Lys Arg Ile Thr Thr  Thr Thr Pro
    3050                3055                3060

Glu Lys  Phe Arg Asp Leu Ala  Lys Asn Lys Lys Leu  Ile Ile Val
    3065                3070                3075

Leu Leu  Gly Asp Arg Tyr His  Glu Asp Ile Glu Lys  Tyr Ala Asp
    3080                3085                3090

Phe Lys  Gly Thr Phe Leu Thr  Arg Gln Thr Leu Glu  Ala Leu Ala
    3095                3100                3105

Ser Ala  Lys Ala Val Glu Lys  Asp Met Thr Lys Lys  Glu Ala Ala
    3110                3115                3120

Arg Val  Leu Ala Met Glu Glu  Lys Asp Glu Leu Glu  Leu Pro Gly
    3125                3130                3135

Trp Leu  His Thr Asp Ala Pro  Lys Phe Leu Asp Ile  Thr Lys Asp
    3140                3145                3150

Asn Ile  Thr His His Leu Ile  Gly Asp Met Gln Ser  Leu Arg Glu
    3155                3160                3165

Arg Ala  Gly Glu Ile Gly Ala  Lys Ala Thr Thr Gln  Ile Thr Lys
    3170                3175                3180

Lys Gly  Ser Val Tyr Thr Ile  Asn Leu Ser Thr Trp  Trp Glu Ser
    3185                3190                3195

Glu Arg  Leu Ala Ser Leu Glu  Pro Leu Phe Arg Glu  Leu Leu Ser
    3200                3205                3210

Lys Cys  Arg Pro Val Asp Arg  Glu Thr Tyr Lys Asn  Cys His Phe
    3215                3220                3225

Ala Thr  Ala Ala Gln Leu Ala  Gly Gly Asn Trp Val  Pro Val Ala
    3230                3235                3240

Pro Val  Val His Leu Gly Glu  Ile Pro Val Lys Lys  Lys Lys Thr
    3245                3250                3255

Leu Pro  Tyr Glu Ala Tyr Lys  Leu Leu Lys Glu Met  Val Asp Ser
    3260                3265                3270

Glu Lys  Glu Phe His Lys Pro  Val Ser Arg Glu Lys  His Gln Trp
    3275                3280                3285

Ile Leu  Asn Lys Val Lys Thr  Gly Gly Asp Leu Gly  Leu Lys Asn
    3290                3295                3300

Leu Val  Cys Pro Gly Arg Val  Gly Glu Pro Ile Leu  Arg Glu Lys
    3305                3310                3315

Lys Lys  Phe Asn Ile Tyr Asn  Lys Arg Ile Thr Ser  Thr Met Leu
    3320                3325                3330

Ser Val  Gly Ile Arg Pro Glu  Lys Leu Pro Val Val  Arg Ala Gln
    3335                3340                3345

Thr Ser  Thr Lys Glu Phe His  Glu Ala Ile Arg Asp  Lys Ile Asp
    3350                3355                3360
```

-continued

Lys Lys Ala Asn Thr Gln Thr Pro Gly Leu His Lys Glu Leu Leu
3365 3370 3375

Glu Ile Phe Asn Ser Ile Cys Ala Ile Pro Glu Leu Arg Asn Thr
3380 3385 3390

Tyr Lys Glu Val Asp Trp Asp Val Leu Thr Ser Gly Ile Asn Arg
3395 3400 3405

Lys Gly Ala Ala Gly Tyr Phe Glu Lys Met Asn Ile Gly Glu Ile
3410 3415 3420

Ile Asp Ser Asp Lys Lys Ser Val Glu Gln Leu Ile Lys Arg Met
3425 3430 3435

Lys Ser Gly Leu Glu Phe Asn Tyr Tyr Glu Thr Ala Ile Pro Lys
3440 3445 3450

Asn Glu Lys Arg Ala Val Val Asp Asp Trp Met Glu Gly Asp Tyr
3455 3460 3465

Val Glu Glu Lys Arg Pro Arg Val Ile Gln Tyr Pro Glu Ala Lys
3470 3475 3480

Met Arg Leu Ala Ile Thr Lys Val Met Tyr Asn Trp Val Lys Gln
3485 3490 3495

Lys Pro Ile Val Ile Pro Gly Tyr Glu Gly Lys Thr Pro Leu Phe
3500 3505 3510

His Val Phe Asp Lys Val His Lys Glu Trp Lys Asn Phe Asn Ser
3515 3520 3525

Pro Val Ala Val Ser Phe Asp Thr Lys Ala Trp Asp Thr Gln Val
3530 3535 3540

Thr Pro Lys Asp Leu Leu Leu Ile Ser Glu Ile Gln Lys Tyr Tyr
3545 3550 3555

Tyr Lys Lys Glu Tyr His Arg Phe Ile Asp Asn Leu Thr Glu Lys
3560 3565 3570

Met Val Glu Val Pro Val Val Cys Glu Asp Gly Asn Val Tyr Ile
3575 3580 3585

Arg Glu Gly Gln Arg Gly Ser Gly Gln Pro Asp Thr Ser Ala Gly
3590 3595 3600

Asn Ser Met Leu Asn Val Leu Thr Met Ile Tyr Ala Phe Cys Lys
3605 3610 3615

Ala Asn Ser Ile Pro Tyr Ser Ala Phe His Arg Val Ala Lys Ile
3620 3625 3630

His Val Cys Gly Asp Asp Gly Phe Leu Ile Thr Glu Lys Ser Phe
3635 3640 3645

Gly Glu Ala Phe Ala Ile Lys Gly Pro Gln Ile Leu Met Glu Ala
3650 3655 3660

Gly Lys Pro Gln Lys Leu Ile Gly Glu Phe Gly Leu Lys Leu Ala
3665 3670 3675

Tyr Lys Phe Asp Asp Ile Glu Phe Cys Ser His Thr Pro Ile Lys
3680 3685 3690

Val Arg Trp Ala Asp Asn Asn Thr Ser Tyr Met Pro Gly Arg Asp
3695 3700 3705

Thr Ala Thr Ile Leu Ala Lys Met Ala Thr Arg Leu Asp Ser Ser
3710 3715 3720

Gly Glu Arg Gly Thr Glu Gly Tyr Glu Leu Ala Val Ala Phe Ser
3725 3730 3735

Phe Leu Leu Met Tyr Ser Trp Asn Pro Leu Val Arg Arg Ile Cys
3740 3745 3750

Leu Leu Val Met Ser Thr Ile Asp Thr Lys Glu Ala Ser Gln Asn
3755 3760 3765

```
Asn Thr  Ile Tyr Thr Phe Arg  Gly Asp Pro Ile Gly  Ala Tyr Thr
    3770                 3775                 3780

Glu Val  Ile Gly Tyr Arg Leu  Asp Gln Leu Lys Gln  Thr Glu Phe
    3785                 3790                 3795

Ser Lys  Leu Ala Gln Leu Asn  Leu Ser Met Ala Ile  Leu Gln Ile
    3800                 3805                 3810

Tyr Asn  Lys Asn Thr Thr Lys  Arg Leu Ile Glu Asp  Cys Val Lys
    3815                 3820                 3825

Leu Gly  Asn Gln Asn Lys Gln  Ile Leu Val Asn Ala  Asp Arg Leu
    3830                 3835                 3840

Ile Ser  Lys Lys Thr Gly Tyr  Thr Tyr Glu Pro Thr  Ala Gly His
    3845                 3850                 3855

Thr Lys  Ile Gly Lys His Tyr  Glu Glu Ile Asn Leu  Leu Lys Asp
    3860                 3865                 3870

Thr Pro  Gln Lys Thr Val Tyr  Gln Gly Thr Glu Arg  Tyr
    3875                 3880                 3885
```

<210> SEQ ID NO 3
<211> LENGTH: 418
<212> TYPE: DNA
<213> ORGANISM: PMC Virus

<400> SEQUENCE: 3

```
gtataacgac agtagttcaa gtgtcgttat gcatcattgg ccataacaaa ttatctaatt     60
tggaataggg acctgcgacc tgtacgaagg ccgagcgtcg gtagccattc cgactagtag    120
gactagtaca aataggtcaa ctggttgagc aggtgagtgt gctgcagcgg ctaagcggtg    180
agtacaccgt attcgtcaac aggtgctact ggaaaggatc acccactagc gatgcctgtg    240
tggacgagga catgtccaag ccaatgttat cagtagcggg ggtcgttact gagaaagctg    300
cccagaatgg gtagttgcac atacagtctg ataggatgcc ggcggatgcc ctgtattttg    360
accagtataa atattatccg ttgtaaagca tatgaatact tttactttta atacatat      418
```

<210> SEQ ID NO 4
<211> LENGTH: 504
<212> TYPE: DNA
<213> ORGANISM: PMC Virus

<400> SEQUENCE: 4

```
ggagggagtg aggaaggaaa catgttcttt agaactgcac ccacgccgcc accagggtgc     60
caagaaccgg tttacacaag cacaatgaga ccaatttttg gcgaacccca tccacctcta    120
cacaaacaca gcacgttaaa attgccacat tggaggggga tcaaaacaat tagagttaag    180
aagagagaat tgccaaagaa gggcgattgt agcaactcaa caacagctcc cacttcgggg    240
gtgtacgttg aattaggggc tgtgttctat aaagattaca cgggcacggt ataccatcgt    300
gtaccgctag aactttgtac aaaccaagag aggtgcgagg gatccaagtg tgtagggaga    360
atgacagggt ctgatggcag gttgtacaac gttttagtat gtccggacga ttgtatcctc    420
tttgagagac actgtagagg tcaaacagtc gtcctgaaat ggatttccaa ccccttgaca    480
tcaccacttt gggtccagag ttgt                                           504
```

<210> SEQ ID NO 5
<211> LENGTH: 297
<212> TYPE: DNA
<213> ORGANISM: PMC Virus

<400> SEQUENCE: 5

-continued

```
tctgacgaca aaggagcaaa acccaaggtg aaaccaaaag acgacaggat gaagcaagga     60
aaaatagtga caaagcctaa agagactgaa gcagatcaaa aaactagacc accagatgcc    120
acgatagtgg ttgacgggca gaagtatcag gtgaggaaga aggggaaagc gaaacccaag    180
actcaagacg gcttatacca caacaagaac aaaccagaag cgtccaggaa gaagcttgag    240
aaggccttgc tagcatgggc aatattagcc tgcctattgg tggtaccggt agggtcc       297
```

<210> SEQ ID NO 6
<211> LENGTH: 666
<212> TYPE: DNA
<213> ORGANISM: PMC Virus

<400> SEQUENCE: 6

```
accaacgtga cacaatggaa cttatgggac aataaaagta ctacagacat acatagcgtc     60
atgttttcta gagggattaa aaggagtctg catggaattt ggcccacaca aatctgcaaa    120
gggatcccta cacatctagc agcagactat gaactgaaaa ggattcacgg gatggtggat    180
gcaagcccca tgaccaactt cacatgttgt aggctacaga gacatgagtg gaacaagcat    240
gggtggtgca actggtacaa tatagagccg tggatcaatc tcatgaataa tacccaagga    300
ctattaaaca ctggagacaa tttcactgag tgcgcagtca catgcaggta tgatgcagac    360
ttaggggtga atatagtgac tcaagccagg actactccaa ctatcctgac tggctgtaag    420
aaagggcaca acttctcttt ctcaggggag gtcagggcct caccctgcaa ctttgagtta    480
actgctgaag acttgctcag gatcatggat cacaccaact gcgagggatt tacctacttc    540
ggggaaggaa tcgttgacgg ttacaccgag gtagtagaga aggccaggtc aagtggtttc    600
agggctctca catggttgtc gagtaagatt gaaaacacca agaaaaaaat attcggagct    660
gaagcc                                                               666
```

<210> SEQ ID NO 7
<211> LENGTH: 588
<212> TYPE: DNA
<213> ORGANISM: PMC Virus

<400> SEQUENCE: 7

```
agtccttact gcccagtggc taagagggtc ttcaacatta tttataccaa caattgcacc     60
ccgcttggac tgccagataa gtcaaaaatt ataggaccag gaacctttga catcagtggc    120
agggatgaat tcatatttcc aaaactcccc taccacgtag atgacttcat tctactgagc    180
ttaattgcaa tgtctgattt tgctccagag acatcaagta taatctacct ggctttgcac    240
tacctaatgc caagtaatga caacagggac ttcgtgatgg acctggaccc aaataaacta    300
aaccttactg caactaaatc cgtggcaagt gtggtcccta catcggtgaa tgtgttaggt    360
gaatgggtgt gcgtcaaacc aagttggtgg ccttattccg ccgaaatcac taatctgata    420
ggaggtgtca tcaccgtggc agacttagtt atcaagacca ttgaagaatt gctaaatttg    480
tggaccgaag caacagctgt ggcatttctg gctgctctaa taaaaatttt tagaggccag    540
ccgatccaag cggtagcatg gttaatcatc atagggggag cacaagcc                 588
```

<210> SEQ ID NO 8
<211> LENGTH: 1131
<212> TYPE: DNA
<213> ORGANISM: PMC Virus

<400> SEQUENCE: 8

```
caaacctgca accctgaatt catgtacgca ttagcgaaaa ataccagcat aggttcatta     60
```

```
ggaccagaat cactgacgac aaggtggtac caactaacca gcggtttcaa actcactgac    120

agcacgattg aagtcacctg tgtgggtgct aacatgagga ttcatgtagt gtgcccactt    180

gtaagtgaca gatatttggc cataaaccac cctagagcac tgccaacaac ggcgtggttc    240

aggaaaatac acactcagca tgaggtacca agagaaagaa tcatgagtga gtcaaaaagg    300

aggtacactt gtccttgtgg ttctaaacca gtggtgaggt caacaacaca attcaaccca    360

atatctatat ctaccccaag ctttgaactt gaatgcccta ggggttggac tggggctgta    420

gagtgtacac tagtctcccc atcaactctg acaacagaga ctatattcac atacaggaag    480

cccaaaccat tcggacttga aaactggtgc aagtatacag tggtggagaa agggatcctg    540

tattcttgta aatttggggg caattcaaca tgcatcaaag ggcttatagt taaagggcaa    600

cgggaagaca aagtaaggta ctgtgaatgg tgtggttata agttcagttc accaaatgga    660

ctgcctcagt atccactggg attgtgtgag aaagaacaat cagaaggact cagggattat    720

ggtgacttcc catgctgcaa caacggcact tgtattgaca aagaaggtag tgtgcaatgc    780

tacatagggg ataagaaagt taccgtgaag ctgtataatg cctcactatt ggcccccatg    840

ccctgcaaac ccatagtgta taactcccag gggcccccag cgcctaagac ctgcacttat    900

aggtgggcct caacattaga aaataaatat tatgaaccca gggacagcta ctaccagcaa    960

tacattataa agtcagggta tcaatattgg tttgatctca cagcaaagga tcatgtggca   1020

gactggatca caaaatactt tccaataata atagtggcct tgttaggggg cagaggcacc   1080

ttgtgggtgt tgatagctta tgagttgcta actcagtatg aggtagtagg a            1131
```

```
<210> SEQ ID NO 9
<211> LENGTH: 216
<212> TYPE: DNA
<213> ORGANISM: PMC Virus

<400> SEQUENCE: 9

gacgagaaca tagtggctca agctgaagcc ctggtaatcg gaaacatctt gatgagttta     60

gacttagaga taattagctg cttccttctg ttgttgatcg tggtgaaaaa acaagctgtc    120

aggagaacgt tggctttact gtttcattgg ataactatga acccattcca gtcagtaatg    180

atcacagtgg tctacttcgt cggtttggtg agggcc                               216
```

```
<210> SEQ ID NO 10
<211> LENGTH: 1404
<212> TYPE: DNA
<213> ORGANISM: PMC Virus

<400> SEQUENCE: 10

gaagagggaa ctaaagaggg tagtacaagc gggccaccaa tccatgtagt tgcaatactg     60

ttattcctct tgtaccacac agtgaagtat aaggacttta acatagcaat gatcttactt    120

ataacattgt ccctgaaaag ctcatcctac atacatacca gcttgtatga aattccattg    180

cttgtggctg taataagtct cacatgctcc atatacattt ttgacttgca ggtaaagagc    240

aagctagtgg ccccaactat aggtataatt ggagttaccc tagcaatgag agttttgtgg    300

ctggtaaggc aaatgactat accaaccccc tctgtgtcca ttagtctgat agatccaaag    360

atggtcataa tactctactt gatatcccta actattacag tcaatcacaa cctagaccta    420

gcaagttatt gcttgaaact gggacctttt atcctatcat tcctaacaat gtgggtggat    480

gttgtcatcc tcctgctcat gctgccttgg tacgaactag taaaagtcta ctacctaaaa    540

aagaagaaag aggatgtgga aacatggttc caaaattcag gaatatccac ccaagaaact    600
```

-continued

```
tccccatacg gatttgattt ttctagcccc ggggagggag tgcacacact accaatgcaa    660

aataaaacca aattttgtag gactgcttac atgactgtac taagggcttt ggtgataaca    720

gccatcagca gtgtctggaa accaataatt ttagcagaac tcctaataga ggcagtgtat    780

tggacacaca ttaaaatagc caaagaattg gcggggtcaa gcaggttcgt tgctaggttc    840

attgcatcta ttatagagtt gaattgggcc atggacgaaa aagaagcatc tcggtacaaa    900

agattttacc tattatcatc caaaataaca gatctaatgg ttaagcacaa aatccaaaat    960

gagacagtaa aatcctggtt tgaagaaact gaaatatttg gaatacaaaa agtggcaatg   1020

gtgataaggg ctcattctct gagtttggag ccaaatgcca tcctttgctc cgtttgtgaa   1080

gaaaaacaaa atcaaaaagc caaaaggccc tgccctaagt gtggtagtag aggcactcaa   1140

ataaagtgtg ggctgacact ggccgagttt gaggaagaac attacaaaaa aatatacatc   1200

ctcgaaggcc aagatgaaac tcccatgagg aaagaagaaa gacagcaagt aacttatgtc   1260

tctaggggtg ctctgttcct taggaatctt cctatcttag cttcaaaaaa caaataccta   1320

cttgtaggca atctgggtat ggaattgcaa gatttggaaa gtatgggatg gatcattcga   1380

gggccagccg tctgcaagaa gata                                          1404
```

<210> SEQ ID NO 11
<211> LENGTH: 2028
<212> TYPE: DNA
<213> ORGANISM: PMC virus

<400> SEQUENCE: 11

```
atacaccatg agaaatgcag gccttcaata ccagacaaac tcatggcatt cttcgggatt     60

atgcctaggg gagttacacc aagagcccct acacggttcc ctgtgtcctt gctgaagata    120

agacggggtt ttgagaccgg ctgggcctac acacaccctg gaggggtaag tagtgtgatg    180

catgtcaccg ctgggtcgga tatatatgtc aatgactcaa tagggaggac aaaaatccag    240

tgccaagaca aaaacactac aacagatgag tgtgaatatg gtgtgaaaac agactcaggg    300

tgctctgatg gagctcggtg ctatgtcatc aaccctgaag caaccaacat agcagggacc    360

aagggggcca tggtacacct gaggaaagct ggaggagagt tcaactgcgt gactgcccag    420

ggtacccccg ccttctataa tctaaagaac ttaaaaggat ggtcaggcct gcctatcttt    480

gaagctgcca caggaagagt ggtaggaagg gtaaaagcag gaaaaaacac tgacaatgct    540

ccaacaacca ttatgtcagg gacgcaagtg gcaaaaccat cagagtgtga cctagaatca    600

gtggtgagga aactagagac aatgaacaga ggggaattca aacaagtgac tctggctaca    660

ggcgcaggaa agacaaccat gctaccaaag ctgttaatag aatccatagg caggcataag    720

agagtgttag tactgatccc gttgagagct gcagcggagg gggtgtacca gtacatgaga    780

accaaacacc caagcatatc tttcaacttg aggataggg atctgaaaga aggtgacatg    840

gcaactggga tcacctatgc ctcttatggg tacttctgcc aaatggacat gcctagactg    900

gagaatgcaa tgaaggaata ccactatatt ttcttggatg aatatcactg tgccacacca    960

gaacagttgg cagtgatgtc aaaaatacat aggttcggtg aatcagttag ggtaatagcc   1020

atgaccgcca cgccatccgg gactgtgagc acaacagggc agaaattcac aattgaggag   1080

gtggtagtac ctgaagtgat gaagggggag gaccttgctg atgattacat cgaaatagca   1140

gggttgaagg tgccaaagaa agagttagag ggtaacgtac tgacttttgt gcctacaagg   1200

aagatggcat cggaaacagc aaaaaaatta accacacagg gatacaatgc tggatactac   1260

ttcagtggag aagatccatc atccctgcgg acaactactt ctaagtcacc atatatagta   1320
```

```
gttgcaacca atgccattga atccggggta accttaccgg accttgatac agtaatagat   1380

acaggcatga agtgtgaaaa gagactaaga atcgaaaaca aagctcccta catcgtaaca   1440

ggactgaaaa gaatggctat aacaacgggg gagcaagctc aaagaaaagg tagggtaggc   1500

agggttaaac ctgggaggta cttgagagga cctgaaaaca ctgcaggtga aaaggactat   1560

cactatgacc ttttacaggc acagaggtac ggcatccaag actcaataaa catcaccaag   1620

tctttcaggg agatgaacta tgattgggca ttatatgagg aagacccgtt aaagattgcc   1680

caattagagt tgctaaacac actcctgatc tcaagggatc tgccagtagt aacaaaaaat   1740

ctgatggccc gcacaacaca tcccgaacct atacaattgg cttacaatag tttagaaacc   1800

cctgtaccgg tggcattccc aaaagtgaaa aatggagaag tcactgacgc acatgaaact   1860

tacgagttga tgacctgtag gaagcttgag aaagaccccc ctatatacct gtatgcaaca   1920

gaagaagaag atctcgtagt ggacatactg ggattgaaat ggccagacgc cacagagagg   1980

gctgtcttgg aagtgcaaga cgccctgggc cagatcacag gtttatct               2028
```

<210> SEQ ID NO 12
<211> LENGTH: 189
<212> TYPE: DNA
<213> ORGANISM: PMC Virus

<400> SEQUENCE: 12

```
gcaggggaga cagctttact catagcccta ttagggtggg tgggctacga agccttggtg     60

aagaggcacg tgcctatggt gacagacata tacaccctag aagatgaaaa attggaagac    120

actacacacc tacaatttgc cccagatgat ctgaacaatt cagataccat tgagctccaa    180

gacttatcg                                                            189
```

<210> SEQ ID NO 13
<211> LENGTH: 1041
<212> TYPE: DNA
<213> ORGANISM: PMC Virus

<400> SEQUENCE: 13

```
aatcaccaaa tccaacaaat tctagaaggt gggaaggaat atgtcggcca agcctaccaa     60

ttcctcaggt tgcaagctga gagggctgcc aactcagaca aaggcaagaa agcaatggca    120

gcggccccat tactagccca caagttcctg gaatacttgc aagagcatgc aggtgacata    180

aagaagtatg gtctatgggg ggtccacaca gcattgtata acagcataaa agaaagactg    240

ggtcacgaaa ctgcattcgc atctctggtt ataaaatgga ttgccttttc ctcagatgga    300

gtcccgggga tgattaagca agcagcagta gacttggtgg tatactatat aatcaacagg    360

cctgagtatc aaggggataa ggagacacag aatgcaggta gacaatttgt tggctccctt    420

tttgtttcat gtctagcaga gtacacattc aaaaacttca ataaatcagc attagaagga    480

ttgatcgagc ctgccttaag ctatctaccc tacgcttcaa gcgcactaaa gttattccta    540

ccgactagac ttgaaagtgt agtgatactg tccactacta tatacagaac atacttatca    600

atcaggaaag gatctagtca gggtttagcc gggctggcag ttagctcagc gatggagatc    660

atgaaccaga acccaatcag cgtggctatt gcactggcac taggagtcgg agcaatagcg    720

gcacataatg ccattgagag cagtgaggca aaaaggactc tcctgatgaa ggtctttgtt    780

aagaactttt tggaccaagc agccactgat gagcttgtga aagagaaccc tgagaagatc    840

ataatggcag tgtttgaggg cattcaaaca gctggaaatc cattgagact tgtataccat    900

ctatatgcaa tgttctacaa agggtggact gccgcggaaa tagctgaaaa aaccgctggt    960
```

aggaacattt ttgtgttaac aatatttgaa ggattggaaa tgttaggcct ggatgccgac 1020
tcaaaatgga gaaatctgag c 1041

<210> SEQ ID NO 14
<211> LENGTH: 1515
<212> TYPE: DNA
<213> ORGANISM: PMC Virus

<400> SEQUENCE: 14
tctaattatc ttattgatgc agtgaagaaa atcattgaaa aaatgactaa aacagcaaca 60
agcttcacct acagcttttt gaaatctttg cttcctgccc ccttctcgtg tactaaatca 120
gaaagagatc caagaatagg gtggccccaa aaagactacg actacctcga ggtccgatgc 180
gcttgtgggt ataacaggag agctataaaa agagactcag gacctgtgtt atgggagacc 240
ttagaggaga cgggtccaga gtactgccac aacagaggtg aaagggggct cagcaatgtg 300
aagactacta gatgctttgt ccaaggagag gaaatccctc caattgcact gaggaaagga 360
gtaggtgaga tgttggtcaa gggtgtttca ttcagaatag attttgataa agacaagata 420
ctttcaacag acaagtggaa ggtaccacat agggcagtta catcaatctt tgaggattgg 480
cagggtattg gttacagaga ggcttaccta gggaccaaac cagactatgg gggtctggtg 540
cccagatctt gtgtaactgt aacaaaacaa gggttaacat tcttgaaaac tgccagaggc 600
atggctttca cgactgacct gaccatccag aacatcaaaa tgctgatagc tacatgcttc 660
aagaacaagg tgaaggaagg ggagatacca gctacgattg aaggggaaac atggatcaac 720
ataccactag tgaatgagga caccgggacc attaaaccaa gcttcgggga aagagtgatt 780
cccgaaccat atgaggagga cccacttgaa ggcccaagtg taatcgttga aacaggaggc 840
atagccatca accaaatagg ggtcaatcca caatccagta catgtggaac agtttttaca 900
gcagtgaagg atctgtgcca aacagttagt aataaagcca agaatatcaa aattgggttt 960
tcggaaggcc aatacccagg tccaggggtt gcaaagaaga cactgaacca gctcatacaa 1020
gatgaagacc caaaaccatt catatttgtt tgtggctctg acaagtcaat gtctaatcgg 1080
gcaaaaactg cgaggaacat caagagaatc accaccacaa cacctgagaa attcagagac 1140
ttggcaaaaa acaagaaatt gataattgtg ctgttaggtg atagatacca tgaagatata 1200
gaaaagtatg cagacttcaa gggcaccttc ttgaccagac aaaccttgga agcactagca 1260
agtgccaaag ctgtagagaa ggacatgacc aagaaagaag cagcaagagt attggcaatg 1320
gaagaaaagg atgaactaga actcccaggg tggctgcata cagatgcacc caaattccta 1380
gacattacta aggacaacat cacacatcac ctaatagggg acatgcagag tctgagagaa 1440
agagcagggg agataggagc aaaggccacc actcaaatca ctaagaaagg gagtgtatac 1500
acaatcaatc tgagt 1515

<210> SEQ ID NO 15
<211> LENGTH: 2080
<212> TYPE: DNA
<213> ORGANISM: PMC Virus

<400> SEQUENCE: 15
acgtggtggg agtcagagag gttggcatct ttggaacctt tgttccggga actactatct 60
aaatgcaggc cagtggacag ggagacatat aagaattgtc attttgcaac agcagcccaa 120
cttgccggag gaaactgggt accggtagca ccagttgtac atcttgggga aattccggta 180
aagaagaaaa agactctccc ctacgaggca tacaagctcc taaaagagat ggttgactcg 240

```
gagaaggaat tccataaacc agtgagcagg gaaaaacacc aatggatact gaacaaagtg    300

aaaactggtg gtgacctcgg cttaaaaaat ctagtatgtc caggtagggt tggagaacca    360

atcctaagag agaagaagaa attcaacatt tacaacaaga ggattaccag tactatgtta    420

tcagtaggga taaggccaga aaaattgcca gtggtaagag cccagaccag taccaaagaa    480

tttcatgaag caataaggga caaaatagac aaaaaagcaa acacacagac cccaggccta    540

cacaaagaat tgttggagat attcaactca atatgtgcca tccccgaact tagaaatacc    600

tacaaagagg ttgattggga cgttctaacc tcaggcataa ataggaaagg tgcagccggg    660

tacttcgaaa aaatgaacat aggggagatc atagatagtg acaaaaaatc agtggaacaa    720

ctcataaaga gaatgaaatc agggctagaa ttcaactact atgagactgc aataccaaaa    780

aatgagaaga gggcagtggt agatgattgg atggaaggtg actatgtaga agaaaaaaga    840

ccaagagtca tacagtatcc tgaggcaaag atgagattag ctataaccaa agtaatgtat    900

aactgggtca agcagaagcc tatagtaatc cctggatacg aaggtaagac tcctttgttt    960

catgttttcg acaaggtcca caaagaatgg aaaaatttca acagtccagt tgcagtcagt   1020

tttgacacta aagcctggga cacacaagta acacccaaag accttctcct catatcagaa   1080

atccaaaagt attattacaa gaaagaatac catagattca tagataattt gaccgagaaa   1140

atggtggagg taccagtggt ttgtgaagac ggaaacgtct acataagaga aggtcagagg   1200

ggaagtggtc aaccagacac tagcgcaggt aatagtatgt tgaatgtact gactatgata   1260

tatgccttct gcaaagctaa ctccatccct tactcagcct tccacagggt agcaaagata   1320

catgtgtgtg gagatgatgg tttcttgata actgagaaaa gttttggtga ggcctttgcg   1380

atcaaggggc ctcaaatttt gatggaagca ggaaaaccac aaaaacttat aggtgaattt   1440

ggactgaaat tggcatataa atttgatgac attgaatttt gctcgcatac accaataaag   1500

gtcaggtggg ctgacaacaa cacatcatac atgcccggaa gagacacagc taccattcta   1560

gctaaaatgg caacccgcct tgactctagt ggggagaggg ggaccgaggg atacgagctg   1620

gccgtggcct tcagtttctt actaatgtat tcttggaacc ccctggtaag aagaatatgc   1680

ctgcttgtca tgtctacaat tgacacaaaa gaagctagcc aaaataacac tatatataca   1740

tttagggggg atcccatagg tgcctacaca gaggtaattg ggtataggct ggaccaacta   1800

aaacagacag agttctctaa attggctcag ctgaatttgt caatggcaat acttcaaata   1860

tacaataaaa acacaaccaa gagactcatc gaagattgtg tgaaacttgg caaccaaaat   1920

aagcaaatat tggtgaatgc agaccgtttg atcagcaaga aaacgggcta cacatatgag   1980

ccaacagctg gccacactaa gataggcaag cactatgaag aaatcaacct gctgaaagat   2040

acaccacaaa aaactgtcta ccaaggaact gaaaggtata                          2080
```

<210> SEQ ID NO 16
<211> LENGTH: 167
<212> TYPE: PRT
<213> ORGANISM: PMC Virus

<400> SEQUENCE: 16

```
Gly Gly Ser Glu Glu Gly Asn Met Phe Phe Arg Thr Ala Pro Thr Pro
1               5                   10                  15

Pro Pro Gly Cys Gln Glu Pro Val Tyr Thr Ser Thr Met Arg Pro Ile
            20                  25                  30

Phe Gly Glu Pro His Pro Pro Leu His Lys His Ser Thr Leu Lys Leu
        35                  40                  45
```

```
Pro His Trp Arg Gly Ile Lys Thr Ile Arg Val Lys Lys Arg Glu Leu
    50                  55                  60

Pro Lys Lys Gly Asp Cys Ser Asn Ser Thr Thr Ala Pro Thr Ser Gly
65                  70                  75                  80

Val Tyr Val Glu Leu Gly Ala Val Phe Tyr Lys Asp Tyr Thr Gly Thr
                85                  90                  95

Val Tyr His Arg Val Pro Leu Glu Leu Cys Thr Asn Gln Glu Arg Cys
            100                 105                 110

Glu Gly Ser Lys Cys Val Gly Arg Met Thr Gly Ser Asp Gly Arg Leu
        115                 120                 125

Tyr Asn Val Leu Val Cys Pro Asp Asp Cys Ile Leu Phe Glu Arg His
    130                 135                 140

Cys Arg Gly Gln Thr Val Val Leu Lys Trp Ile Ser Asn Pro Leu Thr
145                 150                 155                 160

Ser Pro Leu Trp Val Gln Ser
                165


<210> SEQ ID NO 17
<211> LENGTH: 99
<212> TYPE: PRT
<213> ORGANISM: PMC Virus

<400> SEQUENCE: 17

Ser Asp Asp Lys Gly Ala Lys Pro Lys Val Lys Pro Lys Asp Asp Arg
1               5                   10                  15

Met Lys Gln Gly Lys Ile Val Thr Lys Pro Lys Glu Thr Glu Ala Asp
            20                  25                  30

Gln Lys Thr Arg Pro Pro Asp Ala Thr Ile Val Val Asp Gly Gln Lys
        35                  40                  45

Tyr Gln Val Arg Lys Lys Gly Lys Ala Lys Pro Lys Thr Gln Asp Gly
    50                  55                  60

Leu Tyr His Asn Lys Asn Lys Pro Glu Ala Ser Arg Lys Lys Leu Glu
65                  70                  75                  80

Lys Ala Leu Leu Ala Trp Ala Ile Leu Ala Cys Leu Leu Val Val Pro
                85                  90                  95

Val Gly Ser


<210> SEQ ID NO 18
<211> LENGTH: 222
<212> TYPE: PRT
<213> ORGANISM: PMC Virus

<400> SEQUENCE: 18

Thr Asn Val Thr Gln Trp Asn Leu Trp Asp Asn Lys Ser Thr Thr Asp
1               5                   10                  15

Ile His Ser Val Met Phe Ser Arg Gly Ile Lys Arg Ser Leu His Gly
            20                  25                  30

Ile Trp Pro Thr Gln Ile Cys Lys Gly Ile Pro Thr His Leu Ala Ala
        35                  40                  45

Asp Tyr Glu Leu Lys Arg Ile His Gly Met Val Asp Ala Ser Pro Met
    50                  55                  60

Thr Asn Phe Thr Cys Cys Arg Leu Gln Arg His Glu Trp Asn Lys His
65                  70                  75                  80

Gly Trp Cys Asn Trp Tyr Asn Ile Glu Pro Trp Ile Asn Leu Met Asn
                85                  90                  95

Asn Thr Gln Gly Leu Leu Asn Thr Gly Asp Asn Phe Thr Glu Cys Ala
            100                 105                 110
```

```
Val Thr Cys Arg Tyr Asp Ala Asp Leu Gly Val Asn Ile Val Thr Gln
        115                 120                 125

Ala Arg Thr Thr Pro Thr Ile Leu Thr Gly Cys Lys Lys Gly His Asn
    130                 135                 140

Phe Ser Phe Ser Gly Glu Val Arg Ala Ser Pro Cys Asn Phe Glu Leu
145                 150                 155                 160

Thr Ala Glu Asp Leu Leu Arg Ile Met Asp His Thr Asn Cys Glu Gly
                165                 170                 175

Phe Thr Tyr Phe Gly Glu Gly Ile Val Asp Gly Tyr Thr Glu Val Val
            180                 185                 190

Glu Lys Ala Arg Ser Ser Gly Phe Arg Ala Leu Thr Trp Leu Ser Ser
        195                 200                 205

Lys Ile Glu Asn Thr Lys Lys Lys Ile Phe Gly Ala Glu Ala
    210                 215                 220


<210> SEQ ID NO 19
<211> LENGTH: 196
<212> TYPE: PRT
<213> ORGANISM: PMC Virus

<400> SEQUENCE: 19

Ser Pro Tyr Cys Pro Val Ala Lys Arg Val Phe Asn Ile Ile Tyr Thr
1               5                   10                  15

Asn Asn Cys Thr Pro Leu Gly Leu Pro Asp Lys Ser Lys Ile Ile Gly
            20                  25                  30

Pro Gly Thr Phe Asp Ile Ser Gly Arg Asp Glu Phe Ile Phe Pro Lys
        35                  40                  45

Leu Pro Tyr His Val Asp Asp Phe Ile Leu Leu Ser Leu Ile Ala Met
    50                  55                  60

Ser Asp Phe Ala Pro Glu Thr Ser Ser Ile Ile Tyr Leu Ala Leu His
65                  70                  75                  80

Tyr Leu Met Pro Ser Asn Asp Asn Arg Asp Phe Val Met Asp Leu Asp
                85                  90                  95

Pro Asn Lys Leu Asn Leu Thr Ala Thr Lys Ser Val Ala Ser Val Val
            100                 105                 110

Pro Thr Ser Val Asn Val Leu Gly Glu Trp Val Cys Val Lys Pro Ser
        115                 120                 125

Trp Trp Pro Tyr Ser Ala Glu Ile Thr Asn Leu Ile Gly Gly Val Ile
    130                 135                 140

Thr Val Ala Asp Leu Val Ile Lys Thr Ile Glu Glu Leu Leu Asn Leu
145                 150                 155                 160

Trp Thr Glu Ala Thr Ala Val Ala Phe Leu Ala Ala Leu Ile Lys Ile
                165                 170                 175

Phe Arg Gly Gln Pro Ile Gln Ala Val Ala Trp Leu Ile Ile Ile Gly
            180                 185                 190

Gly Ala Gln Ala
        195


<210> SEQ ID NO 20
<211> LENGTH: 377
<212> TYPE: PRT
<213> ORGANISM: PMC Virus

<400> SEQUENCE: 20

Gln Thr Cys Asn Pro Glu Phe Met Tyr Ala Leu Ala Lys Asn Thr Ser
1               5                   10                  15
```

```
Ile Gly Ser Leu Gly Pro Glu Ser Leu Thr Thr Arg Trp Tyr Gln Leu
            20                  25                  30

Thr Ser Gly Phe Lys Leu Thr Asp Ser Thr Ile Glu Val Thr Cys Val
        35                  40                  45

Gly Ala Asn Met Arg Ile His Val Val Cys Pro Leu Val Ser Asp Arg
    50                  55                  60

Tyr Leu Ala Ile Asn His Pro Arg Ala Leu Pro Thr Thr Ala Trp Phe
65                  70                  75                  80

Arg Lys Ile His Thr Gln His Glu Val Pro Arg Glu Arg Ile Met Ser
                85                  90                  95

Glu Ser Lys Arg Arg Tyr Thr Cys Pro Cys Gly Ser Lys Pro Val Val
            100                 105                 110

Arg Ser Thr Thr Gln Phe Asn Pro Ile Ser Ile Ser Thr Pro Ser Phe
        115                 120                 125

Glu Leu Glu Cys Pro Arg Gly Trp Thr Gly Ala Val Glu Cys Thr Leu
    130                 135                 140

Val Ser Pro Ser Thr Leu Thr Thr Glu Thr Ile Phe Thr Tyr Arg Lys
145                 150                 155                 160

Pro Lys Pro Phe Gly Leu Glu Asn Trp Cys Lys Tyr Thr Val Val Glu
                165                 170                 175

Lys Gly Ile Leu Tyr Ser Cys Lys Phe Gly Gly Asn Ser Thr Cys Ile
            180                 185                 190

Lys Gly Leu Ile Val Lys Gly Gln Arg Glu Asp Lys Val Arg Tyr Cys
        195                 200                 205

Glu Trp Cys Gly Tyr Lys Phe Ser Ser Pro Asn Gly Leu Pro Gln Tyr
    210                 215                 220

Pro Leu Gly Leu Cys Glu Lys Glu Gln Ser Glu Gly Leu Arg Asp Tyr
225                 230                 235                 240

Gly Asp Phe Pro Cys Cys Asn Asn Gly Thr Cys Ile Asp Lys Glu Gly
                245                 250                 255

Ser Val Gln Cys Tyr Ile Gly Asp Lys Lys Val Thr Val Lys Leu Tyr
            260                 265                 270

Asn Ala Ser Leu Leu Ala Pro Met Pro Cys Lys Pro Ile Val Tyr Asn
        275                 280                 285

Ser Gln Gly Pro Pro Ala Pro Lys Thr Cys Thr Tyr Arg Trp Ala Ser
    290                 295                 300

Thr Leu Glu Asn Lys Tyr Tyr Glu Pro Arg Asp Ser Tyr Tyr Gln Gln
305                 310                 315                 320

Tyr Ile Ile Lys Ser Gly Tyr Gln Tyr Trp Phe Asp Leu Thr Ala Lys
                325                 330                 335

Asp His Val Ala Asp Trp Ile Thr Lys Tyr Phe Pro Ile Ile Ile Val
            340                 345                 350

Ala Leu Leu Gly Gly Arg Gly Thr Leu Trp Val Leu Ile Ala Tyr Glu
        355                 360                 365

Leu Leu Thr Gln Tyr Glu Val Val Gly
    370                 375
```

<210> SEQ ID NO 21
<211> LENGTH: 72
<212> TYPE: PRT
<213> ORGANISM: PMC Virus

<400> SEQUENCE: 21

```
Asp Glu Asn Ile Val Ala Gln Ala Glu Ala Leu Val Ile Gly Asn Ile
1               5                   10                  15
```

-continued

```
Leu Met Ser Leu Asp Leu Glu Ile Ile Ser Cys Phe Leu Leu Leu Leu
            20                  25                  30

Ile Val Val Lys Lys Gln Ala Val Arg Arg Thr Leu Ala Leu Leu Phe
        35                  40                  45

His Trp Ile Thr Met Asn Pro Phe Gln Ser Val Met Ile Thr Val Val
    50                  55                  60

Tyr Phe Val Gly Leu Val Arg Ala
65                  70


<210> SEQ ID NO 22
<211> LENGTH: 468
<212> TYPE: PRT
<213> ORGANISM: PMC Virus

<400> SEQUENCE: 22

Glu Glu Gly Thr Lys Glu Gly Ser Thr Ser Gly Pro Pro Ile His Val
1               5                   10                  15

Val Ala Ile Leu Leu Phe Leu Leu Tyr His Thr Val Lys Tyr Lys Asp
            20                  25                  30

Phe Asn Ile Ala Met Ile Leu Leu Ile Thr Leu Ser Leu Lys Ser Ser
        35                  40                  45

Ser Tyr Ile His Thr Ser Leu Tyr Glu Ile Pro Leu Leu Val Ala Val
    50                  55                  60

Ile Ser Leu Thr Cys Ser Ile Tyr Ile Phe Asp Leu Gln Val Lys Ser
65                  70                  75                  80

Lys Leu Val Ala Pro Thr Ile Gly Ile Ile Gly Val Thr Leu Ala Met
                85                  90                  95

Arg Val Leu Trp Leu Val Arg Gln Met Thr Ile Pro Thr Pro Ser Val
            100                 105                 110

Ser Ile Ser Leu Ile Asp Pro Lys Met Val Ile Ile Leu Tyr Leu Ile
        115                 120                 125

Ser Leu Thr Ile Thr Val Asn His Asn Leu Asp Leu Ala Ser Tyr Cys
    130                 135                 140

Leu Lys Leu Gly Pro Phe Ile Leu Ser Phe Leu Thr Met Trp Val Asp
145                 150                 155                 160

Val Val Ile Leu Leu Leu Met Leu Pro Trp Tyr Glu Leu Val Lys Val
                165                 170                 175

Tyr Tyr Leu Lys Lys Lys Lys Glu Asp Val Glu Thr Trp Phe Gln Asn
            180                 185                 190

Ser Gly Ile Ser Thr Gln Glu Thr Ser Pro Tyr Gly Phe Asp Phe Ser
        195                 200                 205

Ser Pro Gly Glu Gly Val His Thr Leu Pro Met Gln Asn Lys Thr Lys
    210                 215                 220

Phe Cys Arg Thr Ala Tyr Met Thr Val Leu Arg Ala Leu Val Ile Thr
225                 230                 235                 240

Ala Ile Ser Ser Val Trp Lys Pro Ile Ile Leu Ala Glu Leu Leu Ile
                245                 250                 255

Glu Ala Val Tyr Trp Thr His Ile Lys Ile Ala Lys Glu Leu Ala Gly
            260                 265                 270

Ser Ser Arg Phe Val Ala Arg Phe Ile Ala Ser Ile Ile Glu Leu Asn
        275                 280                 285

Trp Ala Met Asp Glu Lys Glu Ala Ser Arg Tyr Lys Arg Phe Tyr Leu
    290                 295                 300

Leu Ser Ser Lys Ile Thr Asp Leu Met Val Lys His Lys Ile Gln Asn
305                 310                 315                 320
```

```
Glu Thr Val Lys Ser Trp Phe Glu Glu Thr Glu Ile Phe Gly Ile Gln
                325                 330                 335

Lys Val Ala Met Val Ile Arg Ala His Ser Leu Ser Leu Glu Pro Asn
            340                 345                 350

Ala Ile Leu Cys Ser Val Cys Glu Glu Lys Gln Asn Gln Lys Ala Lys
        355                 360                 365

Arg Pro Cys Pro Lys Cys Gly Ser Arg Gly Thr Gln Ile Lys Cys Gly
    370                 375                 380

Leu Thr Leu Ala Glu Phe Glu Glu Glu His Tyr Lys Lys Ile Tyr Ile
385                 390                 395                 400

Leu Glu Gly Gln Asp Glu Thr Pro Met Arg Lys Glu Glu Arg Gln Gln
                405                 410                 415

Val Thr Tyr Val Ser Arg Gly Ala Leu Phe Leu Arg Asn Leu Pro Ile
            420                 425                 430

Leu Ala Ser Lys Asn Lys Tyr Leu Leu Val Gly Asn Leu Gly Met Glu
        435                 440                 445

Leu Gln Asp Leu Glu Ser Met Gly Trp Ile Ile Arg Gly Pro Ala Val
    450                 455                 460

Cys Lys Lys Ile
465


<210> SEQ ID NO 23
<211> LENGTH: 676
<212> TYPE: PRT
<213> ORGANISM: PMC Virus

<400> SEQUENCE: 23

Ile His His Glu Lys Cys Arg Pro Ser Ile Pro Asp Lys Leu Met Ala
1               5                   10                  15

Phe Phe Gly Ile Met Pro Arg Gly Val Thr Pro Arg Ala Pro Thr Arg
            20                  25                  30

Phe Pro Val Ser Leu Leu Lys Ile Arg Arg Gly Phe Glu Thr Gly Trp
        35                  40                  45

Ala Tyr Thr His Pro Gly Gly Val Ser Ser Val Met His Val Thr Ala
    50                  55                  60

Gly Ser Asp Ile Tyr Val Asn Asp Ser Ile Gly Arg Thr Lys Ile Gln
65                  70                  75                  80

Cys Gln Asp Lys Asn Thr Thr Thr Asp Glu Cys Glu Tyr Gly Val Lys
                85                  90                  95

Thr Asp Ser Gly Cys Ser Asp Gly Ala Arg Cys Tyr Val Ile Asn Pro
            100                 105                 110

Glu Ala Thr Asn Ile Ala Gly Thr Lys Gly Ala Met Val His Leu Arg
        115                 120                 125

Lys Ala Gly Gly Glu Phe Asn Cys Val Thr Ala Gln Gly Thr Pro Ala
    130                 135                 140

Phe Tyr Asn Leu Lys Asn Leu Lys Gly Trp Ser Gly Leu Pro Ile Phe
145                 150                 155                 160

Glu Ala Ala Thr Gly Arg Val Val Gly Arg Val Lys Ala Gly Lys Asn
                165                 170                 175

Thr Asp Asn Ala Pro Thr Thr Ile Met Ser Gly Thr Gln Val Ala Lys
            180                 185                 190

Pro Ser Glu Cys Asp Leu Glu Ser Val Val Arg Lys Leu Glu Thr Met
        195                 200                 205

Asn Arg Gly Glu Phe Lys Gln Val Thr Leu Ala Thr Gly Ala Gly Lys
    210                 215                 220
```

-continued

```
Thr Thr Met Leu Pro Lys Leu Leu Ile Glu Ser Ile Gly Arg His Lys
225                 230                 235                 240

Arg Val Leu Val Leu Ile Pro Leu Arg Ala Ala Ala Glu Gly Val Tyr
                245                 250                 255

Gln Tyr Met Arg Thr Lys His Pro Ser Ile Ser Phe Asn Leu Arg Ile
            260                 265                 270

Gly Asp Leu Lys Glu Gly Asp Met Ala Thr Gly Ile Thr Tyr Ala Ser
        275                 280                 285

Tyr Gly Tyr Phe Cys Gln Met Asp Met Pro Arg Leu Glu Asn Ala Met
    290                 295                 300

Lys Glu Tyr His Tyr Ile Phe Leu Asp Glu Tyr His Cys Ala Thr Pro
305                 310                 315                 320

Glu Gln Leu Ala Val Met Ser Lys Ile His Arg Phe Gly Glu Ser Val
                325                 330                 335

Arg Val Ile Ala Met Thr Ala Thr Pro Ser Gly Thr Val Ser Thr Thr
            340                 345                 350

Gly Gln Lys Phe Thr Ile Glu Glu Val Val Val Pro Glu Val Met Lys
        355                 360                 365

Gly Glu Asp Leu Ala Asp Asp Tyr Ile Glu Ile Ala Gly Leu Lys Val
    370                 375                 380

Pro Lys Lys Glu Leu Glu Gly Asn Val Leu Thr Phe Val Pro Thr Arg
385                 390                 395                 400

Lys Met Ala Ser Glu Thr Ala Lys Lys Leu Thr Thr Gln Gly Tyr Asn
                405                 410                 415

Ala Gly Tyr Tyr Phe Ser Gly Glu Asp Pro Ser Ser Leu Arg Thr Thr
            420                 425                 430

Thr Ser Lys Ser Pro Tyr Ile Val Val Ala Thr Asn Ala Ile Glu Ser
        435                 440                 445

Gly Val Thr Leu Pro Asp Leu Asp Thr Val Ile Asp Thr Gly Met Lys
    450                 455                 460

Cys Glu Lys Arg Leu Arg Ile Glu Asn Lys Ala Pro Tyr Ile Val Thr
465                 470                 475                 480

Gly Leu Lys Arg Met Ala Ile Thr Thr Gly Glu Gln Ala Gln Arg Lys
                485                 490                 495

Gly Arg Val Gly Arg Val Lys Pro Gly Arg Tyr Leu Arg Gly Pro Glu
            500                 505                 510

Asn Thr Ala Gly Glu Lys Asp Tyr His Tyr Asp Leu Leu Gln Ala Gln
        515                 520                 525

Arg Tyr Gly Ile Gln Asp Ser Ile Asn Ile Thr Lys Ser Phe Arg Glu
    530                 535                 540

Met Asn Tyr Asp Trp Ala Leu Tyr Glu Glu Asp Pro Leu Lys Ile Ala
545                 550                 555                 560

Gln Leu Glu Leu Leu Asn Thr Leu Leu Ile Ser Arg Asp Leu Pro Val
                565                 570                 575

Val Thr Lys Asn Leu Met Ala Arg Thr Thr His Pro Glu Pro Ile Gln
            580                 585                 590

Leu Ala Tyr Asn Ser Leu Glu Thr Pro Val Pro Val Ala Phe Pro Lys
        595                 600                 605

Val Lys Asn Gly Glu Val Thr Asp Ala His Glu Thr Tyr Glu Leu Met
    610                 615                 620

Thr Cys Arg Lys Leu Glu Lys Asp Pro Pro Ile Tyr Leu Tyr Ala Thr
625                 630                 635                 640

Glu Glu Glu Asp Leu Val Val Asp Ile Leu Gly Leu Lys Trp Pro Asp
                645                 650                 655
```

```
Ala Thr Glu Arg Ala Val Leu Glu Val Gln Asp Ala Leu Gly Gln Ile
            660                 665                 670

Thr Gly Leu Ser
        675


<210> SEQ ID NO 24
<211> LENGTH: 63
<212> TYPE: PRT
<213> ORGANISM: PMC Virus

<400> SEQUENCE: 24

Ala Gly Glu Thr Ala Leu Leu Ile Ala Leu Leu Gly Trp Val Gly Tyr
1               5                   10                  15

Glu Ala Leu Val Lys Arg His Val Pro Met Val Thr Asp Ile Tyr Thr
            20                  25                  30

Leu Glu Asp Glu Lys Leu Glu Asp Thr Thr His Leu Gln Phe Ala Pro
        35                  40                  45

Asp Asp Leu Asn Asn Ser Asp Thr Ile Glu Leu Gln Asp Leu Ser
    50                  55                  60


<210> SEQ ID NO 25
<211> LENGTH: 347
<212> TYPE: PRT
<213> ORGANISM: PMC Virus

<400> SEQUENCE: 25

Asn His Gln Ile Gln Gln Ile Leu Glu Gly Gly Lys Glu Tyr Val Gly
1               5                   10                  15

Gln Ala Tyr Gln Phe Leu Arg Leu Gln Ala Glu Arg Ala Ala Asn Ser
            20                  25                  30

Asp Lys Gly Lys Lys Ala Met Ala Ala Ala Pro Leu Leu Ala His Lys
        35                  40                  45

Phe Leu Glu Tyr Leu Gln Glu His Ala Gly Asp Ile Lys Lys Tyr Gly
    50                  55                  60

Leu Trp Gly Val His Thr Ala Leu Tyr Asn Ser Ile Lys Glu Arg Leu
65                  70                  75                  80

Gly His Glu Thr Ala Phe Ala Ser Leu Val Ile Lys Trp Ile Ala Phe
                85                  90                  95

Ser Ser Asp Gly Val Pro Gly Met Ile Lys Gln Ala Ala Val Asp Leu
            100                 105                 110

Val Val Tyr Tyr Ile Ile Asn Arg Pro Glu Tyr Gln Gly Asp Lys Glu
        115                 120                 125

Thr Gln Asn Ala Gly Arg Gln Phe Val Gly Ser Leu Phe Val Ser Cys
    130                 135                 140

Leu Ala Glu Tyr Thr Phe Lys Asn Phe Asn Lys Ser Ala Leu Glu Gly
145                 150                 155                 160

Leu Ile Glu Pro Ala Leu Ser Tyr Leu Pro Tyr Ala Ser Ser Ala Leu
                165                 170                 175

Lys Leu Phe Leu Pro Thr Arg Leu Glu Ser Val Val Ile Leu Ser Thr
            180                 185                 190

Thr Ile Tyr Arg Thr Tyr Leu Ser Ile Arg Lys Gly Ser Ser Gln Gly
        195                 200                 205

Leu Ala Gly Leu Ala Val Ser Ser Ala Met Glu Ile Met Asn Gln Asn
    210                 215                 220

Pro Ile Ser Val Ala Ile Ala Leu Ala Leu Gly Val Gly Ala Ile Ala
225                 230                 235                 240
```

```
Ala His Asn Ala Ile Glu Ser Ser Glu Ala Lys Arg Thr Leu Leu Met
                245                 250                 255

Lys Val Phe Val Lys Asn Phe Leu Asp Gln Ala Ala Thr Asp Glu Leu
            260                 265                 270

Val Lys Glu Asn Pro Glu Lys Ile Ile Met Ala Val Phe Glu Gly Ile
        275                 280                 285

Gln Thr Ala Gly Asn Pro Leu Arg Leu Val Tyr His Leu Tyr Ala Met
    290                 295                 300

Phe Tyr Lys Gly Trp Thr Ala Ala Glu Ile Ala Glu Lys Thr Ala Gly
305                 310                 315                 320

Arg Asn Ile Phe Val Leu Thr Ile Phe Glu Gly Leu Glu Met Leu Gly
                325                 330                 335

Leu Asp Ala Asp Ser Lys Trp Arg Asn Leu Ser
            340                 345


<210> SEQ ID NO 26
<211> LENGTH: 505
<212> TYPE: PRT
<213> ORGANISM: PMC Virus

<400> SEQUENCE: 26

Ser Asn Tyr Leu Ile Asp Ala Val Lys Lys Ile Ile Glu Lys Met Thr
1               5                   10                  15

Lys Thr Ala Thr Ser Phe Thr Tyr Ser Phe Leu Lys Ser Leu Leu Pro
            20                  25                  30

Ala Pro Phe Ser Cys Thr Lys Ser Glu Arg Asp Pro Arg Ile Gly Trp
        35                  40                  45

Pro Gln Lys Asp Tyr Asp Tyr Leu Glu Val Arg Cys Ala Cys Gly Tyr
    50                  55                  60

Asn Arg Arg Ala Ile Lys Arg Asp Ser Gly Pro Val Leu Trp Glu Thr
65                  70                  75                  80

Leu Glu Glu Thr Gly Pro Glu Tyr Cys His Asn Arg Gly Glu Arg Gly
                85                  90                  95

Leu Ser Asn Val Lys Thr Thr Arg Cys Phe Val Gln Gly Glu Glu Ile
            100                 105                 110

Pro Pro Ile Ala Leu Arg Lys Gly Val Gly Glu Met Leu Val Lys Gly
        115                 120                 125

Val Ser Phe Arg Ile Asp Phe Asp Lys Asp Lys Ile Leu Ser Thr Asp
    130                 135                 140

Lys Trp Lys Val Pro His Arg Ala Val Thr Ser Ile Phe Glu Asp Trp
145                 150                 155                 160

Gln Gly Ile Gly Tyr Arg Glu Ala Tyr Leu Gly Thr Lys Pro Asp Tyr
                165                 170                 175

Gly Gly Leu Val Pro Arg Ser Cys Val Thr Val Thr Lys Gln Gly Leu
            180                 185                 190

Thr Phe Leu Lys Thr Ala Arg Gly Met Ala Phe Thr Thr Asp Leu Thr
        195                 200                 205

Ile Gln Asn Ile Lys Met Leu Ile Ala Thr Cys Phe Lys Asn Lys Val
    210                 215                 220

Lys Glu Gly Glu Ile Pro Ala Thr Ile Glu Gly Glu Thr Trp Ile Asn
225                 230                 235                 240

Ile Pro Leu Val Asn Glu Asp Thr Gly Thr Ile Lys Pro Ser Phe Gly
                245                 250                 255

Glu Arg Val Ile Pro Glu Pro Tyr Glu Glu Asp Pro Leu Glu Gly Pro
            260                 265                 270
```

```
Ser Val Ile Val Glu Thr Gly Gly Ile Ala Ile Asn Gln Ile Gly Val
        275                 280                 285

Asn Pro Gln Ser Ser Thr Cys Gly Thr Val Phe Thr Ala Val Lys Asp
    290                 295                 300

Leu Cys Gln Thr Val Ser Asn Lys Ala Lys Asn Ile Lys Ile Gly Phe
305                 310                 315                 320

Ser Glu Gly Gln Tyr Pro Gly Pro Gly Val Ala Lys Lys Thr Leu Asn
                325                 330                 335

Gln Leu Ile Gln Asp Glu Asp Pro Lys Pro Phe Ile Phe Val Cys Gly
            340                 345                 350

Ser Asp Lys Ser Met Ser Asn Arg Ala Lys Thr Ala Arg Asn Ile Lys
        355                 360                 365

Arg Ile Thr Thr Thr Thr Pro Glu Lys Phe Arg Asp Leu Ala Lys Asn
    370                 375                 380

Lys Lys Leu Ile Ile Val Leu Leu Gly Asp Arg Tyr His Glu Asp Ile
385                 390                 395                 400

Glu Lys Tyr Ala Asp Phe Lys Gly Thr Phe Leu Thr Arg Gln Thr Leu
                405                 410                 415

Glu Ala Leu Ala Ser Ala Lys Ala Val Glu Lys Asp Met Thr Lys Lys
            420                 425                 430

Glu Ala Ala Arg Val Leu Ala Met Glu Glu Lys Asp Glu Leu Glu Leu
        435                 440                 445

Pro Gly Trp Leu His Thr Asp Ala Pro Lys Phe Leu Asp Ile Thr Lys
    450                 455                 460

Asp Asn Ile Thr His His Leu Ile Gly Asp Met Gln Ser Leu Arg Glu
465                 470                 475                 480

Arg Ala Gly Glu Ile Gly Ala Lys Ala Thr Thr Gln Ile Thr Lys Lys
                485                 490                 495

Gly Ser Val Tyr Thr Ile Asn Leu Ser
            500                 505


<210> SEQ ID NO 27
<211> LENGTH: 693
<212> TYPE: PRT
<213> ORGANISM: PMC Virus

<400> SEQUENCE: 27

Thr Trp Trp Glu Ser Glu Arg Leu Ala Ser Leu Glu Pro Leu Phe Arg
1               5                   10                  15

Glu Leu Leu Ser Lys Cys Arg Pro Val Asp Arg Glu Thr Tyr Lys Asn
            20                  25                  30

Cys His Phe Ala Thr Ala Ala Gln Leu Ala Gly Gly Asn Trp Val Pro
        35                  40                  45

Val Ala Pro Val Val His Leu Gly Glu Ile Pro Val Lys Lys Lys Lys
    50                  55                  60

Thr Leu Pro Tyr Glu Ala Tyr Lys Leu Leu Lys Glu Met Val Asp Ser
65                  70                  75                  80

Glu Lys Glu Phe His Lys Pro Val Ser Arg Glu Lys His Gln Trp Ile
                85                  90                  95

Leu Asn Lys Val Lys Thr Gly Gly Asp Leu Gly Leu Lys Asn Leu Val
            100                 105                 110

Cys Pro Gly Arg Val Gly Glu Pro Ile Leu Arg Glu Lys Lys Lys Phe
        115                 120                 125

Asn Ile Tyr Asn Lys Arg Ile Thr Ser Thr Met Leu Ser Val Gly Ile
    130                 135                 140
```

-continued

```
Arg Pro Glu Lys Leu Pro Val Val Arg Ala Gln Thr Ser Thr Lys Glu
145                 150                 155                 160

Phe His Glu Ala Ile Arg Asp Lys Ile Asp Lys Lys Ala Asn Thr Gln
                165                 170                 175

Thr Pro Gly Leu His Lys Glu Leu Leu Glu Ile Phe Asn Ser Ile Cys
            180                 185                 190

Ala Ile Pro Glu Leu Arg Asn Thr Tyr Lys Glu Val Asp Trp Asp Val
        195                 200                 205

Leu Thr Ser Gly Ile Asn Arg Lys Gly Ala Ala Gly Tyr Phe Glu Lys
    210                 215                 220

Met Asn Ile Gly Glu Ile Ile Asp Ser Asp Lys Lys Ser Val Glu Gln
225                 230                 235                 240

Leu Ile Lys Arg Met Lys Ser Gly Leu Glu Phe Asn Tyr Tyr Glu Thr
                245                 250                 255

Ala Ile Pro Lys Asn Glu Lys Arg Ala Val Val Asp Asp Trp Met Glu
            260                 265                 270

Gly Asp Tyr Val Glu Glu Lys Arg Pro Arg Val Ile Gln Tyr Pro Glu
        275                 280                 285

Ala Lys Met Arg Leu Ala Ile Thr Lys Val Met Tyr Asn Trp Val Lys
    290                 295                 300

Gln Lys Pro Ile Val Ile Pro Gly Tyr Glu Gly Lys Thr Pro Leu Phe
305                 310                 315                 320

His Val Phe Asp Lys Val His Lys Glu Trp Lys Asn Phe Asn Ser Pro
                325                 330                 335

Val Ala Val Ser Phe Asp Thr Lys Ala Trp Asp Thr Gln Val Thr Pro
            340                 345                 350

Lys Asp Leu Leu Leu Ile Ser Glu Ile Gln Lys Tyr Tyr Tyr Lys Lys
        355                 360                 365

Glu Tyr His Arg Phe Ile Asp Asn Leu Thr Glu Lys Met Val Glu Val
    370                 375                 380

Pro Val Val Cys Glu Asp Gly Asn Val Tyr Ile Arg Glu Gly Gln Arg
385                 390                 395                 400

Gly Ser Gly Gln Pro Asp Thr Ser Ala Gly Asn Ser Met Leu Asn Val
                405                 410                 415

Leu Thr Met Ile Tyr Ala Phe Cys Lys Ala Asn Ser Ile Pro Tyr Ser
            420                 425                 430

Ala Phe His Arg Val Ala Lys Ile His Val Cys Gly Asp Asp Gly Phe
        435                 440                 445

Leu Ile Thr Glu Lys Ser Phe Gly Glu Ala Phe Ala Ile Lys Gly Pro
    450                 455                 460

Gln Ile Leu Met Glu Ala Gly Lys Pro Gln Lys Leu Ile Gly Glu Phe
465                 470                 475                 480

Gly Leu Lys Leu Ala Tyr Lys Phe Asp Asp Ile Glu Phe Cys Ser His
                485                 490                 495

Thr Pro Ile Lys Val Arg Trp Ala Asp Asn Asn Thr Ser Tyr Met Pro
            500                 505                 510

Gly Arg Asp Thr Ala Thr Ile Leu Ala Lys Met Ala Thr Arg Leu Asp
        515                 520                 525

Ser Ser Gly Glu Arg Gly Thr Glu Gly Tyr Glu Leu Ala Val Ala Phe
    530                 535                 540

Ser Phe Leu Leu Met Tyr Ser Trp Asn Pro Leu Val Arg Arg Ile Cys
545                 550                 555                 560

Leu Leu Val Met Ser Thr Ile Asp Thr Lys Glu Ala Ser Gln Asn Asn
                565                 570                 575
```

```
Thr Ile Tyr Thr Phe Arg Gly Asp Pro Ile Gly Ala Tyr Thr Glu Val
            580                 585                 590

Ile Gly Tyr Arg Leu Asp Gln Leu Lys Gln Thr Glu Phe Ser Lys Leu
        595                 600                 605

Ala Gln Leu Asn Leu Ser Met Ala Ile Leu Gln Ile Tyr Asn Lys Asn
    610                 615                 620

Thr Thr Lys Arg Leu Ile Glu Asp Cys Val Lys Leu Gly Asn Gln Asn
625                 630                 635                 640

Lys Gln Ile Leu Val Asn Ala Asp Arg Leu Ile Ser Lys Lys Thr Gly
                645                 650                 655

Tyr Thr Tyr Glu Pro Thr Ala Gly His Thr Lys Ile Gly Lys His Tyr
            660                 665                 670

Glu Glu Ile Asn Leu Leu Lys Asp Thr Pro Gln Lys Thr Val Tyr Gln
        675                 680                 685

Gly Thr Glu Arg Tyr
    690


<210> SEQ ID NO 28
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 28

cacatctagc agcagactat ga                                              22


<210> SEQ ID NO 29
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 29

gtaccagttg caccaccc                                                   18


<210> SEQ ID NO 30
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 30

tgaaaaggat tcacgg                                                     16


<210> SEQ ID NO 31
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 31

aaaccgacga agtagacc                                                   18


<210> SEQ ID NO 32
<211> LENGTH: 18
<212> TYPE: DNA
<213> ORGANISM: Artificial Sequence
<220> FEATURE:
<223> OTHER INFORMATION: oligonucleotide primer
```

<400> SEQUENCE: 32
agacgagaac atagtggc 18

<210> SEQ ID NO 33
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 33
gaaacagtaa agccaacg 18

<210> SEQ ID NO 34
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 34
ctggtaatcg gaaacatc 18

<210> SEQ ID NO 35
<211> LENGTH: 17
<212> TYPE: DNA
<213> ORGANISM: Artificial Sequence
<220> FEATURE:
<223> OTHER INFORMATION: oligonucleotide primer

<400> SEQUENCE: 35
gggaccgagg gatacga 17

<210> SEQ ID NO 36
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 36
agaggtaatt gggtat 16

<210> SEQ ID NO 37
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 37
cagcaggttg atttcttcat 20

<210> SEQ ID NO 38
<211> LENGTH: 14
<212> TYPE: DNA
<213> ORGANISM: Artificial Sequence
<220> FEATURE:
<223> OTHER INFORMATION: oligonucleotide primer

<400> SEQUENCE: 38
ttgccaagtt tcac 14

<210> SEQ ID NO 39
<211> LENGTH: 18

<212> TYPE: DNA
<213> ORGANISM: Artificial Sequence
<220> FEATURE:
<223> OTHER INFORMATION: oligonucleotide primer

<400> SEQUENCE: 39
aaaccgccga agtaaacc 18

<210> SEQ ID NO 40
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 40
ctggagccct ggtaatgg 18

<210> SEQ ID NO 41
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 41
gacgggaatg ggttca 16

<210> SEQ ID NO 42
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 42
taggtgcttc ttattggtat 20

<210> SEQ ID NO 43
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 43
catgcccata gtaggac 17

<210> SEQ ID NO 44
<211> LENGTH: 18
<212> TYPE: DNA
<213> ORGANISM: Artificial Sequence
<220> FEATURE:
<223> OTHER INFORMATION: Oligonucleotide primer
<220> FEATURE:
<221> NAME/KEY: VARIANT
<222> LOCATION: 8
<223> OTHER INFORMATION: r = g or a
<220> FEATURE:
<221> NAME/KEY: VARIANT
<222> LOCATION: 14
<223> OTHER INFORMATION: m = a or c

<400> SEQUENCE: 44
accagttrca ccamccat 18

<210> SEQ ID NO 45
<211> LENGTH: 20

<212> TYPE: DNA
<213> ORGANISM: Artificial Sequence
<220> FEATURE:
<223> OTHER INFORMATION: Oligonucleotide primer

<400> SEQUENCE: 45
agggctctca catggttgtc 20

<210> SEQ ID NO 46
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 46
ccattaccag ggctccag 18

<210> SEQ ID NO 47
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 47
cacatctagc agcagactat ga 22

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 48
taggtgcttc ttattggtat 20

<210> SEQ ID NO 49
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 49
cgttggcttt actgtttcat tg 22

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 50
tccccgaagc ttggtttaat 20

<210> SEQ ID NO 51
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 51
gtcaggcctg cctatctttg 20

-continued

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 52
tccccgaagc ttggtttaat 20

<210> SEQ ID NO 53
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 53
cgggaccatt aaaccaagc 19

<210> SEQ ID NO 54
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 54
cagggggttc caagaataca 20

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 55
ggtgtactca ccgcttagcc 20

<210> SEQ ID NO 56
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 56
ttgctacaat cgcccttctt 20

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 57
agggagaatg acagggtctg 20

<210> SEQ ID NO 58
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 58
acaaaggagc aaaacccaag 20

<210> SEQ ID NO 59
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 59
gtcacgttgg tggaccctac 20

<210> SEQ ID NO 60
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 60
agccagaaat gccacagc 18

<210> SEQ ID NO 61
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 61
acctgtgtgg gtgctaacat 20

<210> SEQ ID NO 62
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 62
ttactttgtc ttcccgttgc 20

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 63
ccaagaaact tccccatacg 20

<210> SEQ ID NO 64
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 64
ttccacatcc tctttcttct ttt 23

<210> SEQ ID NO 65
<211> LENGTH: 20

<212> TYPE: DNA
<213> ORGANISM: Artificial Sequence
<220> FEATURE:
<223> OTHER INFORMATION: Oligonucleotide primer

<400> SEQUENCE: 65
gctggccctc gaatgatcca 20

<210> SEQ ID NO 66
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 66
gttccctgtg tccttgctga 20

<210> SEQ ID NO 67
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 67
tgtttttgtc ttggcactgg 20

<210> SEQ ID NO 68
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 68
gagcacaaca gggcagaaat 20

<210> SEQ ID NO 69
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 69
ccatcttcct tgtaggcaca 20

<210> SEQ ID NO 70
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 70
gtcaggcctg cctatctttg 20

<210> SEQ ID NO 71
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 71
ggagaagtca ctgacgcaca 20

<210> SEQ ID NO 72
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 72
gccatttcaa tcccagtatg 20

<210> SEQ ID NO 73
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 73
ggggtccaca cagcattgta 20

<210> SEQ ID NO 74
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 74
cccttgatac tcacgcctgt 20

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 75
gccgactcaa aatggagaaa 20

<210> SEQ ID NO 76
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 76
gccaccctat tcttggatct c 21

<210> SEQ ID NO 77
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 77
aaatgagaag agggcagtgg 20

<210> SEQ ID NO 78
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 78
aaggccacca ctcaaatcac 20

<210> SEQ ID NO 79
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 79
aggcttctgc ttgacccagt 20

<210> SEQ ID NO 80
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 80
tccccgaagc ttggtttaat 20

<210> SEQ ID NO 81
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 81
ctaatacgac tcactatagg gcaagcagtg gtatcaacgc agagt 45

<210> SEQ ID NO 82
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 82
ctaatacgac tcactatagg gc 22

<210> SEQ ID NO 83
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 83
aagcagtggt atcaacgcag at 22

<210> SEQ ID NO 84
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 84
ctaatacgac tcactatagg gcaagcagtg gtatcaacgc agagt 45

<210> SEQ ID NO 85
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 85
ctaatacgac tcactatagg gc 22

<210> SEQ ID NO 86
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 86
aagcagtggt atcaacgcag at 22

<210> SEQ ID NO 87
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 87
cagttggtgt gatccatgat cct 23

<210> SEQ ID NO 88
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 88
ggcctcaccc tgcaacttt 19

<210> SEQ ID NO 89
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 89
aagtcttcag cagttaact 19